United States Patent
Zhao et al.

(10) Patent No.: US 12,215,137 B2
(45) Date of Patent: Feb. 4, 2025

(54) COMPOSITIONS AND METHODS FOR T CELL DELIVERY OF THERAPEUTIC MOLECULES

(71) Applicant: The Trustees of the University of Pennsylania, Philadelphia, PA (US)

(72) Inventors: Yangbing Zhao, Lumberton, NJ (US); Carl H. June, Merion Station, PA (US); Xiaojun Liu, Wallingford, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 818 days.

(21) Appl. No.: 17/038,676

(22) Filed: Sep. 30, 2020

(65) Prior Publication Data
US 2021/0008188 A1 Jan. 14, 2021

Related U.S. Application Data

(62) Division of application No. 15/544,816, filed as application No. PCT/US2015/058192 on Oct. 30, 2015, now Pat. No. 10,828,353.

(60) Provisional application No. 62/110,489, filed on Jan. 31, 2015.

(51) Int. Cl.
| | |
|---|---|
| C07K 14/705 | (2006.01) |
| A61K 39/00 | (2006.01) |
| A61K 39/395 | (2006.01) |
| C07K 14/71 | (2006.01) |
| C07K 14/715 | (2006.01) |
| C07K 16/28 | (2006.01) |
| C12N 5/0783 | (2010.01) |
| C12N 15/00 | (2006.01) |

(52) U.S. Cl.
CPC .. C07K 14/70578 (2013.01); A61K 39/39558 (2013.01); A61K 39/4611 (2023.05); A61K 39/4631 (2023.05); A61K 39/464406 (2023.05); A61K 39/464412 (2023.05); C07K 14/70521 (2013.01); C07K 14/71 (2013.01); C07K 14/7155 (2013.01); C07K 16/2818 (2013.01); C07K 16/2827 (2013.01); C07K 16/2863 (2013.01); C12N 5/0636 (2013.01); C12N 15/00 (2013.01); C07K 2317/31 (2013.01); C07K 2317/622 (2013.01); C07K 2319/02 (2013.01); C07K 2319/10 (2013.01); C07K 2319/74 (2013.01); C12N 2501/515 (2013.01); C12N 2501/599 (2013.01); C12N 2510/00 (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,676,980 A | 6/1987 | Segal et al. |
| 4,716,111 A | 12/1987 | Osband et al. |
| 4,816,567 A | 3/1989 | Cabilly et al. |
| 5,199,942 A | 4/1993 | Gillis et al. |
| 5,225,539 A | 7/1993 | Winter |
| 5,229,275 A | 7/1993 | Goroff et al. |
| 5,350,674 A | 9/1994 | Boenisch et al. |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,573,905 A | 11/1996 | Lerner et al. |
| 5,585,089 A | 12/1996 | Queen et al. |
| 5,585,362 A | 12/1996 | Wilson et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,731,168 A | 3/1998 | Carter et al. |

(Continued)

FOREIGN PATENT DOCUMENTS

| | | |
|---|---|---|
| AU | 2006265108 A1 | 1/2007 |
| EP | 519596 A1 | 12/1992 |

(Continued)

OTHER PUBLICATIONS

Kakarla, et al. (2014) "CAR T cells for solid tumors: armed and ready to go?", Cancer Journal, 20(2): 151-55, provided here by way of NIH public access author manuscript, 11 pages long. (Year: 2014).*

(Continued)

Primary Examiner — Robert M Kelly
(74) Attorney, Agent, or Firm — Saul Ewing LLP; Kathryn Doyle

(57) ABSTRACT

The present invention includes compositions and methods for modifying a T cell with a nucleic acid encoding a switch molecule comprising an extracellular domain comprising a membrane receptor or fragment thereof and an intracellular domain comprising a signaling receptor or fragment thereof. In one aspect, a method comprises introducing a nucleic acid encoding a switch molecule and a nucleic acid encoding a soluble fusion protein and/or a nucleic acid encoding a bispecific antibody into a population of cells comprising T cells, wherein the T cells transiently expresses the switch molecule and soluble fusion protein or bispecific antibody. In other aspect, compositions of T cells and methods of treating a disease or condition, such as cancer or an autoimmune disease, are also included.

21 Claims, 24 Drawing Sheets

Specification includes a Sequence Listing.

(56) References Cited

U.S. PATENT DOCUMENTS

| | | | |
|---|---|---|---|
| 5,814,318 | A | 9/1998 | Lonberg et al. |
| 5,939,598 | A | 8/1999 | Kucherlapati et al. |
| 6,120,766 | A | 9/2000 | Hale et al. |
| 6,331,415 | B1 | 12/2001 | Cabilly et al. |
| 6,548,640 | B1 | 4/2003 | Winter |
| 7,585,960 | B2 | 9/2009 | Hanke et al. |
| 8,147,834 | B2 | 4/2012 | Wu |
| 9,073,968 | B2 | 7/2015 | Nishimura et al. |
| 9,315,559 | B2 | 4/2016 | Spencer et al. |
| 9,688,740 | B2 | 6/2017 | Choi |
| 10,584,158 | B2 | 3/2020 | Valdes |
| 2006/0025576 | A1 | 2/2006 | Miller et al. |
| 2009/0055944 | A1 | 2/2009 | Korman et al. |
| 2011/0280878 | A1 | 11/2011 | Honjo et al. |
| 2014/0050709 | A1 | 2/2014 | Leen et al. |
| 2014/0219975 | A1 | 8/2014 | June et al. |
| 2020/0140520 | A1 | 5/2020 | Vera Valdes |

FOREIGN PATENT DOCUMENTS

| | | |
|---|---|---|
| EP | 592106 A1 | 4/1994 |
| EP | 239400 B1 | 8/1994 |
| EP | 3207147 | 8/2017 |
| WO | 9109967 A1 | 7/1991 |
| WO | 9308829 A1 | 5/1993 |
| WO | 9633735 A1 | 10/1996 |
| WO | 9634096 A1 | 10/1996 |
| WO | 9824893 A2 | 6/1998 |
| WO | 2009089004 A1 | 7/2009 |
| WO | 2013019615 A2 | 2/2013 |
| WO | 2014011988 A2 | 1/2014 |
| WO | 2014165707 A2 | 10/2014 |
| WO | 2014172584 A1 | 10/2014 |
| WO | 2015009604 A1 | 1/2015 |
| WO | 2016061574 A1 | 4/2016 |
| WO | 2016122738 | 8/2016 |

OTHER PUBLICATIONS

Morgan, et al. (2010) "Case Report of a Serious Adverse Event Following the Administration of T Cells Transduced With a Chimeric Antigen Receptor Recognizing ERBB2", Molecular Therapy, 18(4): 843-51. (Year: 2010).*
Yang, et al. (2022) "CAR-T Cell Therapy for Breast Cancer: From Basic Research to Clinical Application", International Journal of Biological Sciences 2609-26. (Year: 2022).*
Scalea, et al. (2012) "T-cell-mediated immunological barriers to xenotransplantation" Xenotransplantation, 19: 23-30. (Year: 2012).*
Wang, et al. (Mar. 14, 2017) "Mechanism of immune evasion in breast cancer", OncoTargets and Therapy, 10: 1561-73. (Year: 2017).*
European Office Action issued in EP15880617.4, dated Nov. 13, 2020, 5 pages.
Supplementary European Search Report dated Jun. 20, 2018 for European Patent Application No. 15880617.4.
Examination report dated Mar. 31, 2021 for Australian Patent Application No. 2015380397.
Sims, et al., "A humanized CD18 antibody can block function without cell destruction", J. Immunol., 151:2296-2308 (1993).
Stepinski, et al., "Synthesis and propertys of mRNAs containing the novel "anti-reverse" cap analogs 7-methyl(3'-O-methyl) GpppG and 7-methyl(3'-deoxy)GpppG", 2001, RNA, 7:1468-95.
Studnicka, et al., "Human-engineered monoclonal antibodies retain full specific binding activity by preserving non-CDR complementarity-modulating residues", Protein Engineering, 7(6):805-814 (1994).
Traunecker, et al., "Bispecific single chain molecules (Janusins) target cytotoxic lymphocytes on HIV infected cells", EMBO J. 10: 3655-9 (1991).
Tutt, et al., "Trispecific F(ab')3 derivatives that use cooperative signaling via the TCR/CD3 complex and CD2 to activate and redirect resting cytotoxic T cells", J. Immunol. 147: 60-9 (1991) (abstract).

Vaughan, et al., "Human antibodies with sub-nanomolar affinities isolated from a large non-immunized phage display library.", Vaughan et al., 1996, Nature Biotech., 14:309-14 (Abstract).
Verhoeyen, et al., "Reshaping human antibodies: grafting an antilysozyme activity", Science, 239:1534-1536 (1988).
Watanabe, et al., "A distinct role for ICOS-mediated co-stimulatory signaling in CD4+ and CD8+ T cell subsets.", 2005, International Immunology 17(3):269-278.
Wu, et al., "Humanization of a murine monoclonal antibody by simultaneous optimization of framework and CDR residues.", J. Mol. Biol., 294:151-162 (1999).
European Patent Application No. 15880617.4—Communication pursuant to Article 94(3) EPC issued Jul. 3, 2019.
European Search Report dated Jun. 27, 2018 for European Patent Application No. 15880617.
International Search Report and Written Opinion dated Feb. 26, 2016 for PCT/US15/58192.
Japanese Patent Application No. 2017-540269—First Notice of Reasons for Rejection issued Nov. 8, 2019.
Aoki, "Transforming growth factor beta (TGF-beta) and autoimmunity.", 2005, Autoimmunity Reviews 4:450-459.
Bierer, et al., "Cyclosporin A and FK506: molecular mechanisms of immunosuppression and probes for transplantation biology.", Current Opinion in Immunology 1993, 5:763-773.
Bird, et al., "Single-Chain Antigen-Binding Proteins", 1988, Science 242(4877):423-426.
Brennan, et al., "Preparation of bispecific antibodies by chemical recombination of monoclonal immunoglobulin G1 fragments.", Science. Jul. 5, 1985;229(4708):81-3 (Abstract).
Bruggerman, et al., "Designer Mice: The Production of Human Antibody Repertoires in Transgenic Animals.", 1993, Year in Immunol 7:33-40.
Carter, et al., "Humanization of an anti-p185HER2 antibody for human cancer therapy.", 1992, Proc Natl Acad Sci USA 89:4285-4289.
Chothia, et al., "Canonical structures for the hypervariable regions of immunoglobulins.", J Mol Biol. Aug. 20, 1987;196(4):901-17. (Abstract).
Clackson, et al., "Making antibody fragments using phage display libraries", Nature, 352:624-628 (1991) (abstract).
Claus, et al., "CD27 Signaling Increases the Frequency of Regulatory T Cells and Promotes Tumor Growth.", 2012, Cancer Research 72(14):3664-76.
Cougot, et al., "'Cap-tabolism'.", Trends Biochem Sci. Aug. 2004;29(8):436-44. (Abstract).
Donnelly, et al., "Gene Therapy for Cystic Fibrosis Lung Disease: Overcoming the Barriers to Translation to the Clinic.", 2018, Frontiers in Pharmacology 9: article 1381 (8 pages).
Duchosal, et al., "Immunization of hu-PBL-SCID mice and the rescue of human monoclonal Fab fragments through combinatorial libraries.", 1992, Nature 355:258-262.
Dudley, et al., "Generation of tumor-infiltrating lymphocyte cultures for use in adoptive transfer therapy for melanoma patients", J Immunother. Jul.-Aug. 2003;26(4), Jul.-Aug. 2003, 332-342.
Elango, et al., "Optimized transfection of mRNA transcribed from a d(A/T)100 tail-containing vector", Biochim. Biophys. Res. Commun. 330, 2005, 958-966 (abstract only).
Griffiths, et al., "Human anti-self antibodies with high specificity from phage display libraries.", The EMBO Journal vol. 12, No. 2, pp. 725-734, 1993.
Gruber, et al., "Efficient tumor cell lysis mediated by a bispecific single chain antibody expressed in *Escherichia coli*.", J. Immunol., 152:5368-74 (1994) (abstract).
Henderson, et al., "Comparison of the effects of FK-506, cyclosporine A and rapamycin on IL-2 production.", Immun. 73:316-321, 1991.
Hollinger, et al., "'Diabodies': Small bivalent and bispecific antibody fragments.", Proc. Natl. Acad. Sci. USA, 90:6444-6448 (1993).
Hoogenboom, et al., "By-passing immunization. Human antibodies from synthetic repertoires of germline VH gene segments rearranged in vitro", J. Mol. Biol. 227, 1991, 381-388 (Abstract Only).
Huse, "The T-cell-receptor signaling network.", 2009, Cell Science at a Glance, Journal of Cell Science 122 (9):1269-73 (Year 2009).

(56) References Cited

OTHER PUBLICATIONS

Huston, "Protein engineering of antibody binding sites: Recovery of specific activity in an anti-digoxin single-chain Fv analogue produced in *Escherichia coli*.", 1988, Proc. Natl. Acad. Sci. USA 85:5879-5883.
Jakobovits, et al., "Analysis of homozygous mutant chimeric mice: Deletion of the immunoglobulin heavy-chain joining region blocks B-cell development and antibody production", Proc. Natl. Acad. Sci. 90, 1993, 2551-2555.
Jakobovits, et al., "Germ-line transmission and expression of a human-derived yeast artificial chromosome.", 1993, Nature 362:255-258.
Johnson, et al., "Human antibody engineering", Current Opinion in Structural Biology 3:564-571 (1993).
Jones, et al., "Replacing the complementarity-determining regions in a human antibody with those from a mouse", Nature, 321:522-525 (1986).
Kostelny, et al., "Formation of a bispecific antibody by the use of leucine zippers", "Formation of a bispecific antibody by the use of leucine zippers," J. Immunol., vol. 148, No. 5, pp. 1547-1553 (1992), 1992, 1547-1553.
Kusaba, et al., "Interleukin-12-induced Interforon-gamma Production by Human Peripheral Blood T Cells Is Regulated by Mammalian Target of Rapamycin (mTOR).", 2005, J Biol Chem 280(2):1037-1043.
Lee, "4-1BB Signaling Activates the T Cell Factor 1 Effector/beta-Catenin Pathway with Delayed Kinetics via ERK Signaling and Delayed PI3K/AKT Activation to Promote the Proliferation of CD8+ T Cells.", 2013, PLOS One 8(7):e69677 (11 pages).
Liu, et al., "Calcineurin Is a Common Target of Cyclophilin-Cyclosporin A and FKBP-FK506 Complexes", Cell 66:807-815, 1991.
Lonberg, et al., "Human antibodies from transgenic mice.", Int. Rev. Immunol., 13:65-93 (1995).
Marks, et al., "By-passing immunization. Human antibodies from V-gene libraries displayed on phage", J. Mol. Biol. 222:581-597 (1991).
McCafferty, et al., "Phage antibodies: filamentous phage displaying antibody variable domains", Nature 348, 1990, 552-554.
Milstein, et al., "Hybrid hybridomas and their use in immunohistochemistry", (1983) Nature 305: 537-39. (abstract).
Nacheva, et al., "Preventing nondesired RNA-primed RNA extension catalyzed by T7 RNA polymerase", 2003, Eur. J. Biochem., 270:1458-65.
Nishikawa, et al., "Nonviral vectors in the new millennium: delivery barriers in gene transfer.", Hum Gene Ther., 12(8):861-70 (2001) (Abstract).
Oh, et al., "TGF-beta: Guardian of T Cell Function", 2013, J. Immunol. 191:3973-3979.
Padlan, "A possible procedure for reducing the immunogenicity of antibody variable domains while preserving their ligand-binding properties", 1991, Molecular Immunology, 28(4/5):489-498.
Presta, et al., "Humanization of an antibody directed against IgE", J. Immunol., 151:2623-32 (1993).
Redmond, et al., "The role of OX40-mediated co-stimulation in T cell activation and survival.", 2009, Crit Rev Immunol 29(3):187-201.
Riechmann, et al., "Reshaping human antibodies for therapy", Nature, 332:323-327 (1988).
Riechmann, "Single domain antibodies: comparison of camel VH and camelised human VH domains", 1999, Journal of Immunological Methods 231:25-38.
Riha, et al., "CD28 co-signaling in the adaptive immune response.", Landes Bioscience 1(3):231-40 (Year: 2010).
Roder, et al., "The EBV-hybridoma technique", Methods Enzymol., 121:140-167 (1986).
Roguska, et al., "Humanization of murine monoclonal antibodies through variable domain resurfacing", PNAS, 91:969-973 (1994).
Rosenberg, et al., "Use of tumor-infiltrating lymphocytes and interleukin-2 in the immunotherapy of patients with metastatic melanoma. A preliminary report.", New Eng. J. of Med. 319:1676-80, 1988).
Schenborn, et al., "A novel transcription property of SP6 and T7 RNA polymerases: dependence on template structure", 1985, Nuc Acids Res., 13:6223-36.

\* cited by examiner

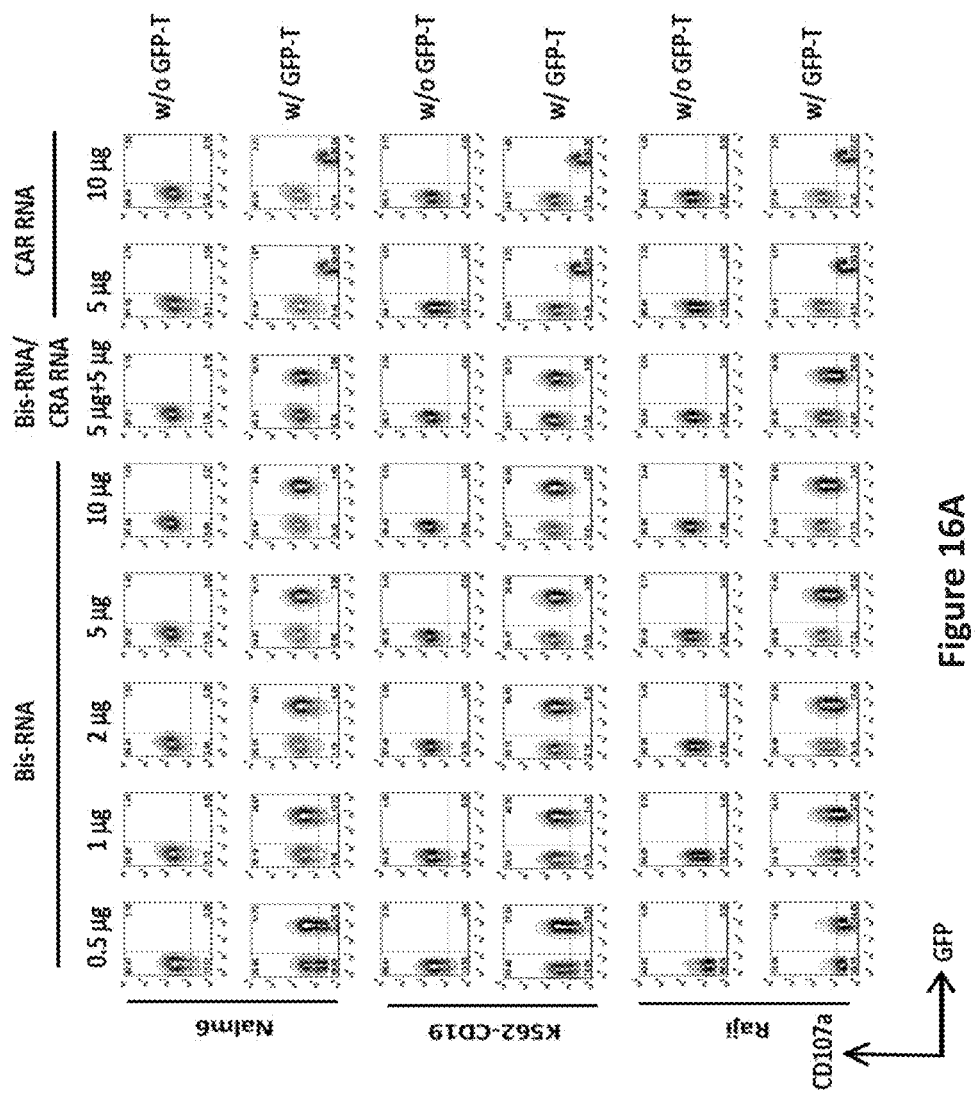

| No | RNA | cd19z | EP |
|---|---|---|---|
| | Test RNAs by co-electroporation | | |
| 1 | 10ug PD-1 | | |
| 2 | 10ug PD-1-CD28 | | |
| 3 | 10ug 10A5-1412 | | |
| 4 | 10ug 1364-1412 | | |
| 5 | 10ug 1B12-1412 | | |
| 6 | 10ug PD1-CD80 | | |
| 7 | 10ug PD1-CD86 | | |
| 8 | 10ug CD80-PD1 | | |
| 9 | 10ug CD86-PD1 | 2ug | Yes |
| 10 | 10ug PDL1-CD80 | | |
| 11 | 10ug PDL1-CD86 | | |
| 12 | 10ug PDL2-CD80 | | |
| 13 | 10ug PDL2-CD86 | | |
| 14 | 10ug CD80-PDL1 | | |
| 15 | 10ug CD80-PDL2 | | |
| 16 | 10ug CD86-PDL1 | | |
| 17 | None | None | |
| 18 | None | None | No |

Figure 17

SEQUENCE LISTING

<160> NUMBER OF SEQ IDS: 17

<210> SEQ ID NO 1
<211> LENGTH: 717
<212> TYPE: DNA
<213> ORGANISM: Homo Sapiens

<400> SEQUENCE: 1
atggaggcgg cggtcgctgc tccgcgtccc cggctgctcc tcctcgtgct ggcggcggcg    60

```
gcggcggcgg cggcggcgct gctcccgggg gcgacggcgt tacagtgttt ctgccacctc    120
tgtacaaaag acaattttac ttgtgtgaca gatgggctct gctttgtctc tgtcacagag    180
accacagaca aagttataca caacagcatg tgtatagctg aaattgactt aattcctcga    240
gataggccgt ttgtatgtgc accctcttca aaaactgggc tgtgactac aacatattgc     300 tgcaatcagg accattgcaa taaaatagaa cttccaacta ctgtaaagtc atcacctggc    360
cttggtcctg tggaactggc agctgtcatt gctggaccag tgtgcttcgt ctgcatctca    420
ctcatgttga tggtctatat cagggccgca cggcacctgt gcccgccgct gcccacaccc    480
tgtgccagct ccgccattga gttccctgga gggaaggaga cttggcagtg gatcaaccca    540
gtggacttcc aggaagaggc atccctgcag gaggccctgg tggtagagat gtcctgggac    600
aaaggcgaga ggactgagcc tctcgagaag acagagctac ctgagggtgc ccctgagctg    660
gccctggata cagagttgtc cttggaggat ggagacaggt gcaaggccaa gatgtga       717

<210> SEQ ID NO 2
<211> LENGTH: 1212
<212> TYPE: DNA
<213> ORGANISM: Homo Sapiens

<400> SEQUENCE: 2
atgggtcggg ggctgctcag gggcctgtgg ccgctgcaca tcgtcctgtg gacgcgtatc     60
gccagcacga tcccaccgca cgttcagaag tcggttaata cgacatgat agtcactgac     120 aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga ggaaaaaaaa aaagcctggt gagacttttct tcatgtgttc ctgtagctct    420
gatgagtgca atgacaacat catcttctca gaagaatata acaccagcaa tcctgacttg    480
ttgctagtca tatttcaagt gacaggcatc agcctcctgc caccactggg agttgccata    540
tctgtcatca tcatcttcta ccagcaaaag gtgtttgttc tcctagcagc cctcagacct    600
cagtggtgta gcagagaaat tccagatcca gcaaatagca cttgcgctaa gaaatatccc    660
attgcagagg agaagacaca gctgcccttg acaggctccc tgatagactg gcccacgcct    720
gaagatcctg aaccgctggt catcagtgaa gtccttcatc aagtgacccc agttttcaga    780
catcccccct gctccaactg gccacaaagg gaaaaaggaa tccaaggtca tcaggcctct    840
gagaaagaca tgatgcacag tgcctcaagc ccaccacctc caagagctct ccaagctgag    900
agcagacaac tggtggatct gtacaaggtg ctggagagca ggggctccga cccaaagcca    960
gaaaacccag cctgtccctg acggtgctcc ccagcaggtg accttcccac ccatgatggc   1020 tacttacccct ccaacataga tgacctcccc tcacatgagg cacctctcgc tgactctctg   1080
gaagaactgg agcctcagca catctccctt tctgttttcc cctcaagttc tcttcaccca   1140
ctcaccttct cctgtggtga taagctgact ctggatcagt taaagatgag gtgtgactcc   1200
ctcatgctct ga                                                       1212

<210> SEQ ID NO 3
<211> LENGTH: 1515
<212> TYPE: DNA
<213> ORGANISM: Homo Sapiens
```

```
<400> SEQUENCE: 3
atgggttggt cctgcatcat cctgtttctc gtggccaccg ccaccggcgt gcactccgaa      60
attgtgttga cacagtctcc agccaccctg tctttgtctc aggggaaaag agccaccctc     120
tcctgcaggg ccagtcagag tgttcgcagc tacttagcct ggtaccaaca gaaacctggc     180
caggctccca ggctcctcat ctatgatgca tccaacaggg ccactggcat cccagccagg     240
ttcagtggca gtgggtctgg gacagacttc actctcacca tcagcagcct agagcctgaa     300
gattttgcag tttattactg tcagcagcgt agcaactggc ctccgacgtt cggccaaggg     360
accaaggtgg aaatcaaaag tggagggggc ggttcacagc tgcaggtgca ggagtcgggc     420
ccaggactgg tgaagccttc ggagaccctg tccctcacct gcactgtctc tggtggctcc     480
atcagcaaca gttatttctc ctggggctgg atccgccagc ccccagggaa gggactggag     540
tggattggga gtttctatta tggtgaaaaa acctactaca cccgtccct caagagccga     600 gccaccatat ccattgacac gtccaagagc cagttctccc tgaagctgag ctctgtgacc     660
gccgcagaca cggctgtgta ttactgtccg agagggccta ctatgattcg ggagttata      720 gactcctggg gccagggaac ctggtgacg tgtcgtcgg ggggcggggg gagtcaggtg      780
cagctggtgc agtccggagc cgaggtaaag aagccaggcg cttccgtcaa ggtgtcatgc     840
aaggcctcag gctacacctt cacaagctat tacatccact gggtgcgcca agctcccggt     900
cagggcttgg agtggatcgg gtgcatttac ccagggaacg tcaacacaaa ctacaacgag     960
aagttcaagg atcgggcaac cctgaccgtg acacatcca tctctaccgc ctacatggag    1020
ctgtcacgcc tgcgctctga tgacaccgca gtgtacttct gtaccaggag tcactacggc    1080
ctggactgga actttgatgt ctggggccag ggaaccaccg tgacggtgtc cagtgtggag    1140 ggcgtagtg gcggctctgg tgggtccgga ggctcaggcg gcgtgatgga tgacattcag    1200
atgacccaga gtccctcctc cctctccgct tccgtcggag accgcgtgac catcacttgt    1260
cacgcctcac agaatatcta cgtgtggctg aactggtacc aacagaagcc cggcaaggcc    1320
cccaagctgc ttatctataa agcgtccaac ctccacacgg gagtcccttc ccgcttctcc    1380
ggatccggca gtgggacgga cttcacactc acaatctcgt cgctgcagcc agaggacttt    1440
gcgacgtact actgccagca gggccagacc tacccatata ctttcggcgg cgggaccaag    1500
gtggagatta agtaa                                                      1515

<210> SEQ ID NO 4
<211> LENGTH: 1515
<212> TYPE: DNA
<213> ORGANISM: Homo Sapiens

<400> SEQUENCE: 4
atgggttggt cctgcatcat cctgtttctc gtggccaccg ccaccggcgt gcactccgaa      60
attgtgttga cacagtctcc agccaccctg tctttgtctc aggggaaaag agccaccctc     120
tcctgcaggg ccagtcagag tgttagaagt ttcttagcct ggtaccaaca gaaacctggc     180
caggctccca ggctcctcat ctatgatgca tccaacaggg ccactggcat cccagccagg     240
ttcagtggca gtgggtctg gacagactt cactctcacc atcagcagcc tagagcctga      300
agattttgca gtttattact gtcagcagcg tagcaactgg cctccgacgt cggccaagg      360 gaccaaggtg gaaatcaaaa gtggagggggc cggttcacag ctacagctgc aggagtcggg     420
cccaggactg gtgaagcctt cggagaccct atccctcacc tgcactgtct ctggtggctc     480
catcagcagt agtagttact cctggggctg gatccgccag cccccaggga agggcctgga     540
```

```
gtggattgga gtttctatta cagtgggatc acctactaca gcccgtccct caagagtcga      600
attatcatat ccgaagacac gtccaagaac cagttctccc tgaagctgag ttctgtgacc      660
gccgcagaca cggctgtgta ttactgtgcg agcgggttta ctatgattcg gggagccctt      720
gactactggg gccagggaac cctggtgacg gtgtcgtcgg ggggcggggg gagtcaggtg      780
cagctggtgc agtccggagc cgaggtaaag aagccaggcg cttccgtcaa ggtgtcatgc      840
aaggcctcag gctacacctt cacaagctat tacatccact gggtgcgcca agctcccggt      900
cagggcttgg agtggatcgg gtgcatttac ccagggaacg tcaacacaaa ctacaacgag      960
aagttcaagg atcgggcaac cctgaccgtg acacatccaa tctctaccgc ctacatggag     1020
ctgtcacgcc tgcgctctga tgacaccgca gtgtacttct gtaccaggag tcactacggc     1080
ctggactgga actttgatgt ctggggccag gaaccaccgt gacggtgtc cagtgtggag      1140 ggcggtagtg gcggctctgg tgggtccgga ggctcaggcg gcgtgatgga tgacattcag     1200
atgacccaga gtccctcctc cctctccgct tccgtcggag accgcgtgac catcacttgt     1260
cacgcctcac agaatatcta cgtgtggctg aactggtacc aacagaagcc cggcaaggcc     1320
cccaagctgc ttatctataa agcgtccaac ctccacacgg gagtcccttc ccgcttctcc     1380
ggatccggca gtgggacgga cttcacactc acaatctcgt cgctgcagcc agaggacttt     1440
gcgacgtact actgccagca gggccagacc tacccatata cttcggcgg cgggaccaag     1500 gtggagatta agtaa                                                      1515

<210> SEQ ID NO 5
<211> LENGTH: 1449
<212> TYPE: DNA
<213> ORGANISM: Homo Sapiens

<400> SEQUENCE: 5
atggatcccc agtgcactat gggactgagt aacattctct ttgtgatggc cttcctgctc       60
tctggtgctg ctcctctgaa gattcaagct tatttcaatg agactgcaga cctgccatgc      120
caatttgcaa actctcaaaa ccaaagcctg agtgagctag tagtattttg gcaggaccag      180
gaaaacttgg ttctgaatga ggtatactta ggcaaagaga aatttgacag tgttcattcc      240
aagtatatgg gccgcacaag ttttgattcg gacagttgga ccctgagact tcacaatctt      300
cagatcaagg acaagggctt gtatcaatgt atcatccatc acaaaaagcc cacaggaatg      360
attcgcatcc accagatgaa ttctgaactg tcagtgcttg ctaacttcag tcaacctgaa      420
atagtaccaa tttctaatat aacagaaaat gtgtacataa atttgacctg ctcatctata      480
cacggttacc cagaacctaa gaagatgagt gttttgctaa gaaccaagaa ttcaactatc      540
gagtatgatg gtattatgca gaaatctcaa gataatgtca cagaactgta cgacgtttcc      600
atcagcttgt ctgtttcatt ccctgatgtt acgagcaata tgaccatctt ctgtattctg      660
gaaactgaca gacgcggct tttatcttca cctttctcta tagagcttga ggaccctcag      720
cctcccccag accacattcc tggcggaggg ggaagtggcg ggggtgggtc cggcggcggc      780
ggctcgttta ctgtcacggt tcccaaggac ctatatgtgg tagagtatgg tagcaatatg      840
acaattgaat gcaaattccc agtagaaaaa caattagacc tggctgcact aattgtctat      900
tgggaaatgg aggataagaa cattattcaa tttgtgcatg agaggaaga cctgaaggtt      960 cagcatagta gctacagaca gagggcccgg ctgttgaagg accagctctc cctgggaaat     1020
gctgcacttc agatcacaga tgtgaaattg caggatgcag gggtgtaccg ctgcatgatc     1080
```

| | |
|---|---|
| agctatggtg gtgccgacta caagcgaatt actgtgaaag tcaatgcccc atacaacaaa | 1140 |
| atcaaccaaa gaattttggt tgtggatcca gtcacctctg aacatgaact gacatgtcag | 1200 |
| gctgagggct accccaaggc cgaagtcatc tggacaagca gtgaccatca agtcctgagt | 1260 |
| ggtaagacca ccaccaccaa ttccaagaga gaggagaagc ttttcaatgt gaccagcaca | 1320 |
| ctgagaatca acacaacaac taatgagatt ttctactgca cttttaggag attagatcct | 1380 |
| gaggaaaacc atacagctga attggtcatc ccagaactac ctctggcaca tcctccaaat | 1440 |
| gaaaggtaa | 1449 |

<210> SEQ ID NO 6
<211> LENGTH: 1392
<212> TYPE: DNA
<213> ORGANISM: Homo Sapiens

<400> SEQUENCE: 6

| | |
|---|---|
| atggatcccc agtgcactat gggactgagt aacattctct ttgtgatggc cttcctgctc | 60 |
| tctggtgctg ctcctctgaa gattcaagct tatttcaatg agactgcaga cctgccatgc | 120 |
| caatttgcaa actctcaaaa ccaaagcctg agtgagctag tagtattttg gcaggaccag | 180 |
| gaaaacttgg ttctgaatga ggtatactta ggcaaagaga aatttgacag tgttcattcc | 240 |
| aagtatatgg gccgcacaag ttttgattcg gacagttgga ccctgagact tcacaatctt | 300 |
| cagatcaagg acaagggctt gtatcaatgt atcatccatc acaaaaagcc cacaggaatg | 360 |
| attcgcatcc accagatgaa ttctgaactg tcagtgcttg ctaacttcag tcaacctgaa | 420 |
| atagtaccaa tttctaatat aacagaaaat gtgtacataa atttgacctg ctcatctata | 480 |
| cacggttacc cagaacctaa gaagatgagt gttttgctaa gaaccaagaa ttcaactatc | 540 |
| gagtatgatg gtattatgca gaaatctcaa gataatgtca cagaactgta cgacgtttcc | 600 |
| atcagcttgt ctgtttcatt ccctgatgtt acgagcaata tgaccatctt ctgtattctg | 660 |
| gaaactgaca gacgcggct tttatcttca cctttctcta tagagcttga ggaccctcag | 720 |
| cctcccccag accacattcc tggcggaggg ggaagtggcg ggggtgggtc cggcggcggc | 780 |
| ggctcgttat tcacagtgac agtccctaag gaactgtaca ataagagca tggcagcaat | 840 |
| gtgaccctgg aatgcaactt tgacactgga agtcatgtga accttggagc aataacagcc | 900 |
| agtttgcaaa aggtggaaaa tgatacatcc ccacaccgtg aaagagccac tttgctggag | 960 |
| gagcagctgc ccctagggaa ggcctcgttc acatacctc aagtccaagt gagggacgaa | 1020 |
| ggacagtacc aatgcataat catctatggg gtcgcctggg actacaagta cctgactctg | 1080 |
| aaagtcaaag cttcctacag gaaaataaac actcacatcc taaggttcc agaaacagat | 1140 |
| gaggtagagc tcacctgcca ggctacaggt tatcctctgg cagaagtatc ctggccaaac | 1200 |
| gtcagcgttc ctgccaacac cagccactcc aggacccctg aaggcctcta ccaggtcacc | 1260 |
| agtgttctgc gcctaaagcc accccctggc agaaacttca gctgtgtgtt ctggaatact | 1320 |
| cacgtgaggg aacttacttt ggccagcatt gaccttcaaa gtcagatgga acccaggacc | 1380 |
| catccaactt aa | 1392 |

<210> SEQ ID NO 7
<211> LENGTH: 1434
<212> TYPE: DNA
<213> ORGANISM: Homo Sapiens

<400> SEQUENCE: 7

| | |
|---|---|
| atgggccaca cacggaggca gggaacatca ccatccaagt gtccatacct caatttcttt | 60 |

```
cagctcttgg tgctggctgg tctttctcac ttctgttcag gtgttatcca cgtgaccaag      120
gaagtgaaag aagtggcaac gctgtcctgt ggtcacaatg tttctgttga agagctggca      180
caaactcgca tctactggca aaaggagaag aaaatggtgc tgactatgat gtctggggac      240
atgaatatat ggcccgagta caagaaccgg accatctttg atatcactaa taacctctcc      300
attgtgatcc tggctctgcg cccatctgac gagggcacat acgagtgtgt tgttctgaag      360
tatgaaaaag acgctttcaa gcgggaacac ctggctgaag tgacgttatc agtcaaagct      420
gacttcccta cacctagtat atctgacttt gaaattccaa cttctaatat tagaaggata      480
atttgctcaa cctctggagg ttttccagag cctcacctct cctggttgga aaatggagaa      540
gaattaaatg ccatcaacac aacagtttcc caagatcctg aaactgagct ctatgctgtt      600
agcagcaaac tggatttcaa tatgacaacc aaccacagct tcatgtgtct catcaagtat      660
ggacatttaa gagtgaatca gaccttcaac tggaatacaa ccaagcaaga gcattttcct      720
gataacggcg aggggggaag tggcgggggt gggtccggcg gcggcggctc gtttactgtc      780
acggttccca aggacctata tgtggtagag tatggtagca atatgacaat tgaatgcaaa      840
ttcccagtag aaaaacaatt agacctggct gcactaattg tctattggga aatggaggat      900
aagaacatta ttcaatttgt gcatggagag gaagacctga aggttcagca gtagctac      960 agacagaggg cccggctgtt gaaggaccag ctctccctgg gaaatgctgc acttcagatc     1020
acagatgtga aattgcagga tgcaggggtg taccgctgca tgatcagcta tggtggtgcc     1080
gactacaagc gaattactgt gaaagtcaat gccccataca caaaatcaa ccaaagaatt     1140 ttggttgtgg atccagtcac ctctgaacat gaactgacat gtcaggctga gggctacccc     1200
aaggccgaag tcatctggac aagcagtgac catcaagtcc tgagtggtaa gaccaccacc     1260
accaattcca agagagagga gaagcttttc aatgtgacca gcacactgag aatcaacaca     1320
acaactaatg agattttcta ctgcactttt aggagattag atcctgagga aaaccataca     1380
gctgaattgg tcatcccaga actacctctg gcacatcctc caaatgaaag gtaa           1434

<210> SEQ ID NO 8
<211> LENGTH: 1377
<212> TYPE: DNA
<213> ORGANISM: Homo Sapiens

<400> SEQUENCE: 8
atgggccaca cacggaggca gggaacatca ccatccaagt gtccatacct caatttcttt       60
cagctcttgg tgctggctgg tctttctcac ttctgttcag gtgttatcca cgtgaccaag      120
gaagtgaaag aagtggcaac gctgtcctgt ggtcacaatg tttctgttga agagctggca      180
caaactcgca tctactggca aaaggagaag aaaatggtgc tgactatgat gtctggggac      240
atgaatatat ggcccgagta caagaaccgg accatctttg atatcactaa taacctctcc      300
attgtgatcc tggctctgcg cccatctgac gagggcacat acgagtgtgt tgttctgaag      360
tatgaaaaag acgctttcaa gcgggaacac ctggctgaag tgacgttatc agtcaaagct      420
gacttcccta cacctagtat atctgacttt gaaattccaa cttctaatat tagaaggata      480
atttgctcaa cctctggagg ttttccagag cctcacctct cctggttgga aaatggagaa      540
gaattaaatg ccatcaacac aacagtttcc caagatcctg aaactgagct ctatgctgtt      600
agcagcaaac tggatttcaa tatgacaacc aaccacagct tcatgtgtct catcaagtat      660
ggacatttaa gagtgaatca gaccttcaac tggaatacaa ccaagcaaga gcattttcct      720
```

| | |
|---|---:|
| gataacggcg gaggggggaag tggcgggggt gggtccggcg gcggcggctc gttattcaca | 780 |
| gtgacagtcc ctaaggaact gtacataata gagcatggca gcaatgtgac cctggaatgc | 840 |
| aactttgaca ctggaagtca tgtgaacctt ggagcaataa cagccagttt gcaaaaggtg | 900 |
| gaaaatgata catccccaca ccgtgaaaga gccactttgc tggaggagca gctgcccta | 960 |
| gggaaggcct cgttccacat acctcaagtc caagtgaggg acgaaggaca gtaccaatgc | 1020 |
| ataatcatct atggggtcgc ctgggactac aagtacctga ctctgaaagt caaagcttcc | 1080 |
| tacaggaaaa taaacactca catcctaaag gttccagaaa cagatgaggt agagctcacc | 1140 |
| tgccaggcta caggttatcc tctggcagaa gtatcctggc caaacgtcag cgttcctgcc | 1200 |
| aacaccagcc actccaggac ccctgaaggc ctctaccagg tcaccagtgt tctgcgccta | 1260 |
| aagccacccc ctggcagaaa cttcagctgt gtgttctgga atactcacgt gagggaactt | 1320 |
| actttggcca gcattgacct tcaaagtcag atggaaccca ggacccatcc aacttaa | 1377 |

<210> SEQ ID NO 9
<211> LENGTH: 1440
<212> TYPE: DNA
<213> ORGANISM: Homo Sapiens

<400> SEQUENCE: 9

| | |
|---|---:|
| atgaggatat ttgctgtctt tatattcatg acctactggc atttgctgaa cgcatttact | 60 |
| gtcacggttc ccaaggacct atatgtggta gagtatggta gcaatatgac aattgaatgc | 120 |
| aaattcccag tagaaaaaca attagacctg gctgcactaa ttgtctattg ggaaatggag | 180 |
| gataagaaca ttattcaatt tgtgcatgga gaggaagacc tgaaggttca gcatagtagc | 240 |
| tacagacaga gggcccggct gttgaaggac cagctctccc tgggaaatgc tgcacttcag | 300 |
| atcacagatg tgaaattgca ggatgcaggg gtgtaccgct gcatgatcag ctatggtggt | 360 |
| gccgactaca agcgaattac tgtgaaagtc aatgccccat acaacaaaat caaccaaaga | 420 |
| attttggttg tggatccagt cacctctgaa catgaactga catgtcaggc tgagggctac | 480 |
| cccaaggccg aagtcatctg acaagcagt gaccatcaag tcctgagtgg taagaccacc | 540 |
| accaccaatt ccaagagaga ggagaagctt ttcaatgtga ccagcacact gagaatcaac | 600 |
| acaacaacta atgagatttt ctactgcact tttaggagat tagatcctga ggaaaaccat | 660 |
| acagctgaat tggtcatccc agaactacct ctggcacatc ctccaaatga agggggcgga | 720 |
| gggggaagtg gcggggggtgg gtccggcggc ggcggctcgg gtgctgctcc tctgaagatt | 780 |
| caagcttatt tcaatgagac tgcagacctg ccatgccaat ttgcaaactc tcaaaaccaa | 840 |
| agcctgagtg agctagtagt attttggcag gaccaggaaa acttggttct gaatgaggta | 900 |
| tacttaggca aagagaaatt tgacagtgtt cattccaagt atatgggccg cacaagtttt | 960 |
| gattcggaca gttggaccct gagacttcac aatcttcaga tcaaggacaa gggcttgtat | 1020 |
| caatgtatca tccatcacaa aaagcccaca ggaatgattc gcatccacca gatgaattct | 1080 |
| gaactgtcag tgcttgctaa cttcagtcaa cctgaaatag taccaatttc taatataaca | 1140 |
| gaaaatgtgt acataaattt gacctgctca tctatacacg gttacccaga acctaagaag | 1200 |
| atgagtgttt tgctaagaac caagaattca actatcgagt atgatggtat tatgcagaaa | 1260 |
| tctcaagata atgtcacaga actgtacgac gtttccatca gcttgtctgt ttcattccct | 1320 |
| gatgttacga gcaatatgac catcttctgt attctggaaa ctgacaagac gcggcttta | 1380 |
| tcttcacctt tctctataga gcttgaggac cctcagcctc ccccagacca cattccttaa | 1440 |

```
<210> SEQ ID NO 10
<211> LENGTH: 1408
<212> TYPE: DNA
<213> ORGANISM: Homo Sapiens

<400> SEQUENCE: 10
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca agcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg acaagcagt gaccatcaag tcctgagtgg taagaccacc     540
accaccaatt ccaagagaga ggagaagctt ttcaatgtga ccagcacact gagaatcaac     600
acaacaacta tgagattttt ctactgcact tttaggagat tagatcctga ggaaaaccat     660
acagctgaat tggtcatccc agaactacct ctggcacatc ctccaaatga aggggcgga      720 ggggaagtg gcggggtgg gtccggcggc ggcggctcgt cttctctcact tctgttcagg     780 tgttatccac gtgaccaagg aagtgaaaga agtggcaacg ctgtcctgtg gtcacaatgt     840
ttctgttgaa gagctggcac aaactcgcat ctactggcaa aaggagaaga aaatggtgct     900
gactatgatg tctggggaca tgaatatatg gcccgagtac aagaaccgga ccatctttga     960
tatcactaat aacctctcca ttgtgatcct ggctctgcgc ccatctgacg agggcacata    1020
cgagtgtgtt gttctgaagt atgaaaaaga cgctttcaag cgggaacacc tggctgaagt    1080
gacgttatca gtcaaagctg acttccctac acctagtata tctgactttg aaattccaac    1140
ttctaatatt agaaggataa tttgctcaac ctctggaggt tttccagagc ctcacctctc    1200
ctggttggaa aatggagaag aattaaatgc catcaacaca acagtttccc aagatcctga    1260
aactgagctc tatgctgtta gcagcaaact ggatttcaat atgacaacca accacagctt    1320
catgtgtctc atcaagtatg gacatttaag agtgaatcag accttcaact ggaatacaac    1380
caagcaagag catttttcctg ataactaa                                       1408

<210> SEQ ID NO 11
<211> LENGTH: 1383
<212> TYPE: DNA
<213> ORGANISM: Homo Sapiens

<400> SEQUENCE: 11
atgatcttcc tcctgctaat gttgagcctg gaattgcagc ttcaccagat agcagcttta      60
ttcacagtga cagtccctaa ggaactgtac ataatagagc atggcagcaa tgtgaccctg     120
gaatgcaact ttgacactgg aagtcatgtg aaccttggag caataacagc cagtttgcaa     180
aaggtggaaa atgatacatc cccacaccgt gaaagagcca ctttgctgga ggagcagctg     240
cccctaggga aggcctcgtt ccacatacct caagtccaag tgagggacga aggacagtac     300
caatgcataa tcatctatgg ggtcgcctgg gactacaagt acctgactct gaaagtcaaa     360
gcttcctaca ggaaaataaa cactcacatc ctaaaggttc cagaaacaga tgaggtagag     420
ctcacctgcc aggctacagg ttatcctctg gcagaagtat cctggccaaa cgtcagcgtt     480
```

```
cctgccaaca ccagccactc caggaccoct gaaggcctct accaggtcac cagtgttctg    540
cgcctaaagc cacccctgg cagaaacttc agctgtgtgt tctggaatac tcacgtgagg    600
gaacttactt tggccagcat tgaccttcaa agtcagatgg aacccaggac ccatccaact    660
ggcggagggg gaagtggcgg gggtgggtcc ggcggcggcg gctcgggtgc tgctcctctg    720
aagattcaag cttatttcaa tgagactgca gacctgccat gccaatttgc aaactctcaa    780
aaccaaagcc tgagtgagct agtagtattt tggcaggacc aggaaaactt ggttctgaat    840
gaggtatact taggcaaaga gaaatttgac agtgttcatt ccaagtatat gggccgcaca    900
agttttgatt cggacagttg gaccctgaga cttcacaatc ttcagatcaa ggacaagggc    960
ttgtatcaat gtatcatcca tcacaaaaag cccacaggaa tgattcgcat ccaccagatg   1020
aattctgaac tgtcagtgct tgctaacttc agtcaacctg aaatagtacc aatttctaat   1080
ataacagaaa atgtgtacat aaatttgacc tgctcatcta tacacggtta cccagaacct   1140
aagaagatga gtgttttgct aagaaccaag aattcaacta tcgagtatga tggtattatg   1200
cagaaatctc aagataatgt cacagaactg tacgacgttt ccatcagctt gtctgtttca   1260
ttccctgatg ttacgagcaa tatgaccatc ttctgtattc tggaaactga caagacgcgg   1320 ctttatctt caccttctc tatagagctt gaggaccctc agcctccccc agaccacatt   1380
cct                                                                 1383

<210> SEQ ID NO 12
<211> LENGTH: 254
<212> TYPE: PRT
<213> ORGANISM: Artificial Sequence
<220> FEATURE:
<223> OTHER INFORMATION: vector

<400> SEQUENCE: 12

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
                20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
                100                 105                 110

Trp Pro Thr Phe Gly Gln Gly Thr Lys Val Glu Ile Lys Ser Gly Gly
            115                 120                 125

Gly Gly Ser Gln Val Gln Leu Val Gln Ser Gly Ala Glu Val Lys Lys
        130                 135                 140

Pro Gly Ser Ser Val Lys Val Ser Cys Lys Thr Ser Gly Asp Thr Phe
145                 150                 155                 160

Ser Thr Tyr Ala Ile Ser Trp Val Arg Gln Ala Pro Gly Gln Gly Leu
                165                 170                 175

Glu Trp Met Gly Gly Ile Ile Pro Ile Phe Gly Lys Ala His Tyr Ala
            180                 185                 190

Gln Lys Phe Gln Gly Arg Val Thr Ile Thr Ala Asp Glu Ser Thr Ser
```

```
                195                 200                 205
Thr Ala Tyr Met Glu Leu Ser Ser Leu Arg Ser Glu Asp Thr Ala Val
    210                 215                 220
Tyr Phe Cys Ala Arg Lys Phe His Phe Val Ser Gly Ser Pro Phe Gly
225                 230                 235                 240
Met Asp Val Trp Gly Gln Gly Thr Thr Val Thr Val Ser Ser
                245                 250
```

<210> SEQ ID NO 13
<211> LENGTH: 253
<212> TYPE: PRT
<213> ORGANISM: Artificial Sequence
<220> FEATURE:
<223> OTHER INFORMATION: vector

<400> SEQUENCE: 13

```
Met Gly Trp Ser Cys Ile Ile Leu Phe Leu Val Ala Thr Ala Thr Gly
1               5                   10                  15
Val His Ser Ala Ile Gln Leu Thr Gln Ser Pro Ser Ser Leu Ser Ala
                20                  25                  30
Ser Val Gly Asp Arg Val Thr Ile Thr Cys Arg Ala Ser Gln Gly Ile
            35                  40                  45
Ser Ser Ala Leu Ala Trp Tyr Gln Gln Lys Pro Gly Lys Ala Pro Lys
50                  55                  60
Leu Leu Ile Tyr Asp Ala Ser Ser Leu Glu Ser Gly Val Pro Ser Arg
65                  70                  75                  80
Phe Ser Gly Ser Gly Ser Gly Thr Asp Phe Thr Leu Thr Ile Ser Ser
                85                  90                  95
Leu Gln Pro Glu Asp Phe Ala Thr Tyr Tyr Cys Gln Gln Phe Asn Ser
            100                 105                 110
Tyr Pro Phe Thr Phe Gly Pro Gly Thr Lys Val Asp Ile Lys Ser Gly
            115                 120                 125
Gly Gly Gly Ser Glu Val Gln Leu Val Glu Ser Gly Gly Gly Leu Val
        130                 135                 140
Gln Pro Gly Arg Ser Leu Arg Leu Ser Cys Ala Ala Ser Gly Ile Thr
145                 150                 155                 160
Phe Asp Asp Tyr Gly Met His Trp Val Arg Gln Ala Pro Gly Lys Gly
                165                 170                 175
Leu Glu Trp Val Ser Gly Ile Ser Trp Asn Arg Gly Arg Ile Glu Tyr
                180                 185                 190
Ala Asp Ser Val Lys Gly Arg Phe Thr Ile Ser Arg Asp Asn Ala Lys
            195                 200                 205
Asn Ser Leu Tyr Leu Gln Met Asn Ser Leu Arg Ala Glu Asp Thr Ala
    210                 215                 220
Leu Tyr Tyr Cys Ala Lys Gly Arg Phe Arg Tyr Phe Asp Trp Phe Leu
225                 230                 235                 240
Asp Tyr Trp Gly Gln Gly Thr Leu Val Thr Val Ser Ser
                245                 250
```

<210> SEQ ID NO 14
<211> LENGTH: 254
<212> TYPE: PRT
<213> ORGANISM: Artificial Sequence
<220> FEATURE:
<223> OTHER INFORMATION: vector

<400> SEQUENCE: 14

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Thr Phe Gly Gln Gly Thr Lys Val Glu Ile Lys Ser Gly Gly
        115                 120                 125

Gly Gly Ser Gln Val Gln Leu Val Gln Ser Gly Ala Glu Val Lys Lys
    130                 135                 140

Pro Gly Ser Ser Val Lys Val Ser Cys Lys Thr Ser Gly Asp Thr Phe
145                 150                 155                 160

Ser Ser Tyr Ala Ile Ser Trp Val Arg Gln Ala Pro Gly Gln Gly Leu
                165                 170                 175

Glu Trp Met Gly Gly Ile Ile Pro Ile Phe Gly Arg Ala His Tyr Ala
            180                 185                 190

Gln Lys Phe Gln Gly Arg Val Thr Ile Thr Ala Asp Glu Ser Thr Ser
        195                 200                 205

Thr Ala Tyr Met Glu Leu Ser Ser Leu Arg Ser Glu Asp Thr Ala Val
210                 215                 220

Tyr Phe Cys Ala Arg Lys Phe His Phe Val Ser Gly Ser Pro Phe Gly
225                 230                 235                 240

Met Asp Val Trp Gly Gln Gly Thr Thr Val Thr Val Ser Ser
                245                 250

<210> SEQ ID NO 15
<211> LENGTH: 250
<212> TYPE: PRT
<213> ORGANISM: Artificial Sequence
<220> FEATURE:
<223> OTHER INFORMATION: vector

<400> SEQUENCE: 15

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Gly Ile
        35                  40                  45

Ser Ser Trp Leu Ala Trp Tyr Gln Gln Lys Pro Glu Lys Ala Pro Lys
50                  55                  60

Ser Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Asn Ser
            100                 105                 110

```
Tyr Pro Tyr Thr Phe Gly Gln Gly Thr Lys Leu Glu Ile Lys Ser Gly
            115                 120                 125

Gly Gly Gly Ser Gln Val Gln Leu Val Gln Ser Gly Ala Glu Val Lys
        130                 135                 140

Lys Pro Gly Ala Ser Val Lys Val Ser Cys Lys Ala Ser Gly Tyr Thr
145                 150                 155                 160

Phe Thr Ser Tyr Asp Val His Trp Val Arg Gln Ala Pro Gly Gln Arg
                165                 170                 175

Leu Glu Trp Met Gly Trp Leu His Ala Asp Thr Gly Ile Thr Lys Phe
            180                 185                 190

Ser Gln Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Glu Arg Ile Gln Leu Trp Phe Asp Tyr Trp
225                 230                 235                 240

Gly Gln Gly Thr Leu Val Thr Val Ser Ser
                245                 250

<210> SEQ ID NO 16
<211> LENGTH: 249
<212> TYPE: PRT
<213> ORGANISM: Artificial Sequence
<220> FEATURE:
<223> OTHER INFORMATION: vector

<400> SEQUENCE: 16

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Val Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Arg Thr Phe Gly Gln Gly Thr Lys Val Glu Ile Lys Ser Gly
            115                 120                 125

Gly Gly Gly Ser Gln Val Gln Leu Val Gln Ser Gly Ala Glu Val Lys
        130                 135                 140

Lys Pro Gly Ala Ser Val Lys Val Ser Cys Lys Ala Ser Gly Tyr Thr
145                 150                 155                 160

Phe Thr Asp Tyr Gly Phe Ser Trp Val Arg Gln Ala Pro Gly Gln Gly
                165                 170                 175

Leu Glu Trp Met Gly Trp Ile Thr Ala Tyr Asn Gly Asn Thr Asn Tyr
            180                 185                 190

Ala Gln Lys Leu Gln Gly Arg Val Thr Met Thr Thr Asp Thr Ser Thr
        195                 200                 205

Ser Thr Val Tyr Met Glu Leu Arg Ser Leu Arg Ser Asp Asp Thr Ala
    210                 215                 220
```

```
Val Tyr Tyr Cys Ala Arg Asp Tyr Phe Tyr Gly Met Asp Val Trp Gly
225                 230                 235                 240

Gln Gly Thr Thr Val Thr Val Ser Ser
            245

<210> SEQ ID NO 17
<211> LENGTH: 250
<212> TYPE: PRT
<213> ORGANISM: Artificial Sequence
<220> FEATURE:
<223> OTHER INFORMATION: vector

<400> SEQUENCE: 17

Gly Gly Gly Gly Ser Gln Val Gln Leu Val Gln Ser Gly Ala Glu Val
1               5                   10                  15

Lys Lys Pro Gly Ala Ser Val Lys Val Ser Cys Lys Ala Ser Gly Tyr
            20                  25                  30

Thr Phe Thr Ser Tyr Tyr Ile His Trp Val Arg Gln Ala Pro Gly Gln
            35                  40                  45

Gly Leu Glu Trp Ile Gly Cys Ile Tyr Pro Gly Asn Val Asn Thr Asn
    50                  55                  60

Tyr Asn Glu Lys Phe Lys Asp Arg Ala Thr Leu Thr Val Asp Thr Ser
65                  70                  75                  80

Ile Ser Thr Ala Tyr Met Glu Leu Ser Arg Leu Arg Ser Asp Asp Thr
                85                  90                  95

Ala Val Tyr Phe Cys Thr Arg Ser His Tyr Gly Leu Asp Trp Asn Phe
            100                 105                 110

Asp Val Trp Gly Gln Gly Thr Thr Val Thr Val Ser Ser Val Glu Gly
        115                 120                 125

Gly Ser Gly Gly Ser Gly Gly Ser Gly Gly Ser Gly Gly Val Asp Asp
        130                 135                 140

Ile Gln Met Thr Gln Ser Pro Ser Ser Leu Ser Ala Ser Val Gly Asp
145                 150                 155                 160

Arg Val Thr Ile Thr Cys His Ala Ser Gln Asn Ile Tyr Val Trp Leu
                165                 170                 175

Asn Trp Tyr Gln Gln Lys Pro Gly Lys Ala Pro Lys Leu Leu Ile Tyr
            180                 185                 190

Lys Ala Ser Asn Leu His Thr Gly Val Pro Ser Arg Phe Ser Gly Ser
            195                 200                 205

Gly Ser Gly Thr Asp Phe Thr Leu Thr Ile Ser Ser Leu Gln Pro Glu
        210                 215                 220

Asp Phe Ala Thr Tyr Tyr Cys Gln Gln Gly Gln Thr Tyr Pro Tyr Thr
225                 230                 235                 240

Phe Gly Gly Gly Thr Lys Val Glu Ile Lys
            245                 250
```

COMPOSITIONS AND METHODS FOR T CELL DELIVERY OF THERAPEUTIC MOLECULES

CROSS-REFERENCE TO RELATED APPLICATION

The present application is divisional of U.S. patent application Ser. No. 15/544,816, filed Jul. 19, 2017 (allowed), a 35 U.S.C. § 371 national phase application from, and claims priority to, International Application No. PCT/US2015/058192, filed Oct. 30, 2015, which claims priority under 35 U.S.C. § 119(e) to U.S. Provisional Application No. 62/110,489, filed Jan. 31, 2015, all of which applications are incorporated herein by reference in their entireties.

STATEMENT REGARDING FEDERALLY SPONSORED RESEARCH OR DEVELOPMENT

This invention was made with government support under CA120409 awarded by the National Institute of Health. The government has certain rights in the invention.

BACKGROUND OF THE INVENTION

Genetically engineered T cells have been used to treat cancer and induce immune responses. However, T cells modified with CARs alone may not be sufficient for efficiently treating cancers, especially solid cancers. Effective tumor immunotherapy is hindered by immunological obstacles, such as the ability of tumors to foster a tolerant microenvironment and the activation of a plethora of immunosuppressive mechanisms, which may act in concert to counteract effective immune responses. While an obvious clinical strategy has been to bolster anti-tumor mechanisms, achieving clinical success has been limited. Possible mechanisms underlying these clinical failures include the underappreciated properties of some immune cell types that can harbor both immunosuppressive activity, e.g., blunting malignant cell killing by $CD8^+$ cytotoxic T lymphocytes (CTLs) or natural killer (NK) cells, simultaneously with protumor activities that promote survival, invasion, and dissemination of malignant cells Despite expanded appreciation for the diversity of cellular mechanisms fostering solid tumor development, anti-cancer therapy remains heavily reliant on cytotoxic modalities, including chemotherapy (CTX) and radiation therapy (RT), that kill rapidly proliferating (neoplastic) cells within tumors. Therefore a need exists in the art for improved methods to generate T cells that could treat cancer and induce immune responses in vivo as T cell based adoptive immunotherapies.

SUMMARY OF THE INVENTION

In one aspect, the invention includes a modified T cell comprising a nucleic acid encoding a switch molecule, wherein the switch molecule comprises: an extracellular domain comprising a membrane receptor or fragment thereof selected from the group consisting of a cytokine receptor, a chemokine receptor, a growth factor receptor, a hormone receptor, and other signaling receptor; and an intracellular domain comprising a signaling receptor or fragment thereof, or an extracellular domain comprising a signaling receptor or fragment thereof, wherein the T cell transiently expresses the switch molecule and interaction of the extracellular domain of the switch molecule with its respective ligand induces the T cell to secrete an activation factor at a target site.

In one aspect, the extracellular domain comprising the membrane receptor or fragment thereof is selected from the group consisting of transforming growth factor-beta receptor (TGF-beta-R), programmed cell death 1 (PD1), programmed cell death ligand 1 (PDL1), interferon-gamma receptor (IFN-gamma), and any combination thereof. In another aspect, wherein the intracellular domain comprising the signaling receptor or fragment thereof is selected from the group consisting of interleukin-2 receptor (IL-2R), interleukin-12 receptor (IL-12R), CD3, CD28, CD137, CD27, ICOS, OX40, and any combination thereof. In a further aspect, the activation factor is a soluble cytokine selected from the group consisting of IL-1, IL-2, IL-6, IL-7, IL-8, IL-10, IL-12, IL-15, IL-21, TNF, TGF, IFN, and functional fragments and variants thereof. In yet another aspect, wherein the nucleic acid comprises in vitro transcribed RNA or synthetic RNA. In other aspects, the target site is a tumor selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof. In yet a further aspect, T cell homes to a solid tumor site or to a tumor antigen. In another aspect the tumor antigen is selected from the group consisting of tumor associated antigen (TAA), viral antigen, antibody-recognized antigen, and any fragment thereof, and any combination thereof. In further embodiments, the tumor antigen is selected from the group consisting of p53, Ras, beta-Catenin, CDK4, alpha-Actinin-4, Tyrosinase, TRP1/gp75, TRP2, gp100, Melan-A/MART1, Gangliosides, PSMA, HER2, WT1, EphA3, EGFR, CD20, MAGE, BAGE, GAGE, NY-ESO-1, Telomerase, Survivin, and any combination thereof. In yet another aspect, the T cell is activated.

The invention also features a modified T cell comprising a nucleic acid encoding a switch molecule, wherein the switch molecule comprises an extracellular domain comprising a transforming growth factor-beta receptor (TGF-beta-R) or fragment thereof and an intracellular domain comprising a IL-12R or fragment thereof.

Further included is a population of modified T cells comprising a nucleic acid encoding a switch molecule, wherein the T cells transiently express the switch molecule and interaction of the switch molecule with its respective ligand induces the T cells to secrete an activation factor at a target site.

The invention also includes a modified T cell comprising a nucleic acid encoding a soluble fusion protein, wherein the soluble fusion protein comprises a first binding domain comprising an anti-CD28 scFv and a second binding domain comprising an anti-PD-L1 or anti-TGFbRII scFv. In one embodiment, the soluble fusion protein further comprises a spacer domain between the first and second binding domains.

Additionally included is a modified T cell comprising: a nucleic acid encoding a switch molecule comprising an extracellular domain comprising a membrane receptor or fragment thereof and an intracellular domain comprising a signaling receptor or fragment thereof and a nucleic acid encoding a bispecific antibody comprising bispecificity for an antigen on a target cell and an antigen on an activating T cell, wherein the T cell transiently expresses the switch molecule and secretes the bispecific antibody.

In one aspect, the extracellular domain comprising the membrane receptor or fragment thereof is selected from the group consisting of a cytokine receptor, a chemokine receptor, a growth factor receptor, a hormone receptor, and other signaling receptor. In another aspect, the extracellular domain comprising the membrane receptor or fragment thereof is selected from the group consisting of transforming growth factor-beta receptor (TGF-beta-R), programmed cell death 1 (PD1), programmed cell death ligand 1 (PDL1), interferon-gamma receptor (IFN-gamma), and any combination thereof. In yet another aspect, the intracellular domain comprising the signaling receptor or fragment thereof is selected from the group consisting of interleukin-2 receptor (IL-2R), interleukin-12 receptor (IL-12R), CD3, CD28, CD137, and any combination thereof. In one embodiment, the target cell antigen is selected from the group consisting of a tumor associated antigen (TAA), viral antigen, bacteria antigen, parasite antigen, and any fragment thereof. In other embodiments, the target cell antigen is selected from the group consisting of transforming growth factor-beta receptor (TGF-beta-R), programmed cell death 1 (PD1), programmed cell death ligand 1 (PDL1), interferon-gamma receptor (IFN-gamma). In further embodiments, the activating T cell antigen is selected from the group consisting of CD3, CD4, CD8, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and any fragment thereof. In yet additional embodiments, the T cell is activated by binding the switch molecule to a ligand and activation induces the T cell to secrete an activation factor at a target site. Additionally, the T cell is activated by binding to the bispecific antibody and activation induces the T cell to secrete an activation factor at a target site. In additional embodiments, in the activation factor is a soluble cytokine selected from the group consisting of IL-1, IL-2, IL-6, IL-7, IL-8, IL-10, IL-12, IL-15, IL-21, TNF, TGF, IFN, and functional fragments and variants thereof. In further embodiments, the target site is a tumor selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof. Additionally in other embodiments, the T cell homes to a solid tumor site or to a tumor antigen. The tumor antigen is selected from the group consisting of tumor associated antigen (TAA), viral antigen, antibody-recognized antigen, and any fragment thereof, and any combination thereof, or the tumor antigen is selected from the group consisting of p53, Ras, beta-Catenin, CDK4, alpha-Actinin-4, Tyrosinase, TRP1/gp75, TRP2, gp100, Melan-A/MART1, Gangliosides, PSMA, HER2, WT1, EphA3, EGFR, CD20, MAGE, BAGE, GAGE, NY-ESO-1, Telomerase, Survivin, and any combination thereof. In these and other embodiments, any one of the nucleic acids may comprise in vitro transcribed RNA or synthetic RNA.

The invention additionally includes a population of modified T cells comprising a nucleic acid encoding a switch molecule and at least one of nucleic acid encoding soluble fusion protein and a nucleic acid encoding a bispecific antibody, wherein the T cells transiently expresses the switch molecule and secretes the soluble fusion protein and/or the bispecific antibody.

The invention further includes a method for delivering a factor to a target site. The method comprises introducing a nucleic acid encoding a switch molecule into a population of cells comprising modified T cells. The switch molecule comprises an extracellular domain comprising a membrane receptor or fragment thereof selected from the group consisting of a cytokine receptor, a chemokine receptor, a growth factor receptor, a hormone receptor, and other signaling receptor; and an intracellular domain comprising a signaling receptor or fragment thereof. The population of cells is administered to a subject in need thereof, wherein the T cells transiently express the switch molecule and interaction of the extracellular domain of the switch molecule with its respective ligand induces the T cells to secrete an activation factor at the target site. In one embodiment, introducing the nucleic acid comprises electroporating the nucleic acid. In one aspect, the population of cells is selected from the group consisting of peripheral blood mononuclear cells, cord blood cells, a purified population of T cells, and a T cell line. In another aspect, the population of cells comprises peripheral blood mononuclear cells. In another aspect, the population of cells comprises purified T cells. In other aspects, the method further comprises activating and expanding the T cells prior to introducing the nucleic acid. In one embodiment, the T cells are activated with anti-CD3 and anti-CD28 antibodies. In further aspects, the extracellular domain comprises the membrane receptor or fragment thereof is selected from the group consisting of transforming growth factor-beta receptor (TGF-beta-R), programmed cell death 1 (PD1), programmed cell death ligand 1 (PDL1), interferon-gamma receptor (IFN-gamma), and any combination thereof. In additional embodiments, the intracellular domain comprising the signaling receptor or fragment thereof is selected from the group consisting of interleukin-2 receptor (IL-2R), interleukin-12 receptor (IL-12R), CD3, CD28, CD137, CD27, ICOS, OX40, and any combination thereof. In other embodiments, the nucleic acid comprises in vitro transcribed RNA or synthetic RNA. In other embodiments, the activation factor is the soluble cytokine selected from the group consisting of IL-1, IL-2, IL-6, IL-7, IL-8, IL-10, IL-12, IL-15, IL-21, TNF, TGF, IFN, and functional fragments and variants thereof. In further embodiments, the T cells bind a tumor antigen. In additional embodiments, the tumor antigen is an antigen associated with a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

Also included in the invention is a method for delivering a factor to a target site. The method comprises administering a population of cells to a subject in need thereof, wherein the T cells transiently express a switch molecule. The switch molecule comprises an extracellular domain comprising a transforming growth factor-beta receptor (TGF-beta-R) or fragment thereof and an intracellular domain comprising a IL-12R or fragment thereof. The interaction of the extracellular domain of the switch molecule with its respective ligand induces the T cells to secrete an activation factor at the target site.

The invention additionally includes a method for delivering a factor to a target site. The method comprises administering a population of cells comprising T cells to a subject in need thereof, wherein the T cells home to the target site and transiently express a switch molecule. The switch molecule comprises an extracellular domain comprising a membrane receptor or fragment thereof and an intracellular domain comprising a signaling receptor or fragment thereof and a bispecific antibody comprising bispecificity for an antigen on a target cell and an antigen on an activating T cell and the T cells are activated at the target site, wherein the T cells are induced to secrete an activation factor. In one embodiment, activating the T cells comprises binding a ligand to the extracellular domain of the switch molecule. In another embodiment, activating the T cells comprises binding the bispecific antibody to the activating T cell antigen on the T cells.

Also included in the invention is a method of treating a disease or condition. The method comprises administering population of modified T cells to a subject where the T cells comprises a nucleic acid encoding a switch molecule comprising an extracellular domain comprising a membrane receptor or fragment thereof selected from the group consisting of a cytokine receptor, a chemokine receptor, a growth factor receptor, a hormone receptor, and other signaling receptor; and an intracellular domain comprising a signaling receptor or fragment thereof. The T cells transiently express the switch molecule and interaction of the extracellular domain of the switch molecule with its respective ligand induces the T cells to secrete an activation factor at the target site, thereby treating the disease or condition.

Also included in the invention is a method of treating a disease or condition in a subject. The method comprises administering to the subject a population of modified T cells comprising a nucleic acid encoding a switch molecule comprising an extracellular domain comprising a membrane receptor or fragment thereof and an intracellular domain comprising a signaling receptor or fragment thereof and at least one of a nucleic acid encoding soluble fusion protein and a nucleic acid encoding a bispecific antibody comprising bispecificity for an antigen on a target cell and an antigen on an activating T cell. The T cells transiently express the switch molecule and soluble fusion protein and/or bispecific antibody and activation of the T cells induces secretion of an activation factor at the target site, thereby treating the disease or condition. In certain embodiments, the disease or condition is a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof. In other embodiments, the disease or condition is an autoimmune disease is selected from the group consisting of Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo, Wegener's granulomatosis, and any combination thereof. In certain embodiments, administering the T cells comprises inducing lysis of the target cell or tissue.

Further included in the invention is a method for generating a T cell transiently expressing a switch molecule. The method comprises introducing a nucleic acid encoding a switch molecule into a population of T cells, wherein the switch molecule comprises an extracellular domain comprising a membrane receptor or fragment thereof selected from the group consisting of a cytokine receptor, a chemokine receptor, a growth factor receptor, a hormone receptor, and other signaling receptor; and an intracellular domain comprising a signaling receptor or fragment thereof. The T cells transiently express the switch molecule and interaction of the extracellular domain of the switch molecule with its respective ligand induces the T cells to secrete an activation factor at a target site, thereby generating the T cell.

In addition, there is included a method for generating a T cell transiently expressing a switch molecule and bispecific antibody. The method comprises introducing a nucleic acid encoding a switch molecule comprising an extracellular domain comprising a membrane receptor or fragment thereof selected from the group consisting of a cytokine receptor, a chemokine receptor, a growth factor receptor, a hormone receptor, and other signaling receptor, or an extracellular domain comprising a signaling receptor or fragment thereof and an intracellular domain comprising a signaling receptor or fragment thereof and at least one of a nucleic acid encoding a soluble fusion protein and a nucleic acid encoding a bispecific antibody comprising bispecificity for an antigen on a target cell and an antigen on an activating T cell. The T cells transiently express the switch molecule and soluble fusion protein and/or bispecific antibody and activation of the T cells induces secretion of an activation factor at a target site. In certain embodiments, the T cells to home to a target site, wherein the T cells secrete the activation factor at the target site. In other embodiments, the population of T cells is comprised within cells selected from the group consisting of peripheral blood mononuclear cells, cord blood cells, a purified population of T cells, and a T cell line. In other embodiments, peripheral blood mononuclear cells comprises the population of T cells. In further embodiments, purified T cells comprises the population of T cells. In other embodiments, the population of T cells are cryopreserved and in certain methods disclosed herein, the cryopreserved T cells are thawed.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 16A is a panel of flow graphs showing the increase of T cell activation and tumor killing ability of Bis-RNA electroporated T cells. T cells were electroporated with a different amount Gig RNA/0.1 ml T cells) of either Blinatumomab Bis-RNA (Bis-RNA) or CD19 CAR RNA (CAR RNA) as indicated. Eighteen hours after electroporation, the T cells with either Bis-RNA or CAR RNA were stimulated with CD19 positive cell lines with or without adding an equal number of GFP RNA electroporated T cells (GFP-T) and assessed for CD107a expression.

FIG. 17 is a table listing the soluble fusion protein RNAs electroporated into T cells.

DETAILED DESCRIPTION

Definitions

Figure 1:
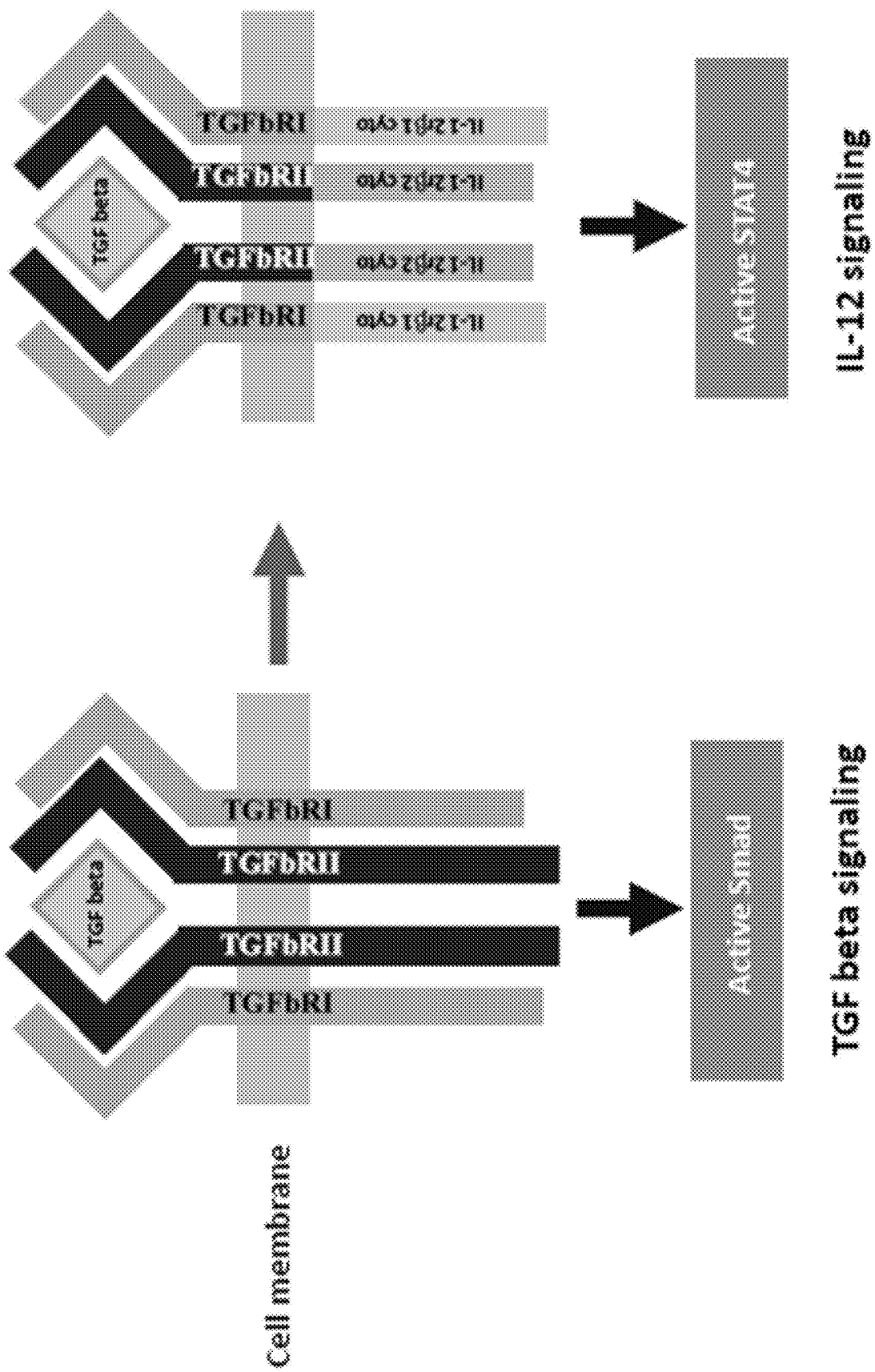
FIG. 1 is an illustration showing construction of switch molecules, TGF-beta receptors to IL-12 receptors switching.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "activation factor" refers to an immunomodulating molecule. The activation factor may bind, activate, or stimulate T cells or other immune cells to modulate their activity. The activation factor is further in a form that is capable of secretion from the cell, such as lacking a transmembrane region. In some embodiments, the activation factor is selected from an antibody, a soluble cytokine, a soluble chemokine, a growth factor, or a functional fragment or variant thereof.

The term "antibody," as used herein, refers to an immunoglobulin molecule which specifically binds with an antigen. Antibodies can be intact immunoglobulins obtained from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab')$_2$, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a region of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a fragment of a human antibody or a humanized antibody thereof.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be generated from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated, synthesized or originate from a biological sample. Such a biological sample can include, but is not limited to a tissue sample, a tumor sample, a cell or a biological fluid.

As used herein, the term "autologous" is meant to refer to any material originating from the same individual to which it is later to be re-introduced into the individual.

"Allogeneic" refers to a graft derived from a different animal of the same species.

"Xenogeneic" refers to a graft derived from an animal of a different species.

A "bispecific antibody," as used herein, refers to an antibody having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan et al. (1985) Science 229:81. Bispecific antibodies include bispecific antibody fragments. See, e.g., Holliger et al. (1993) Proc. Natl. Acad. Sci. U.S.A. 90:6444-48, Gruber et al. (1994) J. Immunol. 152:5368.

"Bispecificity," as used herein, refers to a molecule having binding specificities for at least two different binding epitopes. In one embodiment, the epitopes are from the same binding partner. In another embodiment, the epitopes are from two different binding partners. The molecule with bispecificity to different epitopes may include a bispecific antibody.

The term "cancer" as used herein is defined as a disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind to antigen using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an WIC class I molecule, BTLA and a Toll ligand receptor.

The term "derived from" refers to being generated, synthesized, or originating from a particular source, such that the derived matter is related to the source. The derived matter does not need to be identical to the particular source. In one embodiment, an antigen is derived from a protein. In another embodiment, a single-chain variable fragment is derived from a monoclonal antibody.

The terms "electroporate," "electroporation," "electroporated" refer to the process by which an electrical field is applied to a cell plasma membrane to increase its permeability. A pulse of a specific duration and shape is applied to the cell membrane of a cell to introduce nucleic acids into the cell.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The phrase "extracellular domain comprising a membrane receptor or fragment thereof" refers to the fragment or portion of a membrane receptor on the outside of the cell. The extracellular domain comprising the membrane receptor or fragment thereof includes the ligand binding or recognition domain. The extracellular domain may or may not include a transmembrane domain of the membrane receptor.

As used herein, the terms "expand," and "expansion" refer to the proliferation or multiplication of cells, such as T cells.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The phrases "an immunologically effective amount", "an anti-immune response effective amount", "an immune response-inhibiting effective amount", or "therapeutic amount" refer to the amount of the composition of the present invention to be administered to a subject which amount is determined by a physician, optionally in consultation with a scientist, in consideration of individual differences in age, weight, immune response, type of disease/condition, and the health of the subject (patient) so that the desired result is obtained in the subject.

The phrase "intracellular domain comprising a signaling receptor or fragment thereof" refers to the fragment or portion of an activation receptor on the inside of the cell that is responsible for activation of at least one effector function. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. The intracellular domain comprising the signaling receptor or fragment thereof may include the signaling domain, protein interaction domain, enzymatic domain, or a combination thereof. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal. The intracellular domain may or may not include a transmembrane domain of the activation receptor.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The phrase "membrane receptor" refers to any receptor found on the surface of a T cell or NK cell. The membrane receptor may include receptors for hormones, cytokines, growth factors, cell recognition molecules, or other signaling receptors. Exemplary examples of membrane receptors include but are not limited to transforming growth factor-beta receptor (TGF-beta-R), programmed cell death 1 (PD1), programmed cell death ligand 1 (PDL1), interferon-gamma receptor (IFN-gamma), interleukin-2 receptor (IL-2R), interleukin-12 receptor (IL-12R), CD3, CD4, CD8, CD28, and CD137.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one region of a cell to another region of a cell. The phrase "cell surface receptor" includes molecules and complexes of molecules capable of receiving a signal and transmitting signal across the plasma membrane of a cell. An example of a "cell surface receptor" is human CD3 or CD28.

The term "signaling receptor" as used herein refers to a membrane receptor that interacts with a ligand to trigger a biochemical chain of events inside the cell, creating a response, such as signal transduction, protein interaction, enzymatic activity, or a combination thereof. Exemplary examples of signaling receptors include but are not limited to interleukin-2 receptor (IL-2R), interleukin-12 receptor (IL-12R), CD3, CD28, and CD137.

The term "soluble fusion protein" as used herein refers to a fusion having two different binding domains with different binding specificities. The soluble fusion protein is capable of binding two different ligands, receptors, antigens or molecules. In an exemplary embodiment, the soluble fusion protein includes one binding domain with specificity to bind at least one molecule on an activating T cell and second binding domain with specificity to bind at least one molecule on a target cell.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "switch molecule" refers to an engineered receptor comprising an extracellular domain comprising a membrane receptor or fragment thereof and an intracellular domain comprising a signaling receptor or fragment thereof. When the switch molecule is expressed in a cell, such as a T or NK cell, interaction with the extracellular domain of the switch molecule with its respective ligand activates the intracellular domain comprising the signaling receptor or fragment thereof. The intracellular domain transmits signals within the cell that are specific to the signaling receptor, such as transduction of signaling receptor signals, activation of effector molecules, secretion of an activation factor, or any combination thereof.

A "target site" or "target sequence" refers to a genomic nucleic acid sequence that defines a region of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (a) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "tumor antigen" as used herein refers to an antigen that is common to tumors, or specific hyperproliferative disorders. In some aspects, the tumor antigen of the present invention may be derived from, a cancer including but not limited to primary or metastatic melanoma, thymoma, lymphoma, sarcoma, lung cancer, liver cancer, non-Hodgkin's lymphoma, non-Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

T cells can be an ideal delivery vehicle when using novel T cell RNA electroporation technology. Targeted delivery of exogenously administered drugs is a limitation of current therapies. RNA electroporated T cells described herein can potentially overcome this limitation of using exogenously administered drugs to deliver molecules that orchestrate anti-tumor activities in tumor microenvironments to a target site.

The limitations of using viral transduction of T cells can also be overcome. using RNA electroporation of T cells. Unlike viral transduction of T cells, RNA electroporation is a transient, vector-free modification to the T cell. Moreover, integration of the RNA into the host cell genome is unlikely. T cells can be electroporated with RNA encoding molecules that initiate T cell specific killing of target tumor cells and enhance T cell antitumor activities, such as switch molecules to convert T cell negative signals, like PD1 or TGF-beta, to positive signals, like CD28.

The present invention includes modifying T cells to act as delivery vehicles to transiently express and secrete a factor to a target site. In one embodiment, a method for delivering a factor to a target site includes electroporating a population of cells comprising T cells with mRNA encoding a switch molecule, wherein the T cells transiently express the switch molecule and the switch molecule induces the T cells to secrete an activation factor at the target site.

By electroporating and administering the T cells according to the described invention, the T cells may home to the target site. The T cells transiently express the switch molecule and secrete an activation factor at the target site. Accordingly, the present invention facilitates expression of switch molecules and delivery of activation factors to the target site to modulate immune activity.

Switch Molecules

The present invention includes a modified T cell comprising an electroporated nucleic acid encoding a switch molecule. In one aspect, the invention includes a method for generating a T cell transiently expressing a switch molecule. The switch molecule is generally composed of an extracellular domain comprising a membrane receptor or fragment thereof or extracellular domain comprising a signaling receptor or fragment thereof and an intracellular domain comprising a signaling receptor or fragment thereof.

When a nucleic acid encoding the switch molecule is expressed in a cell, such as a T or NK cell, interaction of the extracellular domain of the switch molecule with its respective ligand activates the intracellular domain comprising the switch molecule or fragment thereof. The intracellular domain transmits signals within the cell that are specific to the intracellular domain, such as transduction of signaling receptor signals, activation of effector molecules, secretion of an activation factor, or any combination thereof.

In one aspect, the invention includes a modified T cell comprising an electroporated nucleic acid encoding a switch molecule. The switch molecule comprises an extracellular domain comprising a membrane receptor or fragment thereof selected from the group consisting of a cytokine receptor, a chemokine receptor, a growth factor receptor, a hormone receptor, and other signaling receptor or an extracellular domain comprising a signaling receptor or fragment thereof and an intracellular domain comprising a signaling receptor or fragment thereof. The T cell transiently expresses the switch molecule and interaction of the extracellular domain of the switch molecule with its respective ligand induces the T cell to secrete an activation factor at a target site.

Extracellular Domain

The extracellular domain comprising a membrane receptor or fragment thereof may include the ligand binding domain or ligand recognition domain. In one embodiment, the extracellular domain comprising the membrane receptor or fragment thereof is a fragment or a domain of a transforming growth factor-beta receptor (TGF-beta-R), programmed cell death 1 (PD1), programmed cell death ligand 1 (PDL1), interferon-gamma receptor (IFN-gamma), or any combination thereof.

In one aspect, the switch molecule comprises an extracellular domain comprising a transforming growth factor-beta receptor (TGF-beta-R) or fragment thereof Intracellular Domain The intracellular domain comprises a costimulatory signaling region. The costimulatory signaling region refers to an intracellular domain or fragment thereof of a signaling receptor. A signaling receptor includes, but is not limited to, a costimulatory molecule or cell surface molecule that is required for an efficient activation of a lymphocyte. In another embodiment, the intracellular domain comprising a signaling receptor or fragment thereof includes a fragment or domain of an activation receptor. The intracellular domain comprising the signaling receptor or fragment thereof may include a signaling domain, a protein interaction domain, an enzymatic domain, or any combination thereof. In yet another embodiment, the intracellular domain comprising the signaling receptor or fragment thereof includes any fragment or domain of an intracellular domain from interleukin-2 receptor (IL-2R), interleukin-12 receptor (IL-12R), CD3, CD28, CD137, CD27, ICOS, OX40, T cell receptor (TCR), co-stimulatory molecules, any derivative or variant of these sequences, any synthetic sequence that has the same functional capability, and any combination thereof.

In one aspect, the switch molecule comprises an intracellular domain comprising a IL-12R or fragment thereof.

Other Domains

In some embodiments, the switch molecule further comprises a transmembrane domain. In some embodiment, the switch molecule further comprises a hinge domain. In one embodiment, a nucleic acid encoding the switch molecule further comprises a nucleic acid encoding a transmembrane domain and nucleic acid encoding a hinge domain, such as a nucleic acid encoding a CD28 transmembrane domain and a nucleic acid encoding a CD8-alpha hinge domain. The extracellular domain and/or the intracellular domain may also include a transmembrane domain from the same receptor molecule of either the extracellular domain or the intracellular domain.

Between the extracellular domain and the transmembrane domain of the switch molecule, or between the intracellular domain and the transmembrane domain of the switch molecule, there may be a spacer domain. As used herein, the term "spacer domain" generally means any oligo- or polypeptide that functions to link the transmembrane domain to, either the extracellular domain or, the intracellular domain in the polypeptide chain. A spacer domain may comprise up to 300 amino acids, preferably 10 to 100 amino acids and most preferably 25 to 50 amino acids.

Bispecific Antibodies

The present invention also includes a bispecific antibody. A bispecific antibody comprises two different binding specificities and thus binds to two different antigens. In one embodiment, the bispecific antibody comprises a first antigen binding domain that binds to a first antigen and a second antigen binding domain that binds to a second antigen. In another embodiment, the bispecific antibody comprises an antigen binding domain comprising a first and a second single chain variable fragment (scFv) molecules. In one embodiment, the first and a second antigen binding domains bind an antigen on a target cell and an antigen on an activating T cell.

In one embodiment, the bispecific antibody comprises specificity to at least one antigen on an activating T cell. The activating T cell antigen includes antigens found on the surface of a T cell that can activate another cell. The activating T cell antigen may bind a co-stimulatory molecule. A costimulatory molecule is a cell surface molecule, other than an antigen receptor or their ligands, that is required for an efficient response of lymphocytes to an antigen. Examples of the activating T cell antigen can include but are not limited to CD3, CD4, CD8, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, or any fragment thereof. Other costimulatory elements are also within the scope of the invention. In these examples, the bispecific antibody recognizes a T cell antigen and is referred to as a Bispecific T Cell Engager (BiTE). However, the present invention is not limited by the use of any particular bispecific antibody. Rather, any bispecific antibody or BiTE can be used. The bispecific antibody or BiTE molecule may also be expressed as a soluble protein with specificity for at least one target cell associated antigen.

In one embodiment, the bispecific antibody comprises more than one antigen binding domains. In this embodiment, at least one antigen binding domain includes a synthetic antibody, human antibody, a humanized antibody, single chain variable fragment, single domain antibody, an antigen binding fragment thereof, and any combination thereof. Techniques for making human and humanized antibodies are described elsewhere herein.

In another embodiment, the target cell antigen may be the same antigen that a T cell receptor binds to or may be a different antigen. The target cell antigen includes any tumor associated antigen (TAA) or viral, bacterial and parasitic antigen, or any fragment thereof. The target cell antigen may include any type of ligand that defines the target cell. For example, the target cell antigen may be chosen to recognize a ligand that acts as a cell marker on target cells associated with a particular disease state. Thus, cell markers may act as ligands for the antigen binding domain in the bispecific antibody, including those associated with viral, bacterial and parasitic infections, autoimmune disease and cancer cells.

In another embodiment, the target cell antigen is the same antigen as the activating T cell antigen including, but not limited to, CD3, CD4, CD8, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and fragments thereof. In one aspect, the invention includes a nucleic acid encoding a bispecific antibody comprising bispecificity for an antigen on a target cell and an antigen on an activating T cell, wherein the T cell transiently secretes the bispecific antibody. Techniques for engineering and expressing bispecific antibodies include, but are not limited to, recombinant co-expression of two immunoglobulin heavy chain-light chain pairs having different specificities (see Milstein and Cuello, Nature 305: 537

(1983), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science 229:81 (1985)); using leucine zippers to produce bispecific antibodies (see, e.g., Kostelny et al., J. Immunol. 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991). Engineered antibodies with three or more functional antigen binding sites, including "Octopus antibodies," are also included herein (see, e.g. US 2006/0025576A1). Bispecific antibodies can be constructed by linking two different antibodies, or portions thereof. For example, a bispecific antibody can comprise Fab, F(ab')2, Fab', scFv, and sdAb from two different antibodies.

Soluble Fusion Proteins

The present invention also includes a T cell modified to express a soluble fusion protein with or without the switch molecule. A soluble fusion protein comprises two different binding specificities and thus binds to two different ligands or receptors or antigens or molecules. In one embodiment, the soluble fusion protein comprises a first binding domain that binds to a first ligand, receptor, antigen or fragment thereof and a second binding domain that binds to a second ligand, receptor, antigen or fragment thereof. In another embodiment, the soluble fusion protein comprises a first binding domain comprising a first single chain variable fragment (scFv) molecule and a second binding domain comprising a second single chain variable fragment (scFv) molecule. In one embodiment, the first and a second binding domains bind a receptor on a target cell and a receptor on an activating T cell, respectively.

In one embodiment, the soluble fusion protein comprises at least one binding domain with specificity to bind at least one molecule on an activating T cell. The activating T cell molecule includes any surface molecules found on a T cell. The activating T cell molecule may bind a co-stimulatory molecule. A costimulatory molecule is a cell surface molecule that is required for an efficient response of lymphocytes to an antigen. Examples of the activating T cell molecule can include but are not limited to CD3, CD4, CD8, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, or any fragment thereof. Other costimulatory elements are also within the scope of the invention. However, the present invention is not limited by the use of antibodies. Rather, any ligand, receptor, antigen or fragment thereof can be used as part of the soluble fusion protein. In one embodiment, the soluble fusion protein comprises at least one binding domain with specificity to bind CD28, such as but not limited to a ligand, an antibody, or any fragment thereof. In a particular embodiment, the soluble fusion protein comprises a binding domain comprising an anti-CD28 scFv.

In one embodiment, the soluble fusion protein comprises at least one binding domain comprising a synthetic antibody, human antibody, a humanized antibody, single chain variable fragment, single domain antibody, an antigen binding fragment thereof, and any combination thereof. Techniques for making human and humanized antibodies are described elsewhere herein.

In another embodiment, the soluble fusion protein comprises at least one binding domain with specificity to bind any tumor associated antigen (TAA) or viral, bacterial and parasitic antigen, or any fragment thereof. The binding domain with specificity to bind any type of ligand that defines a target cell. For example, the binding domain may specifically bind to a molecule on a target cell chosen to recognize the target cell as associated with a particular disease state. In one embodiment, the soluble fusion protein comprises at least one binding domain with specificity to bind TGFbRII, such as but not limited to a ligand, an antibody, or any fragment thereof. In a particular embodiment, the soluble fusion protein comprises a second binding domain comprising an anti-TGFbRII scFv. In another embodiment, the soluble fusion protein comprises at least one binding domain with specificity to bind PD-L1, such as but not limited to a ligand, an antibody, or any fragment thereof. In a particular embodiment, the soluble fusion protein comprises a binding domain comprising an anti-PD-L1 scFv.

In another embodiment, the soluble fusion protein comprises at least one binding domain with specificity to bind at least one molecule on a target cell antigen. The binding domain may bind the same molecule on the activating T cell, including, but not limited to, CD3, CD4, CD8, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and fragments thereof.

The soluble fusion protein may further include a spacer domain between the binding domains. As used herein, the term "spacer domain" generally means any oligo- or polypeptide that functions to link the first and second binding domains in a polypeptide chain. A spacer domain may comprise up to 100 amino acids, preferably 2 to 50 amino acids and most preferably 5 to 10 amino acids.

Human Antibodies

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody is humanized, where specific sequences or regions of the antibody are modified to increase similarity to an antibody naturally produced in a human. In one embodiment, the antigen binding domain is humanized.

A "humanized" antibody retains a similar antigenic specificity as the original antibody. However, using certain methods of humanization, the affinity and/or specificity of binding of the antibody for the human antigen may be increased using methods of "directed evolution," as described by Wu et al., J. Mol. Biol., 294:151 (1999), the contents of which are incorporated herein by reference herein in their entirety.

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

Co-Stimulatory Molecule

In one embodiment, the modified T cell or cell of the invention further includes introducing a nucleic acid encoding a co-stimulatory molecule, such as an electroporated nucleic acid encoding the costimulatory molecule into the modified T cell or cell. The nucleic acid may be introduced into the T cell or cell by transduction, transfection, or electroporation. In another embodiment, the co-stimulatory domain is selected from CD3, CD27, CD28, CD83, CD86, CD127, 4-1BB, 4-1BBL, PD1 and PD1L. In yet another embodiment, the CD3 comprises at least two different CD3 chains, such as CD3 zeta and CD3 epsilon chains. In an exemplary embodiment, RNA encoding the co-stimulatory molecule, such as CD3, is electroporated into the T cell or cell. In another embodiment, the nucleic acid encoding the costimulatory molecule, such as CD3 RNA, is co-electroporated with another nucleic acid, such as the nucleic acid or RNA encoding the switch molecule.

Activation Factor

The present invention includes an activation factor, such as an immunomodulating molecule. In one aspect, interaction of the switch molecule with its respective ligand induces the T cell to secrete an activation factor. The activation factor may bind, activate, or stimulate T cells or other immune cells and modulate their activity. The activation factor is also in a form that is capable of secretion from the T cell, such an activation factor lacks a transmembrane region. In some embodiments, the activation factor is selected from an antibody, a soluble cytokine, a soluble chemokine, a growth factor, or a functional fragment or variant thereof. In those embodiments where the activation factor is a soluble cytokine, the soluble cytokine may be, without limitation, any of IL-1, IL-2, IL-6, IL-7, IL-8, IL-10, IL-12, IL-15, IL-21, TNF, TGF, IFN, and functional fragments and variants thereof. When the activation factor is an antibody or a functional fragment or variant thereof, the antibody or the functional fragment or variant thereof may bind agonistically or antagonistically to a receptor on another T cell or a target cell.

Secretion of the activation factor at the target site may promote activation of other immune cells in the target site. For example, secretion of interferon-gamma by the T cell expressing the switch molecule activates macrophages and NK cells, while providing important immunostimulatory and immunomodulatory effects to T cells.

T Cells and Compositions Thereof

One aspect of the invention includes a T cell comprising an electroporated mRNA encoding a switch molecule, wherein the T cell transiently expresses the switch molecule, wherein the T cell transiently expresses the switch molecule and interaction the switch molecule with its respective ligand induces the T cell to secrete an activation factor at a target site.

The present invention also includes modified T cells with switch molecules, soluble fusion proteins, and bispecific antibodies. In one aspect, the invention includes a modified T cell comprising a nucleic acid encoding a switch molecule comprising an extracellular domain comprising a membrane receptor or fragment thereof, and an intracellular domain comprising a signaling receptor or fragment thereof; and at least one of a nucleic acid encoding a soluble fusion protein and a nucleic acid encoding a bispecific antibody comprising bispecificity for an antigen on a target cell and an antigen on an activating T cell, wherein the T cell transiently expresses the switch molecule and secretes the soluble fusion protein or the bispecific antibody.

In another aspect, the invention includes a population of modified T cells comprising a nucleic acid encoding a switch molecule and at least one of a nucleic acid encoding a soluble fusion protein and a nucleic acid encoding a bispecific antibody, wherein the T cells transiently expresses the switch molecule and secretes the soluble fusion protein or the bispecific antibody.

In one embodiment, the modified T cell is activated by binding the switch molecule to a ligand and activation induces the T cell to secrete an activation factor at a target site. In another embodiment, the modified T cell is activated by binding to the bispecific antibody and activation induces the T cell to secrete an activation factor at a target site.

The target site may include a tumor, such as a solid tumor. In one embodiment, the T cell homes to a solid tumor. Examples of tumors include brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, thyroid cancer, and combinations thereof.

The T cell may home to a specific antigen. For example, the T cell may home to a tumor antigen. In one embodiment, the T cell may bind a tumor antigen. The tumor antigen may be a tumor associated antigen (TAA), a viral antigen, an antibody-recognized antigen, any fragment thereof, or any combination thereof. In another embodiment, the tumor antigen may be p53, Ras, beta-Catenin, CDK4, alpha-Actinin-4, Tyrosinase, TRP1/gp75, TRP2, gp100, Melan-A/MART1, Gangliosides, PSMA, HER2, WT1, EphA3, EGFR, CD20, MAGE, BAGE, GAGE, NY-ESO-1, Telomerase, Survivin, or any combination thereof.

In another aspect, the invention includes a population of modified T cells comprising an electroporated nucleic acid encoding a switch molecule, wherein the T cells transiently express the switch molecule and interaction of the switch molecule with its respective ligand induces the T cells to secrete an activation factor at a target site. Another aspect of the invention includes a method for generating a T cell transiently expressing a switch molecule. The method includes introducing a nucleic acid encoding a switch molecule into a population of T cells, wherein the switch molecule comprises an extracellular domain comprising a membrane receptor or fragment thereof selected from the group consisting of a cytokine receptor, a chemokine receptor, a growth factor receptor, a hormone receptor, and other signaling receptor; and an intracellular domain comprising a signaling receptor or fragment thereof, and wherein the T cells transiently express the switch molecule and interaction of the extracellular domain of the switch molecule with its respective ligand induces the T cells to secrete an activation factor at a target site, thereby generating the T cell. In one embodiment, the method further includes activating the T cells to home to a target site, wherein the T cells secrete the activation factor at the target site.

In yet another aspect, the invention includes a method for generating a T cell transiently expressing a switch molecule and a soluble fusion protein or a bispecific antibody. The method includes introducing a nucleic acid encoding a switch molecule comprising an extracellular domain comprising a membrane receptor or fragment thereof and an intracellular domain comprising a signaling receptor or fragment thereof and at least one of a nucleic acid encoding a soluble fusion protein and a nucleic acid encoding a bispecific antibody comprising bispecificity for an antigen on a target cell and an antigen on an activating T cell. In one an aspect, the T cells can transiently express the switch molecule and soluble fusion protein or bispecific antibody and activation of the T cells induces secretion of an activation factor at a target site.

Sources of T Cells

Prior to introduction of the nucleic acid encoding the switch molecule, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In one embodiment, the source of the T cells is peripheral blood mononuclear cells. In another embodiment, the population of cells comprises purified T cells.

In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells or any of the other source of cells comprising T cells can be depleted of non-T cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of cells may include peripheral blood mononuclear cells, cord blood cells, a purified population of T cells, and a T cell line. In another embodiment, the population of cells comprises peripheral blood mononuclear cells. In yet another embodiment, the population of cells comprises purified T cells.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, New York); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA

In one embodiment, RNA is introduced into T cells. In another embodiment, the nucleic acids are mRNA, such as in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a secretable factor. By way of example, the template encodes an antibody, a soluble cytokine, a soluble chemokine, a growth factor, or a functional fragment or variant thereof.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the nucleic acid encoding the switch molecule is mRNA. In one embodiment, nucleic acid encoding the switch molecule is in vitro transcribed mRNA. In another embodiment, the nucleic acid is electroporated into the cells. In yet another embodiment, the mRNA is electroporated into the cells.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the switch molecule mRNAs with different structures and combination of their domains. For example, including multiple switch molecule in the same cell allows secretion of multiple activation factors that may activate T cells, enhance T cell function or modulate other target cells' immune responses toward diseased cells.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993, 434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Activating and Expanding T Cells

When the T cell is activated prior to introduction to the nucleic acids, co-stimulatory molecules on the T cell may be activated. Examples of activating the T cell may include stimulating CD3 and/or CD28, such as through antibodies to CD3 and/or CD28. The medium used to culture the T cells may include an agent that can activated the T cells. For example, an agent that can stimulate CD3 is an antibody to CD3, and an agent that can stimulate CD28 is an antibody to CD28.

In another embodiment, the T cell may be activated and/or expanded prior to introduction of the nucleic acid. Generally, the T cells may be expanded by contact with a surface having attached thereto an agent that stimulates a CD3/TCR complex associated signal and a ligand that stimulates a co-stimulatory molecule on the surface of the T cells. Alternatively, T cells may be expanded through culturing or other methods such that the T cells contained within a population.

In one aspect, the method of generating the T cells can further comprise isolating the T cells and a subsequent electroporation followed by culturing. Following isolation, the T cells can be incubated in cell medium in a culture apparatus for a period of time or until the cells reach confluency or high cell density for optimal passage before passing the cells to another culture apparatus. The culturing apparatus can be any culture apparatus commonly used for culturing cells in vitro. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately for nucleic acid introduction or cryopreserved to be stored for use at a later time. In one embodiment, the method further comprises cryopreserving the T cells before introduction of the nucleic acid. In another embodiment, the method further comprises cryopreserving the T cells. In yet another embodiment, the cryopreserved T cells are thawed before introduction of the switch molecule nucleic acid, formulation into a composition to transiently express the switch molecule and secrete the activation factor, or administration to a subject.

The cells can be ex vivo expanded using a method described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-2, IL-3 and c-kit ligand, for example as those described in Dudley et al., J. Immunol., 26(4):332-342, 2003, for a Rapid Expansion Protocol (REP). In one embodiment, expanding the T cells comprises culturing the T cells with a factor selected from the group consisting of flt3-L, IL-1, IL-3 and c-kit ligand.

The culturing step as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In another embodiment, the method of generating the T cells can further comprise isolating the electroporated T cells for further applications. In yet another embodiment, the method of generating the T cells can further comprise a subsequent electroporation of the electroporated T cells followed by culturing. The subsequent electroporation may include electroporating a mRNA encoding an additional switch molecule or an agent that stimulates the T cell. The agent may stimulate the T cell, such as by stimulating further expansion, effector function, or another T cell function. In one embodiment, the agent mRNA is co-electroporated with the switch molecule mRNA. In another embodiment, the T cell is serially electroporated with mRNA for the switch molecule, then mRNA for the agent. In yet another embodiment, the T cell is cultured or allowed a recovery time between the electroporation steps.

In another embodiment, the method further comprises stimulating the electroporated T cells with at least one co-stimulatory molecule selected from the group consisting of CD3, CD27, CD28, CD83, CD86, CD127, 4-1BBL and PD1.

Therapy

The T cells described herein may be included in a composition for therapy. The composition may include a pharmaceutical composition and further include a pharmaceutically acceptable carrier. A therapeutically effective amount of the pharmaceutical composition comprising the T cells may be administered.

In one aspect, the invention includes a method for delivering a factor to a target site, the method comprising introducing a nucleic acid encoding a switch molecule into a population of cells comprising modified T cells, wherein the switch molecule comprises an extracellular domain comprising a membrane receptor or fragment thereof selected from the group consisting of a cytokine receptor, a chemokine receptor, a growth factor receptor, a hormone receptor, and other signaling receptor; and an intracellular domain comprising a signaling receptor or fragment thereof; and administering the population of cells to a subject in need thereof, wherein the T cells transiently express the switch molecule and interaction of the extracellular domain of the switch molecule with its respective ligand induces the T cells to secrete an activation factor at the target site.

In such an aspect, the population of cells may include any of a peripheral blood mononuclear cells, cord blood cells, a purified population of T cells, and a T cell line. The T cells in the population may also be activated and expanded as described herein.

In another aspect, the invention includes a method for delivering a factor to a target site, the method comprising administering a population of cells to a subject in need thereof, wherein the T cells transiently express a switch molecule, wherein the switch molecule comprises an extracellular domain comprising a transforming growth factor-beta receptor (TGF-beta-R) or fragment thereof and an intracellular domain comprising a IL-12R or fragment thereof, and wherein interaction the extracellular domain of the switch molecule with its respective ligand induces the T cells to secrete an activation factor at the target site.

In yet another aspect, the invention includes a method for delivering a factor to a target site, the method comprising administering a population of cells to a subject in need thereof. T cells of the method transiently express a switch molecule, wherein the switch molecule comprises an extracellular domain comprising a transforming growth factor-beta receptor (TGF-beta-R) or fragment thereof and an intracellular domain comprising a IL-12R or fragment thereof. The interaction of the extracellular domain of the switch molecule with its respective ligand induces the T cells to secrete an activation factor at the target site. In yet another aspect, the invention includes a method for delivering a factor to a target site. The method includes administering a population of cells comprising T cells to a subject in need thereof. The T cells home to the target site and transiently express a switch molecule comprising an extracellular domain comprising a membrane receptor or fragment thereof and an intracellular domain comprising a signaling receptor or fragment thereof and a bispecific antibody comprising bispecificity for an antigen on a target cell and an antigen on an activating T cell. The method further includes activating the T cells at the target site, wherein the T cells are induced to secrete an activation factor. In one embodiment, activating the T cells comprises binding a ligand to the extracellular domain of the switch molecule. In another embodiment, activating the T cells comprises binding the bispecific antibody to the activating T cell antigen on the T cells.

In another aspect, the invention includes a method of treating a disease or condition comprising administering population of modified T cells comprising a nucleic acid encoding a switch molecule. In an exemplary embodiment, the T cells comprise a nucleic acid encoding a switch molecule comprising an extracellular domain comprising a membrane receptor or fragment thereof selected from the group consisting of a cytokine receptor, a chemokine receptor, a growth factor receptor, a hormone receptor, and other signaling receptor; and an intracellular domain comprising a signaling receptor or fragment thereof, and wherein the T cells transiently express the switch molecule and interaction of the extracellular domain of the switch molecule with its respective ligand induces the T cells to secrete an activation factor at the target site. The T cells may be administered to induce lysis of the target cell or tissue.

In yet another aspect, the invention includes a method of treating a disease or condition. The method includes administering population of modified T cells comprising a nucleic acid encoding a switch molecule comprising an extracellular domain comprising a membrane receptor or fragment thereof and an intracellular domain comprising a signaling receptor or fragment thereof and a nucleic acid encoding a bispecific antibody comprising bispecificity for an antigen on a target cell and an antigen on an activating T cell. In such an aspect, the T cells transiently express the switch molecule and bispecific antibody and activation of the T cells induces secretion of an activation factor at the target site, thereby treating the disease or condition.

The T cells generated as described herein are generally uniform and possess T cell function. Further, the T cells can be administered to a mammal, preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease.

The modified T cells generated as described herein can also be used to treat a disease or condition that is an autoimmune disease. Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The modified T cells generated as described herein can also be used to treat a disease or condition that is an inflammatory disorder. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

The electroporated T cells generated as described herein can also be used to treat a disease or condition that is cancer, such as brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

In another embodiment, the T cells described herein may be used for the manufacture of a medicament for the treatment of a disease or condition in a subject in need thereof.

Cells of the invention can be administered in dosages and routes and at times to be determined in appropriate pre-clinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeneic or xenogeneic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

The cells described herein can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Pharmaceutical Compositions

Pharmaceutical compositions of the present invention may comprise a modified T cell or population of modified T cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer modified T cells to a subject and then subsequently redraw blood (or have an apheresis performed), activate T cells therefrom according to the present invention, and reinfuse the patient with these modified and activated T cells. This process can be carried out multiple times every few weeks. In certain embodiments, T cells can be activated from blood draws of from 10 ml to 400 ml. In certain embodiments, T cells are activated from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present invention, cells modified and activated using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the immune cells of the present invention. In an additional embodiment, T cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Construction of In Vitro Transcription (IVT) mRNA Vectors.

All the switch molecule for PD1-CD28, PD1-41BB and TGFbR-IL12R and Bis-RNAs were synthesized and/or amplified and assembled by PCR based on sequencing information provided from the relevant published patents. The PCR products were subcloned into pGEM.64A based vector by replacing GFP of pGEM-GFP.64A to produce pGEM.64A based vectors.

RNA In Vitro Transcription (IVT).

mMESSAGE mMACHINE® T7 Ultra (Ambion, Inc) was used to generates IVT RNA with Anti-Reverse Cap Analog (ARCA, 7-methyl(3'-O-methyl)GpppG)m7G(5')ppp (5')G). The IVT RNA products were purified using an RNeasy Mini Kit (Qiagen, Inc., Valencia, CA) and purified RNA was eluted in RNase-free water at 1-2 mg/ml.

RNA Electroporation of T Cells.

Purified resting T cells or CD3/CD28 Beads stimulated T cells were electroporated using BTX EM830 (Harvard Apparatus BTX, Holliston, MA, USA). The T cells subjected to electroporation were washed three times with OPTI-MEM (Invitrogen) and were re-suspended in OPTI-MEM at the final concentration of $1-3 \times 10^8$/ml. Subsequently, 0.1 ml of the cells was mixed with 10 µg IVT RNA (or as indicated) and electroporated in a 2-mm cuvette.

CAR Detection on Electroporated T Cells.

Cells were washed and suspended in FACs buffer (PBS plus 0.1% sodium azide and 0.4% BSA). Biotin-labeled polyclonal goat anti-mouse F(ab)2 antibodies (for murine scFv) or anti-human anti-F(ab)2 (for human scFv) (Jackson Immunoresearch, West Grove, PA) were added to the tube and the cells were incubated at 4° C. for 25 minutes and washed twice. The cells were then stained with phycoerythrin-labeled streptavidin (BD Pharmingen, San Diego, CA).

ELISA.

Target cells were washed and suspended at $10^6$ cells/mL in R10. One hundred thousand of each target cell type were added to each of 2 wells of a 96 well round bottom plate (Corning). Effector T cell cultures were washed and suspended at $10^6$ cells/mL in R10. One hundred thousand effector T cells were combined with target cells in the indicated wells of the 96 well plate. In addition, wells containing T cells alone were prepared. The plates were incubated at 37° C. for 18 to 20 hours. After the incubation, supernatant was harvested and subjected to an ELISA assay using standard methods (Pierce, Rockford, IL).

CD107a Staining.

Cells were plated at an E:T of 1:1 ($10^5$ effectors:$10^5$ targets) in 164 µl of complete RPMI medium in a 96 well plate. 20 µl of phycoerythrin-labeled anti-CD107a Ab (BD Pharmingen, San Diego, CA) was added and the plate was incubated at 37° C. for 1 hour before adding Golgi Stop and incubating for another 2.5 hours. After 2.5 hours 10 µl FITC-anti-CD8 and APC-anti-CD3 was added and incubated at 37° C. for 30 min. After incubation, the samples were washed once with FACS buffer. Flow cytometry acquisition was performed with a BD FacsCalibur (BD Biosciences), and analysis was performed with FlowJo (Treestar Inc, Ashland, OR).

CFSE Based T Cells Proliferation Assay.

T cells at concentration of $10 \times 10^6$/mL in PBS were labeled with CFSE at 3 µM for 3 min 30 sec at room temperature. The labeling was stopped 5% FBS (in PBS) and washed twice with R10 and cultured in R10 with 10 IU/ml IL2. After overnight culture, the CFSE labeled T cells were electroporated. Two to four hours after electroporation, the T cells were stimulated with irradiated tumor or K562 cell lines at T:stimulator at 1:1. CFSE dilution was examined by flow cytometry and cell number was counted at the time as indicated.

The Results of the experiments disclosed herein are now described.

TGF beta receptor I and TGF beta receptor II extracellular and transmembrane domains were fused with IL-12 receptor b1 and b2 intracellular domains, respectively, to generate TGFbR-IL-12R1 TGFbR-IL-12R2. These constructs were cloned into pGEM.64A based RNA in vitro transcription vector. See FIG. 1.

Figure 2:
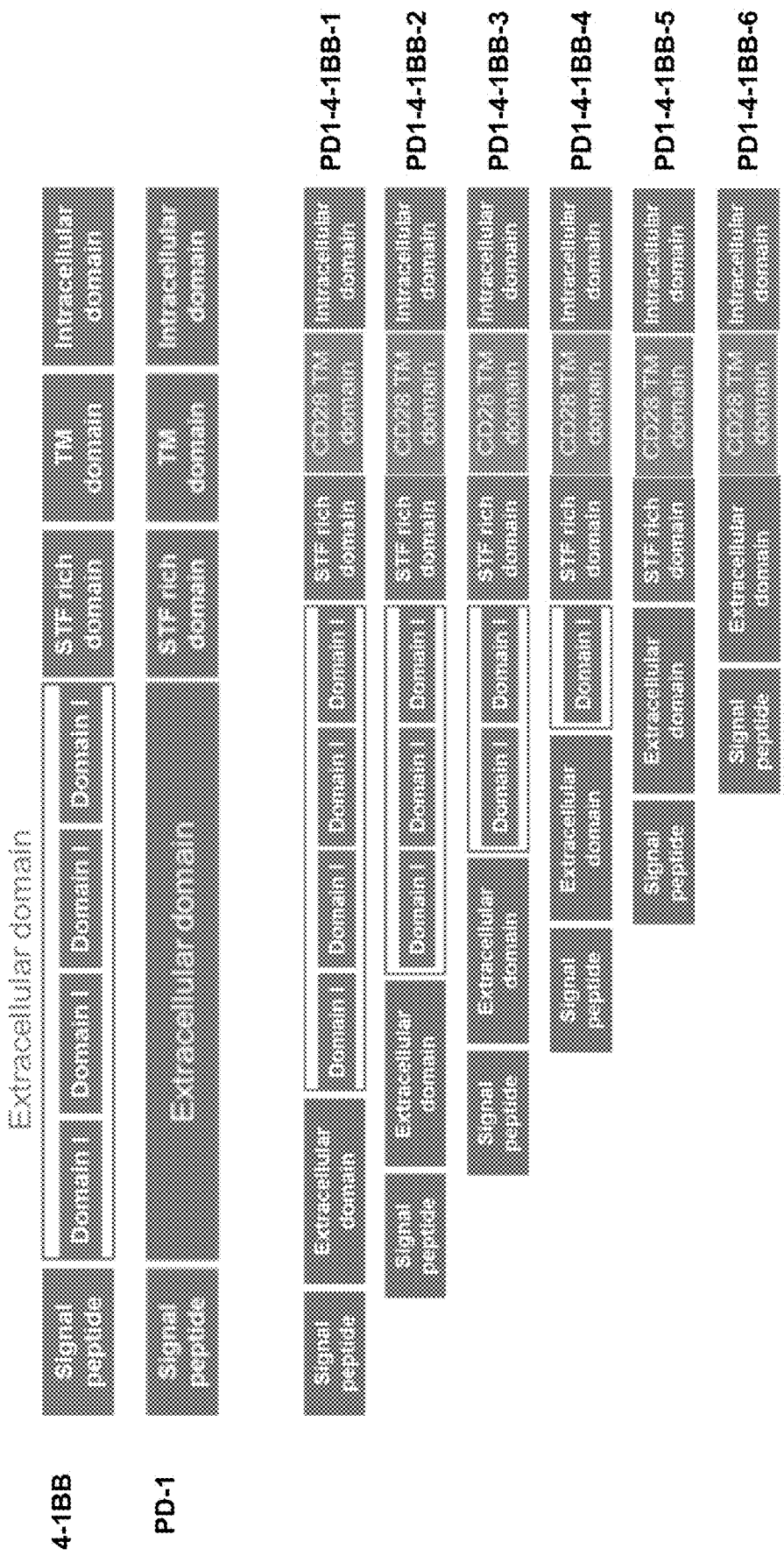
FIG. 2 shows an illustration of the PD1 to 4-1BB switch molecule RNA constructs that were electroporated into T cells.
Figure 3:
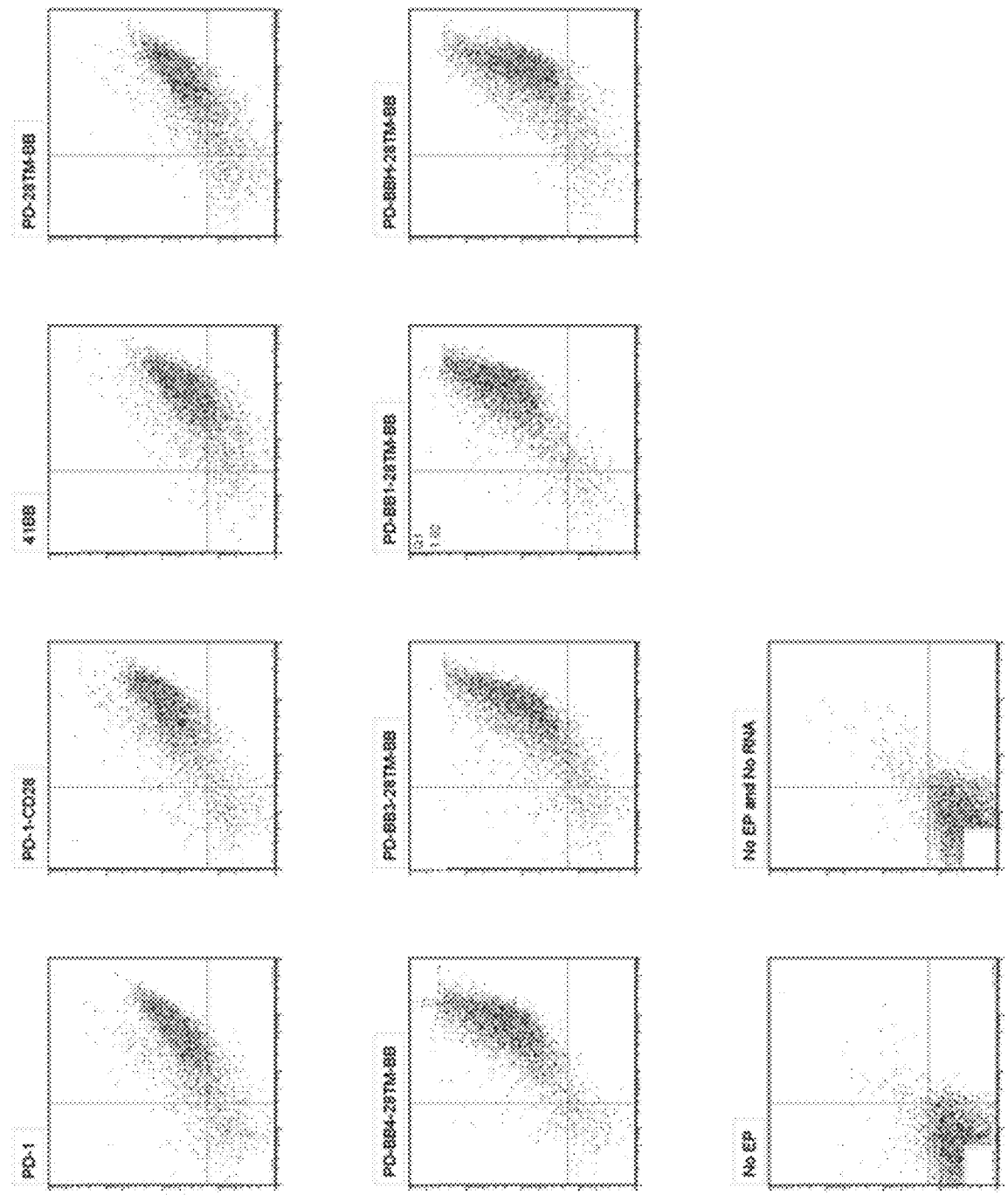
FIG. 3 is a panel of flow graphs showing expression of PD1 switch molecule and CAR expression in T cells after PD1-4-1BB switch molecule and CD19 CAR RNA co-electroporation into T cells.

Multiple PD1 and 4-1BB switch molecules, as listed in FIG. 2, were constructed based on the structure of the 4-1BB extracellular domains. PD1-41BB switch molecules and CAR molecules were detected in T cells co-electroporated with PD1-41BB and CD19Z RNA. PD1 switch molecule constructs, as listed in FIG. 2, were tested for their expression co-electroporating the switching molecule RNA with CD19Z RNA. See FIG. 3.

Figure 4:
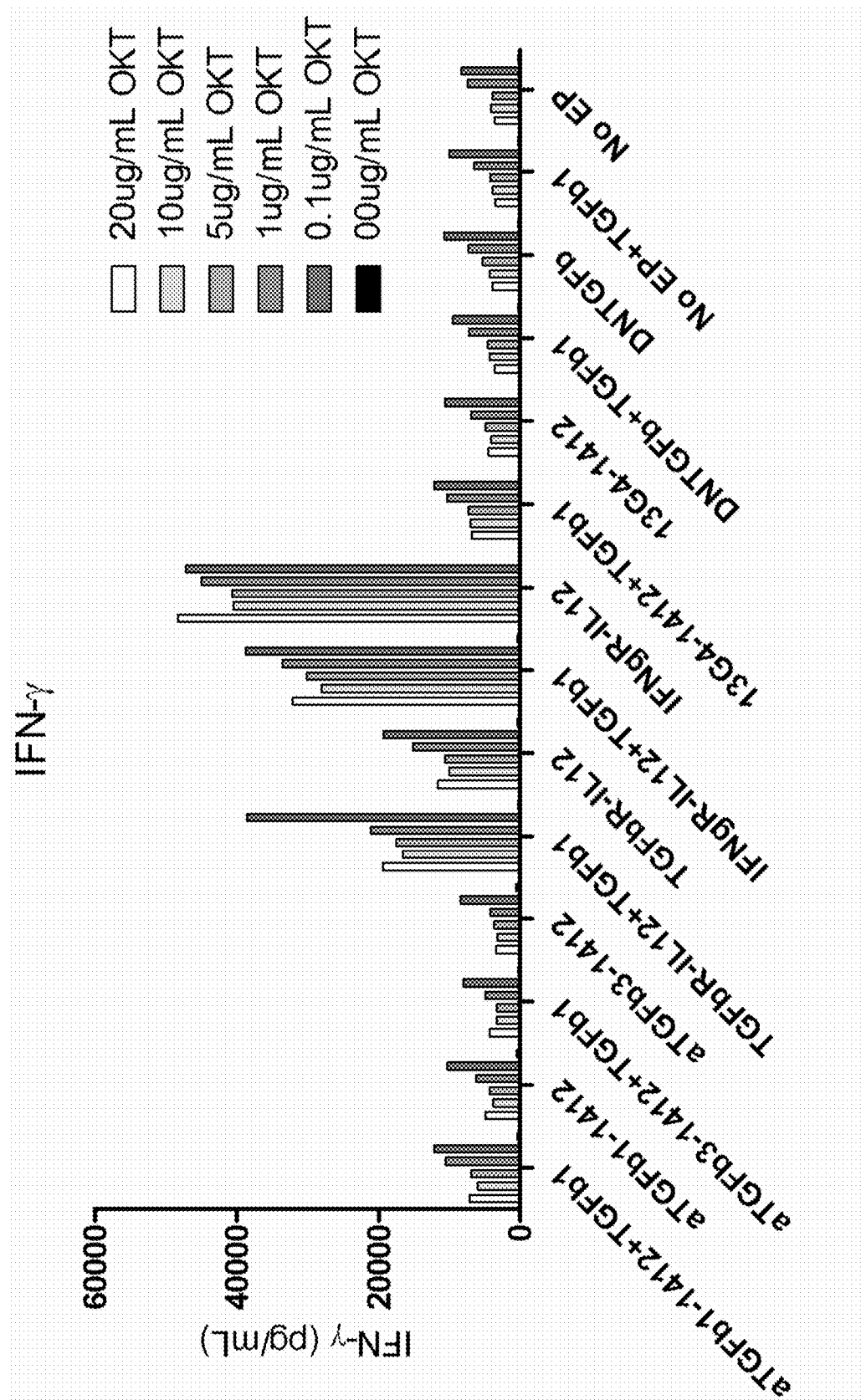
FIG. 4 is a graph showing IFN-gamma secretion of OKT3 stimulated, TGF-bR-IL-12R switch molecule RNA electroporated T cells. IL-12 signaling was induced by electroporation of TGFbR-IL-12R switch molecule RNA into T cells.

TGF beta signaling was switched to IL-12 signaling in both T and NK cells. T cells were electroporated with 5 μg RNA as indicated and stimulated with different amounts of OKT3 antibody with or without adding 10 ng/ml TGF-beta1. IFN-gamma secretion was assayed by ELISA after overnight stimulation. IFNgR-IL-12R switch molecule was used as positive control (FIG. 4). CD56+NK cells isolated from normal PBMC donor were electroporated with RNA as indicated and stimulated with K562 with or without adding 10 ng/ml TGF-beta1. IFN-gamma secretion was assayed by ELISA after 4 hrs stimulation. IFNgR-IL12R switch molecule was used as positive control (FIG. 4).

Figure 5:
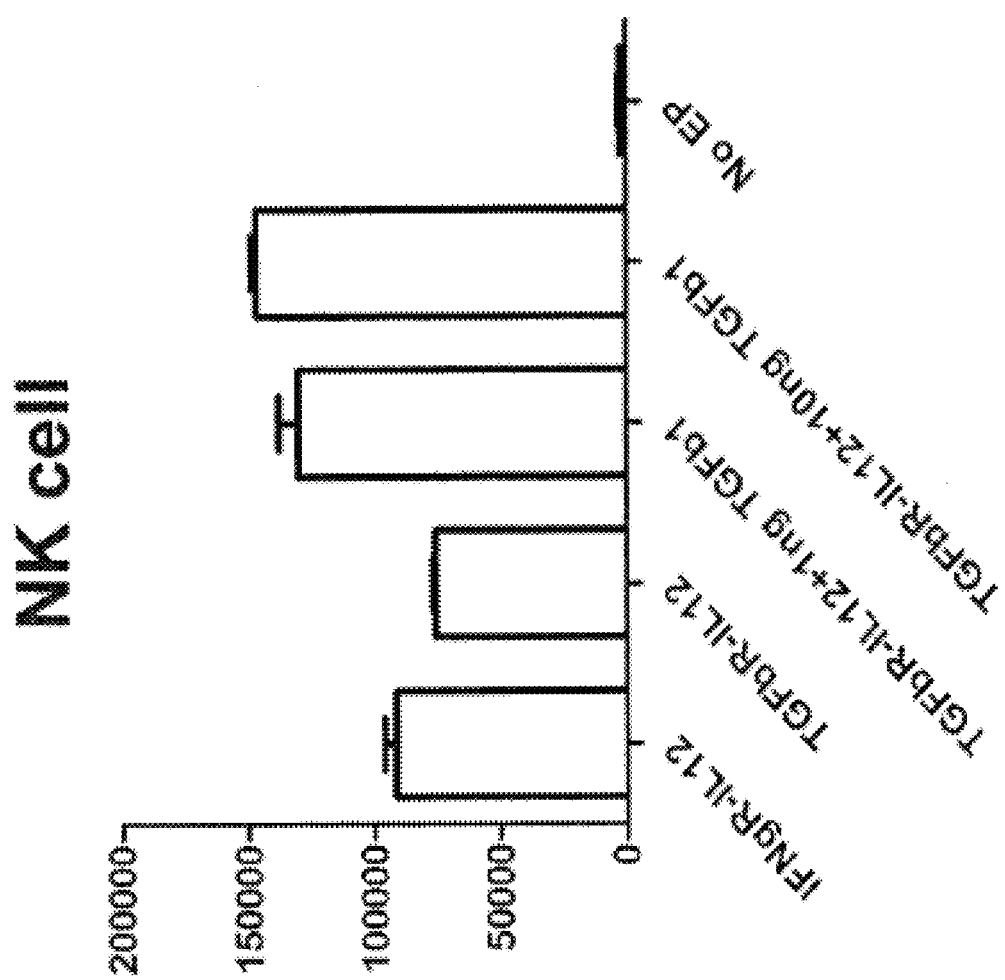
FIG. 5 shows IFN-gamma secretion of NK cells stimulated by K562. IL-12 signaling was induced by electroporating TGFbR-IL12R switch molecule RNA into NK cells.

IFN-gamma production in T cells that were electroporated with different TGFb switch molecules, stimulated with OKT3 antibody at different concentrations and cultured in the present of soluble TGFbeta. FIG. 4 shows increased IFN-gamma production in T cells with TGFbR-IL-12R in the present of TGFb (TGFbR-IL-12 and soluble TGFb), indicating that the TGFb signal was switched to an IL-12 signal resulting in increased IFN-gamma production. This was further confirmed by increased IFN-gamma secretion from NK cells that were electroporated with TGFbR-IL12R switch molecule in the present of TGFb (FIG. 5).

Figure 6:
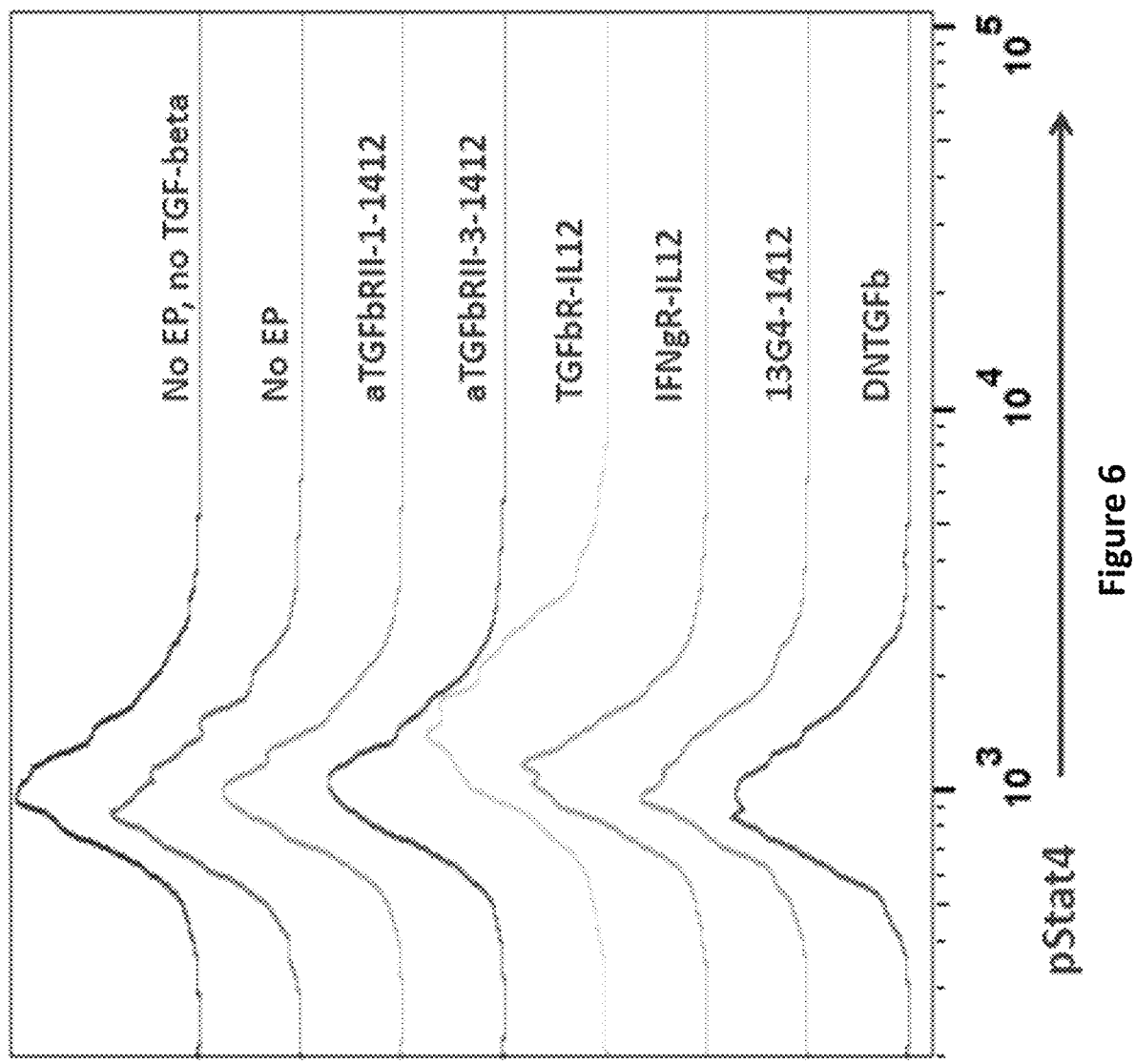
FIG. 6 is a graph showing the switch from TGFb to IL-12 signal activation by up-regulation of pStat4 after electroporating T cells with TGFbR-IL-12R switch molecule containing RNA constructs in the present of TGF beta.

Stat4 is a critical transcription factor for IL-12 signaling. It was found that only T cells electroporated with TGFbR-IL12R in the present of TGF-beta showed detectable phosphorylated Stat4 (pStat4) (FIG. 6). T cells were electroporated with 5 μg RNA as indicated. After 4 h, 10 ng/mL TGFb1 was added and 30 min later, pStat4 (IL-12 signal) was examined by intracellular staining of pStat4.

Figure 7:
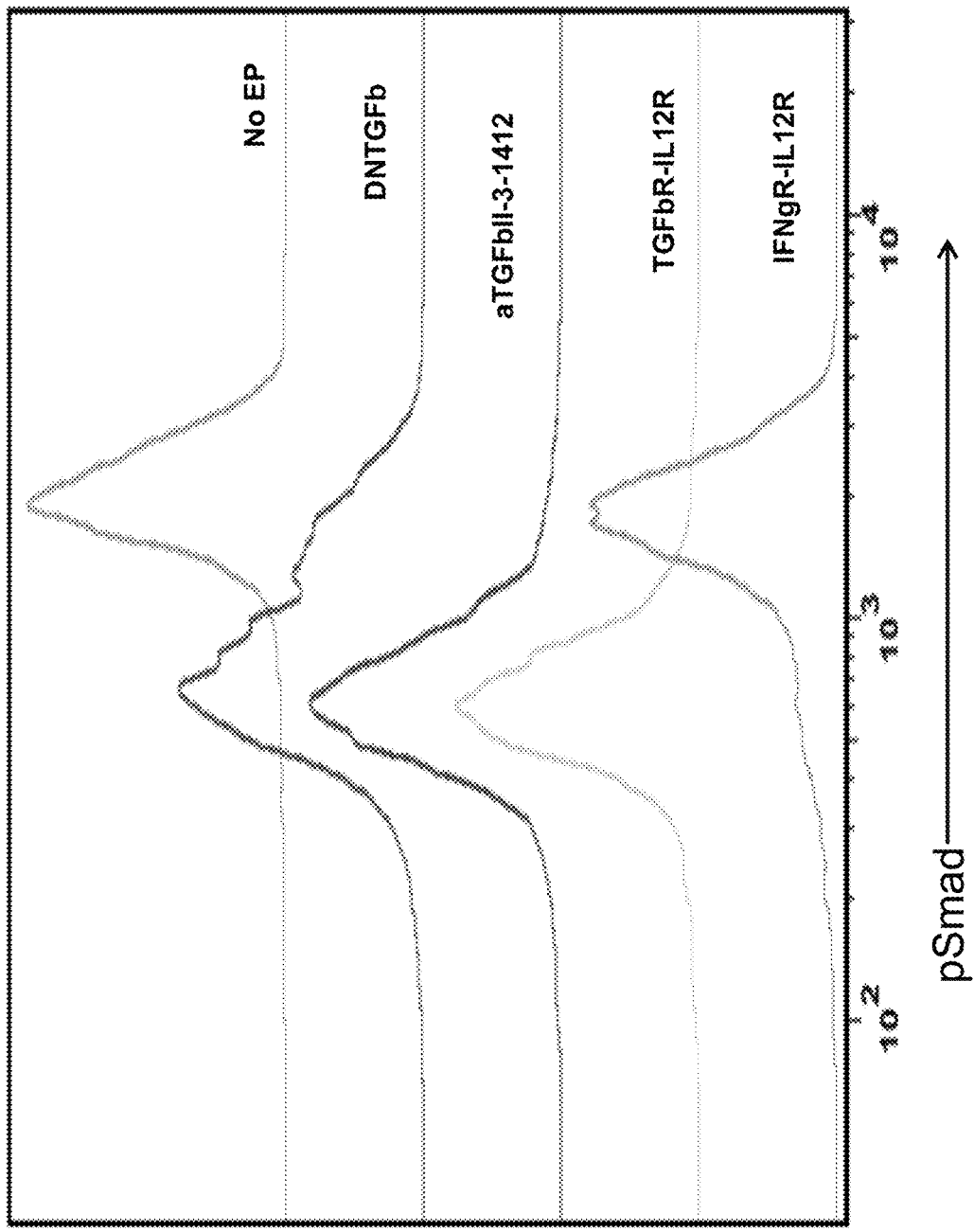
FIG. 7 is a graph showing the switch from TGFb to CD28 (aTGFbII-1412) and TGFb to IL-12 (TGFbR-IL-12R) signal by down-regulating pSmad of TGFb stimulated T cells after electroporating T cells with switch molecule RNA constructs. RNA for a dominant negative TGF-beta receptor (DNTGFb) was used as control.

To test if both TGFbR-IL-12R and aTGFbII-1412 negatively affect TGFbeta signal in T cells as dominant negative TGFbeta (DNTGFb), T cells were electroporated with RNA as indicated in FIG. 7 and stimulated with 5 ng/ml TGFb for 30 mins. Phosphorylated Smad (pSmad) was measured by flow cytometry. It was found that, compared with control RNA (IFNgR-IL-12R) and no electroporation (No EP), that pSmad was repressed for T cells electroporated with TGFbR-IL12R or TGFbII-3-1412, as well as T cells with dominant negative TGFb (DNTGFb). T cells with either TGFbR-IL-12R or aTGFbII-3-1412 showed significant decreased pSmad, suggesting that both of these switch molecules were not only switching TGFb signals to IL-12 or CD28, but also had the ability to serve as dominant negative molecules against TGFb.

Figure 8:
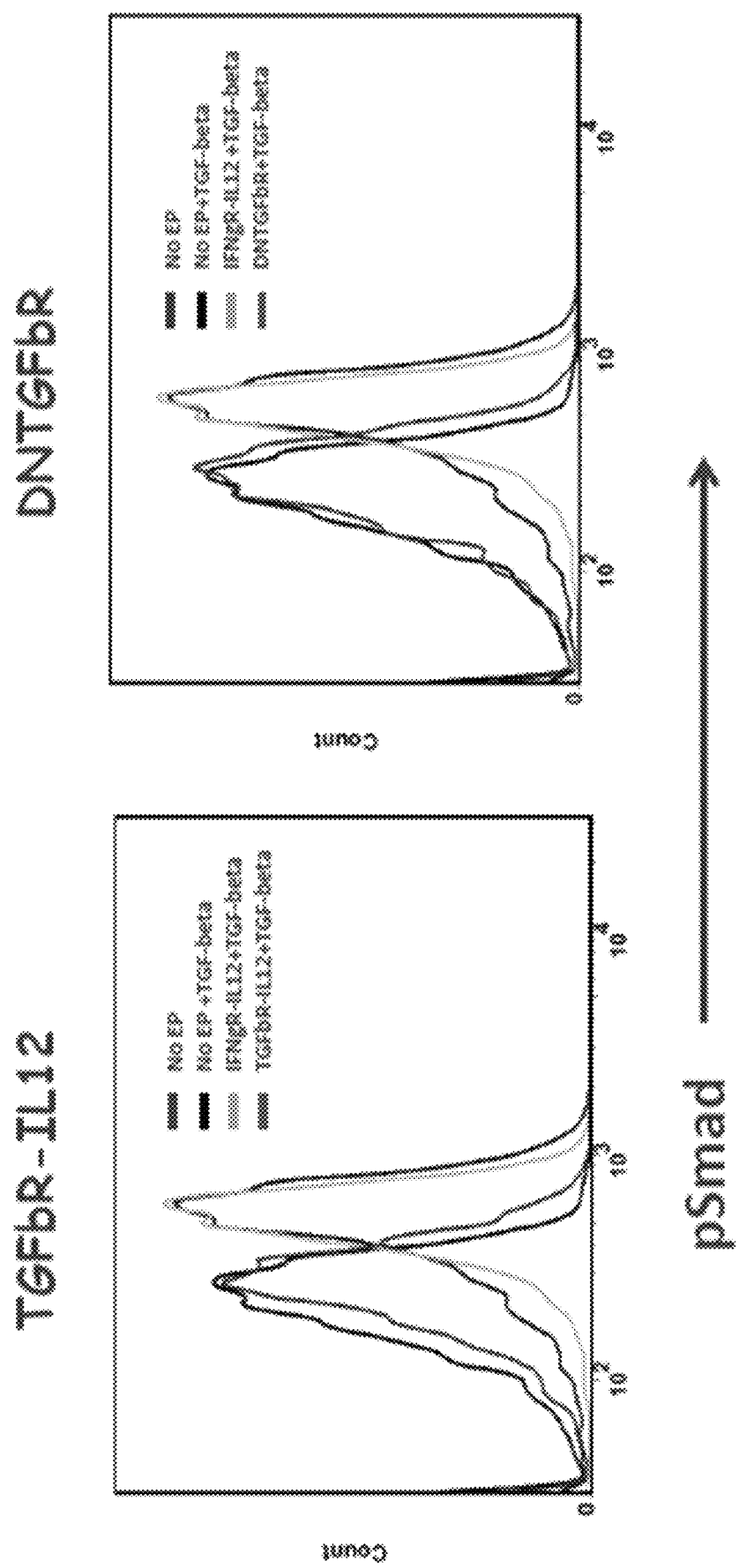
FIG. 8 is a panel of graphs showing TGFbR-IL-12R blocked TGF-beta signaling as efficiently as dominant TGFbRII (DNTGFbR).
Figure 9:
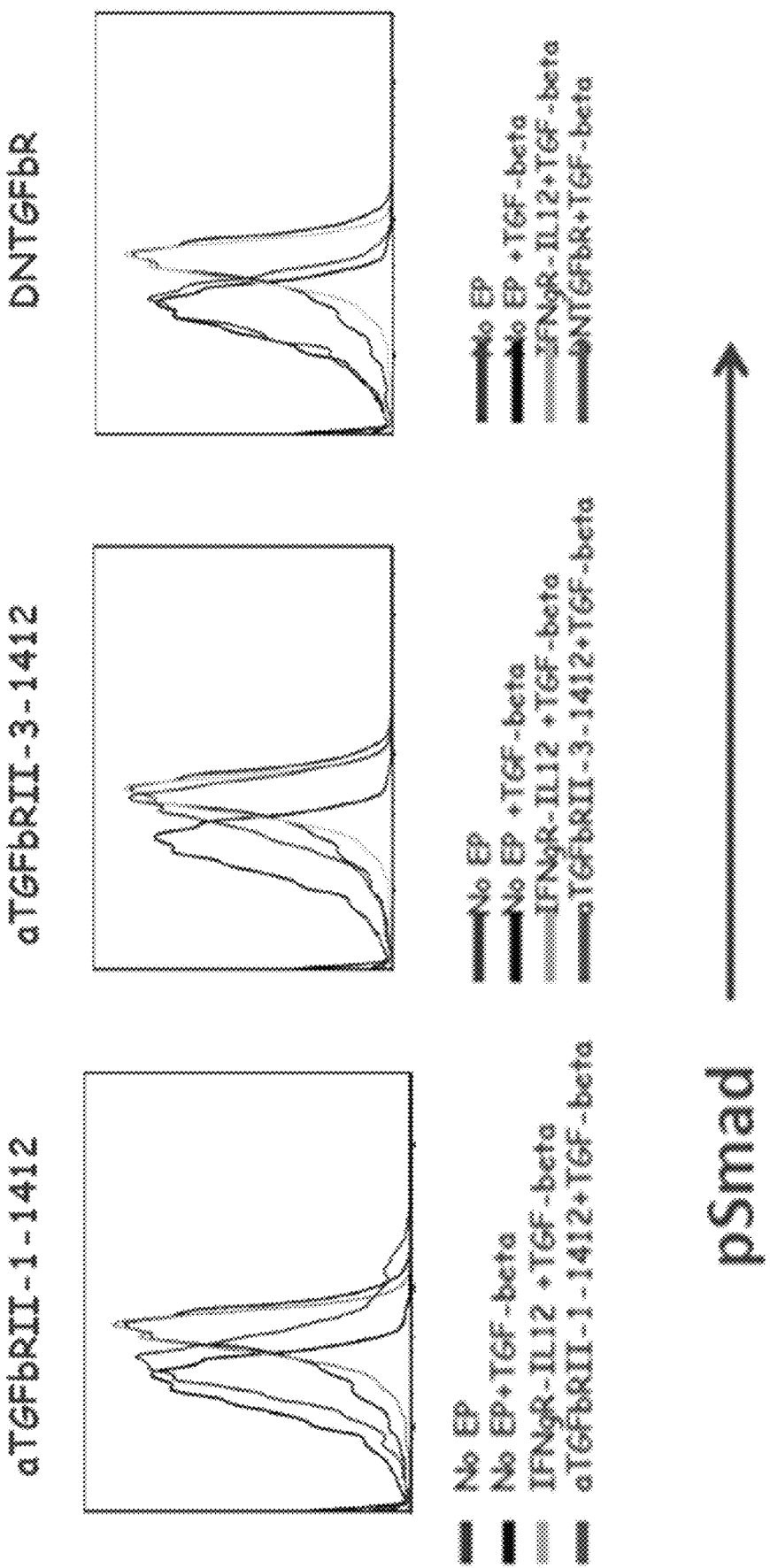
FIG. 9 is a panel of graphs showing bi-specific scFv TGFbR-CD28 (aTGFbRII-1-1412) blocked TGF-beta signaling as efficiently as dominant TGFbRII (DNTGFbR).

FIGS. 8 and 9 show that T cells electroporated with 5 ug RNA of TGFbR-IL-12R or 5 ug RNA of TGFbR-1412 blocked TGF-beta signaling as efficiently as dominant TGFbRII (DNTGFbR). After 4 h, 10 ng/mL TGFb1 was added and 30 min later, pSmad (TGF-beta signal) was examined by intracellular staining of pStat4. IFNgR-IL12R was used as control, showing up-regulated pSmad.

Figure 10:
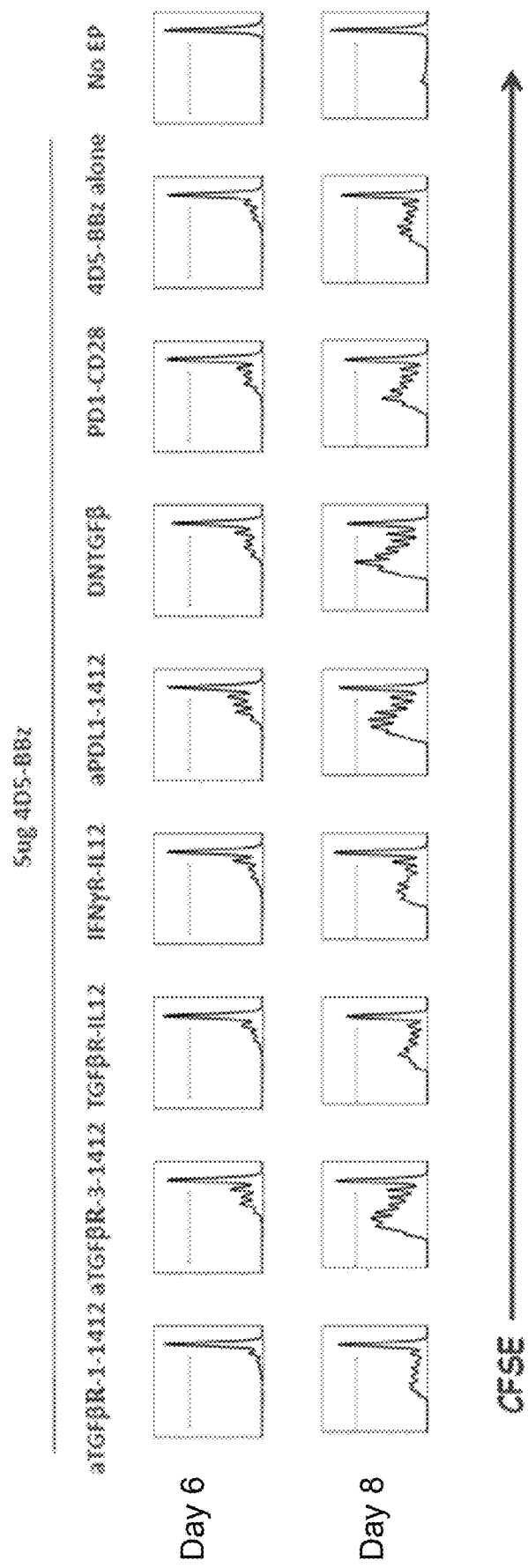
FIG. 10 is a panel of graphs showing increased resistance to Treg suppression of T cells expressing a TGFbR-CD28 switch molecule (aTGFbR-1-1412).

Regulatory T cells (Treg) play very important roles that negatively influence tumor immunity. Delivery molecules with anti-Treg activities by RNA electroporated T cells can potentially improve anti-tumor activity of adoptive transferred T cells by resisting Treg induction. T cells were labeled with CFSE and co-electroporated with a Her2 CAR (4D5-BBZ) and switch molecules as indicated. Four hours later, the electroporated T cells were stimulated with irradiated Her2/neu expressing K562 in the present of freshly isolated nature Treg at Teff:Treg=8:1. CFSE dilution was followed by using flow cytometry at day 6 and day 8 after stimulation. A significant T cell proliferation was induced by electoporating switch molecules, aTGFbII-3-1412 and TGFbR-IL12R. T cells showed increased resistance to Treg suppression of T cells expressing a aTGFbR-CD28 switch molecule (aTGFbR-1412) (FIG. 10).

Regulatory T cells (Tregs) were induced from sorted naïve T cells. Three different methods were used: 1.) Ab: Beads, 65 U/mL IL-2, 32 U/mL TGF-b1, 4500 U/mL IL-15, 10 ug/mL anti-IL-12, 20 ug/mL anti-IFN-g in X-Vivo-15 with 10% FBS. 2.) 20* Beads: Beads (20 beads: 1 cell), 20 U/mL IL-2, 2 ng/mL TGF-b1 in AIM-V. 3.) 1/10 beads: Beads (1 bead: 10 cells), 100 U/mL IL-2, 5 ng/mL TGF-b1+100 nM atRA in AIM-V with 10 mM Hepes buffer and streptomycin.

Figure 11:
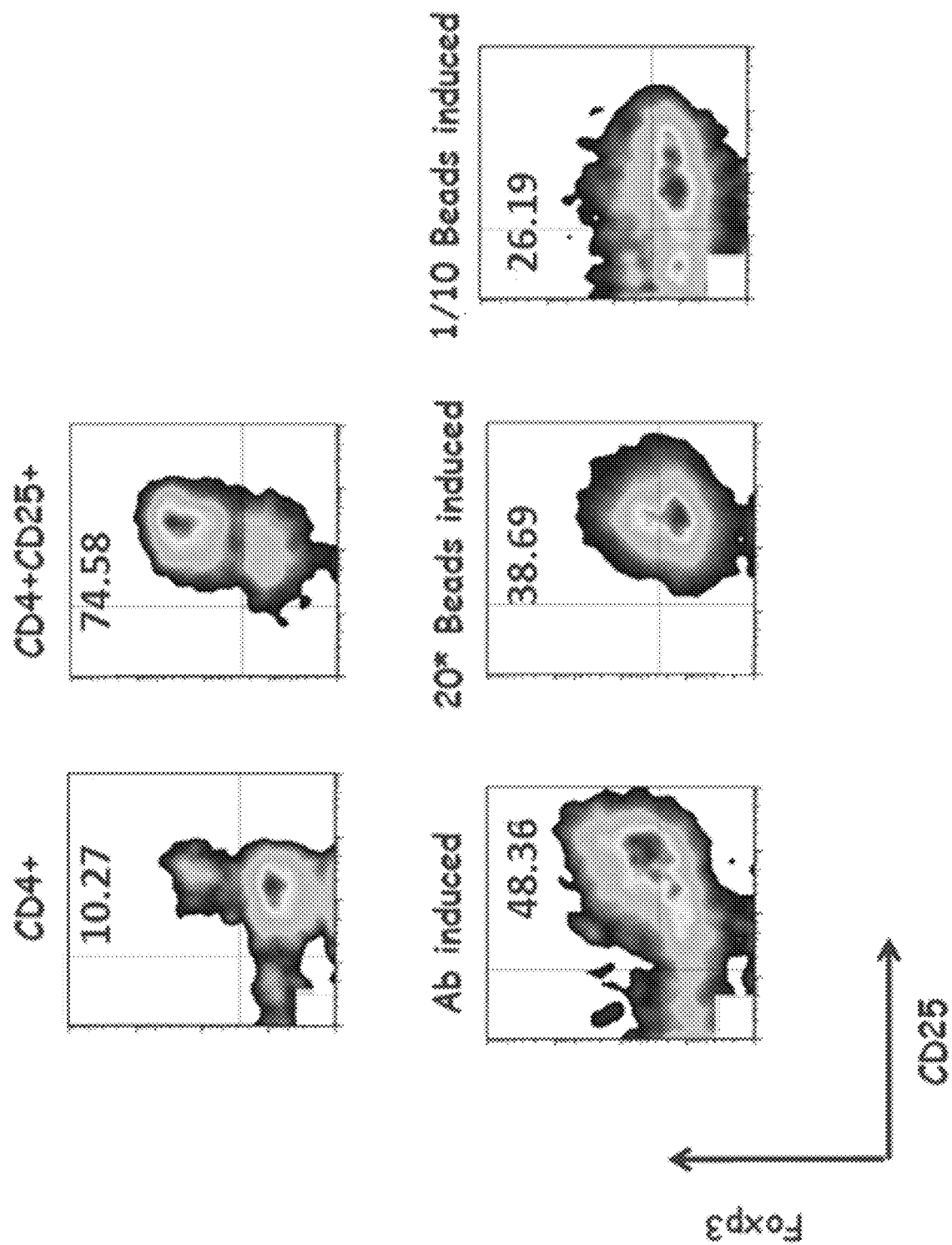
FIG. 11 is a panel of graphs showing Foxp3 expression in induced Tregs (iTregs).
Figure 12:
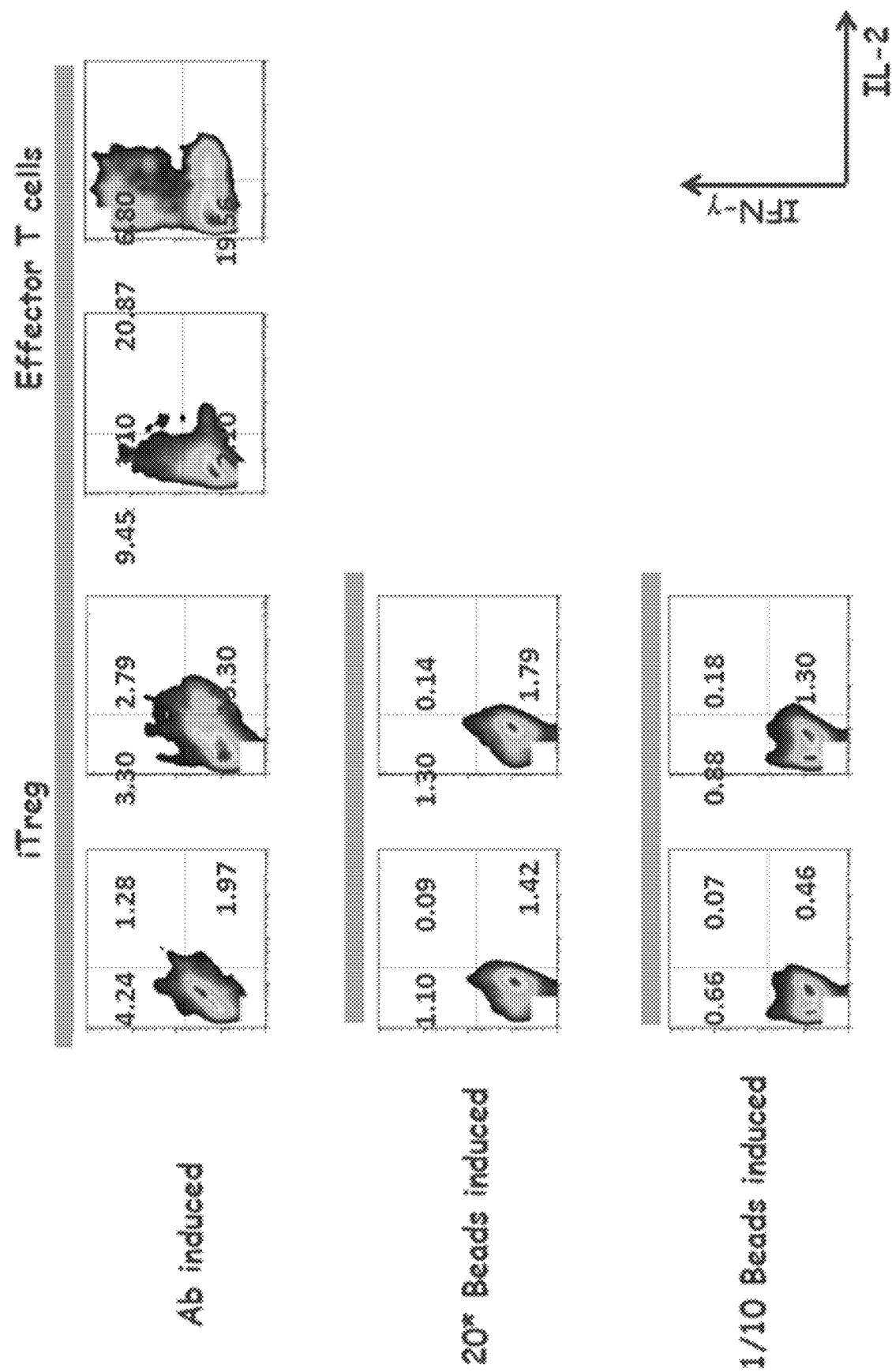
FIG. 12 is a panel of graphs showing decreased cytokine production of iTregs (PMA stimulation).
Figure 13:
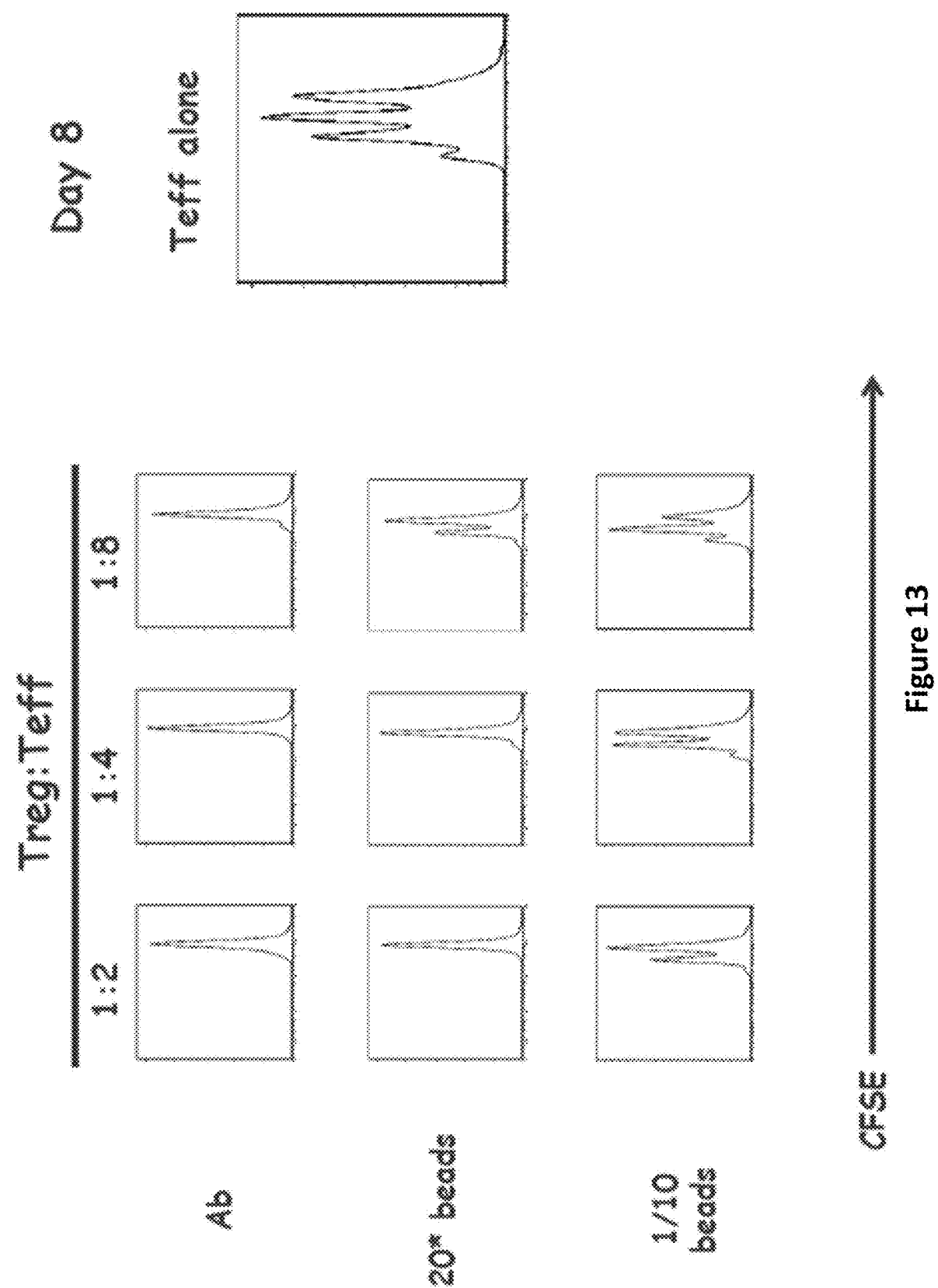
FIG. 13 is a panel of graphs showing suppression of proliferation of effector T cells (Teff) by iTregs.

FIG. 11 shows Foxp3 expression in induced Tregs (iTregs) and FIG. 12 shows decreased cytokine production of iTregs (PMA stimulation) in iTregs but not in effector cells. Proliferation of effector T cells (Teff) was also suppressed by iTregs (FIG. 13).

Figure 14:
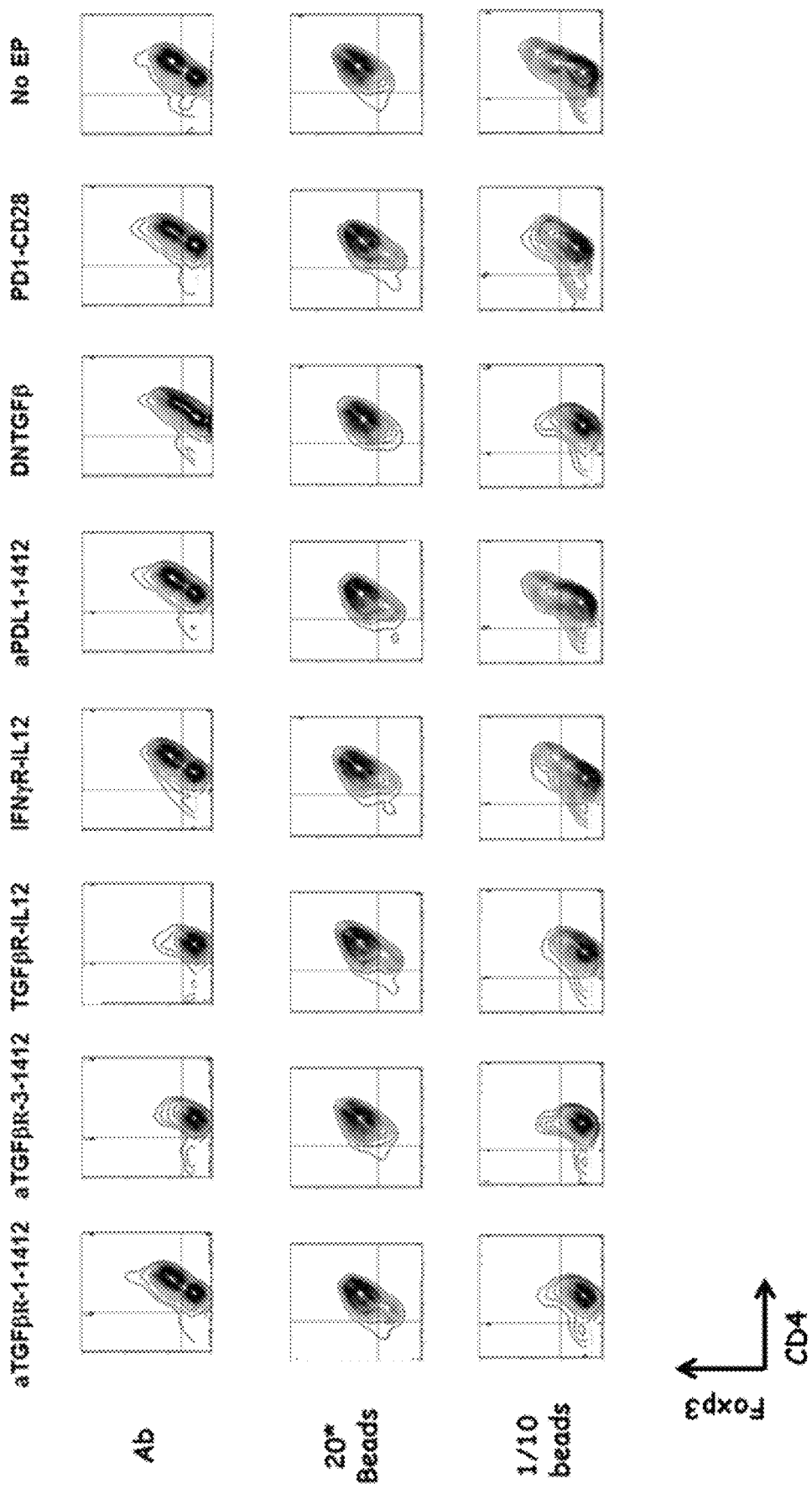
FIG. 14 is a panel of graphs showing reduced Treg induction for T cells expressing either aTGFbR-3-1412 or TGFbR-IL-12R as evidenced by decreased Foxp3 expression.
Figure 15:
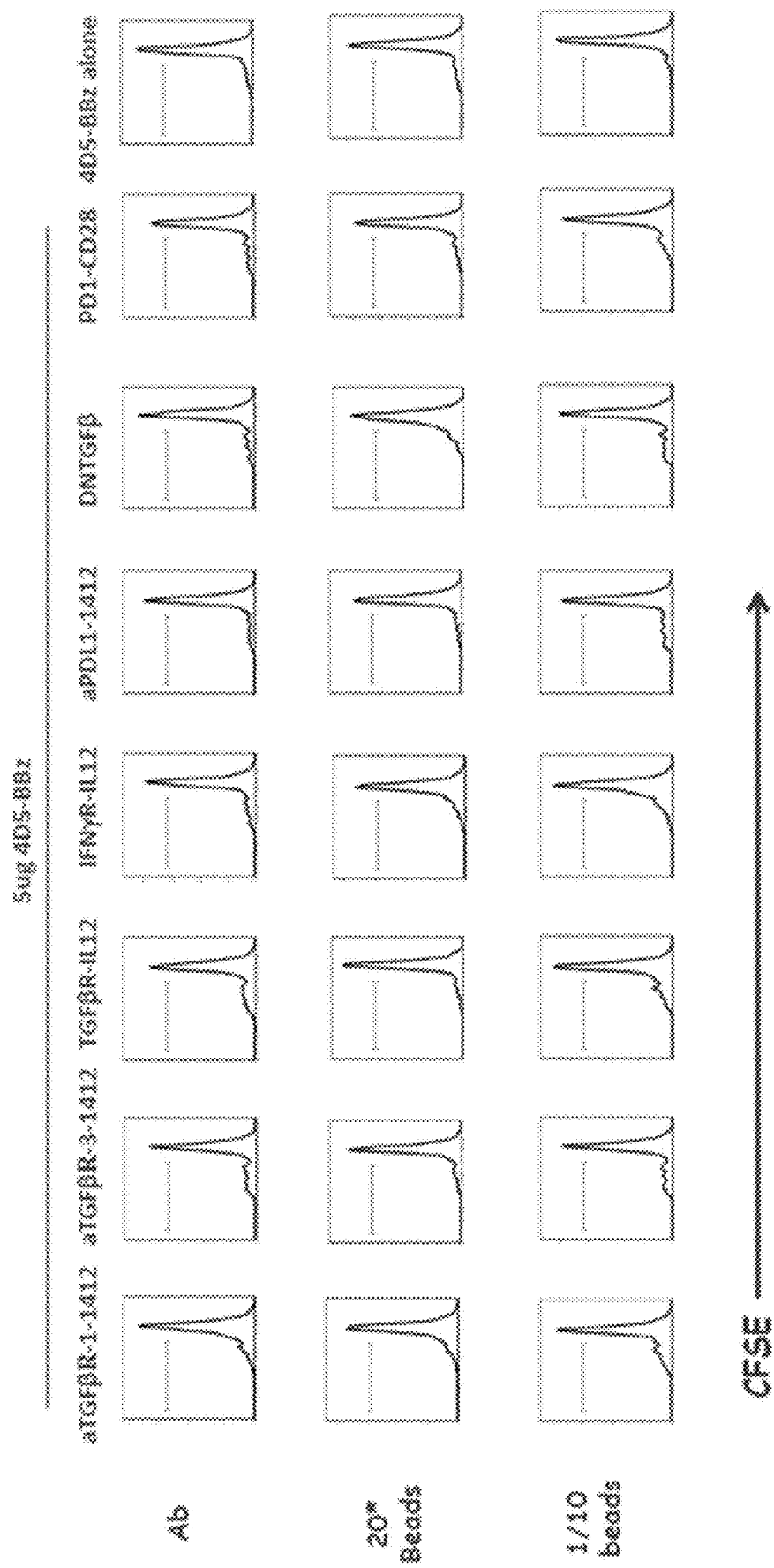
FIG. 15 is a panel of graphs showing reduced suppressive function of Tregs induced from T cells expressing either aTGFbR-3-1412 or TGFbR-IL-12R as evidenced by decreased Foxp3 expression.

Foxp3 expression was decreased (FIG. 14) which led to the reduced ability of suppressing T cell proliferation in a CFSE dilution assay (FIG. 15). Sorted Naïve CD4 T cells were electroporated with RNA as indicated and added to three different Treg inducing systems as indicated. 5 days later, Foxp3 expression was examined by flow cytometry. T cells were labeled with CFSE and co-electroporated with a her2 CAR (4eD5-BBZ) and switch molecules as indicated. Four hours later, the electroporated T cells were stimulated with irradiated Her2/neu expressing K562 in the present of day 5 Tregs induced from Naïve CD4 T cells transferred with RNA as indicated at Teff:Treg=8:1. CFSE dilution was followed by using flow cytometry at day 4 after stimulation.

Figure 16B:
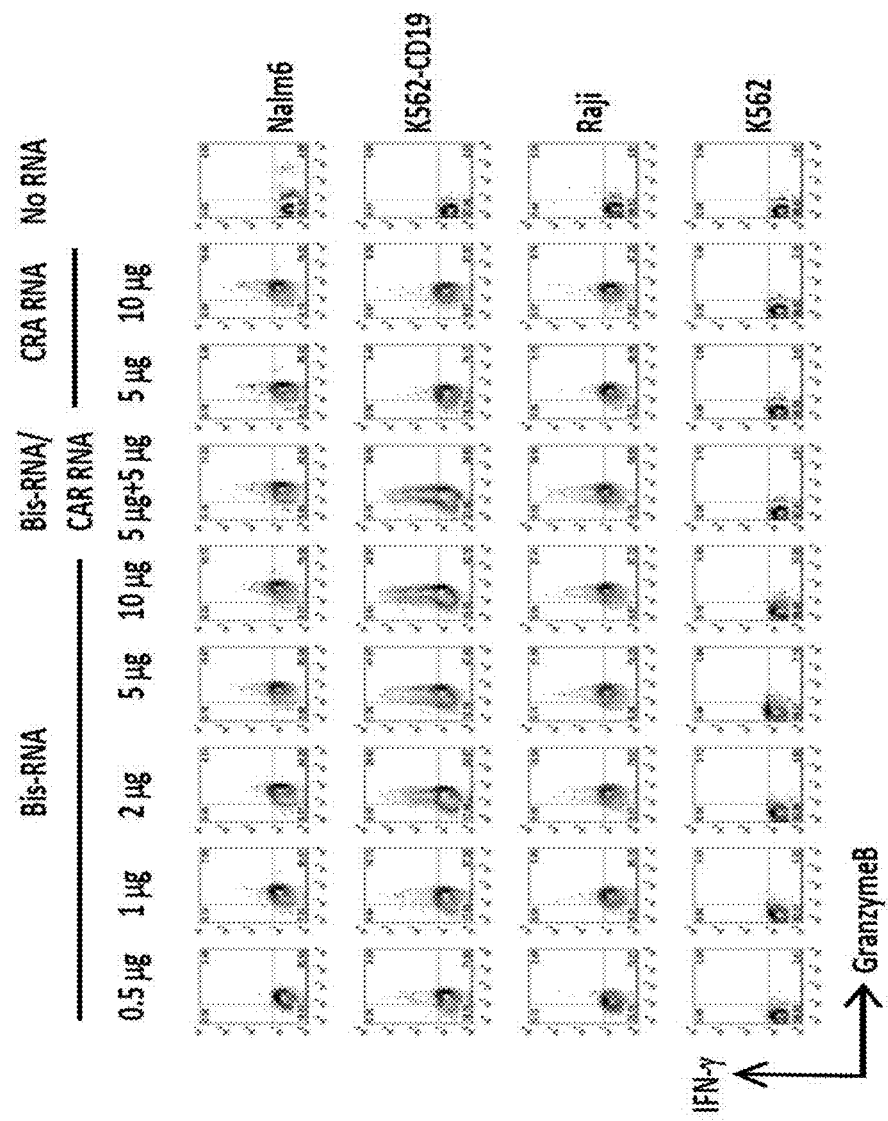
FIG. 16B is a panel of graphs showing IFN-gamma and Granzyme B expression after Bis-RNA electroporation. Eighteen hours after electroporation of the T cells described above, the electroporated T cells were subjected to intracellular staining of IFN-gamma and Granzyme B (FIG. 2B).

To test the sensitivity of Bis-RNA T cells for tumor recognition, T cells were electroporated with different doses of Bis-RNA and compared with CD19 CAR RNA. Similar results were obtained from CD107a up-regulation (FIG. 16A).

Figure 16C:
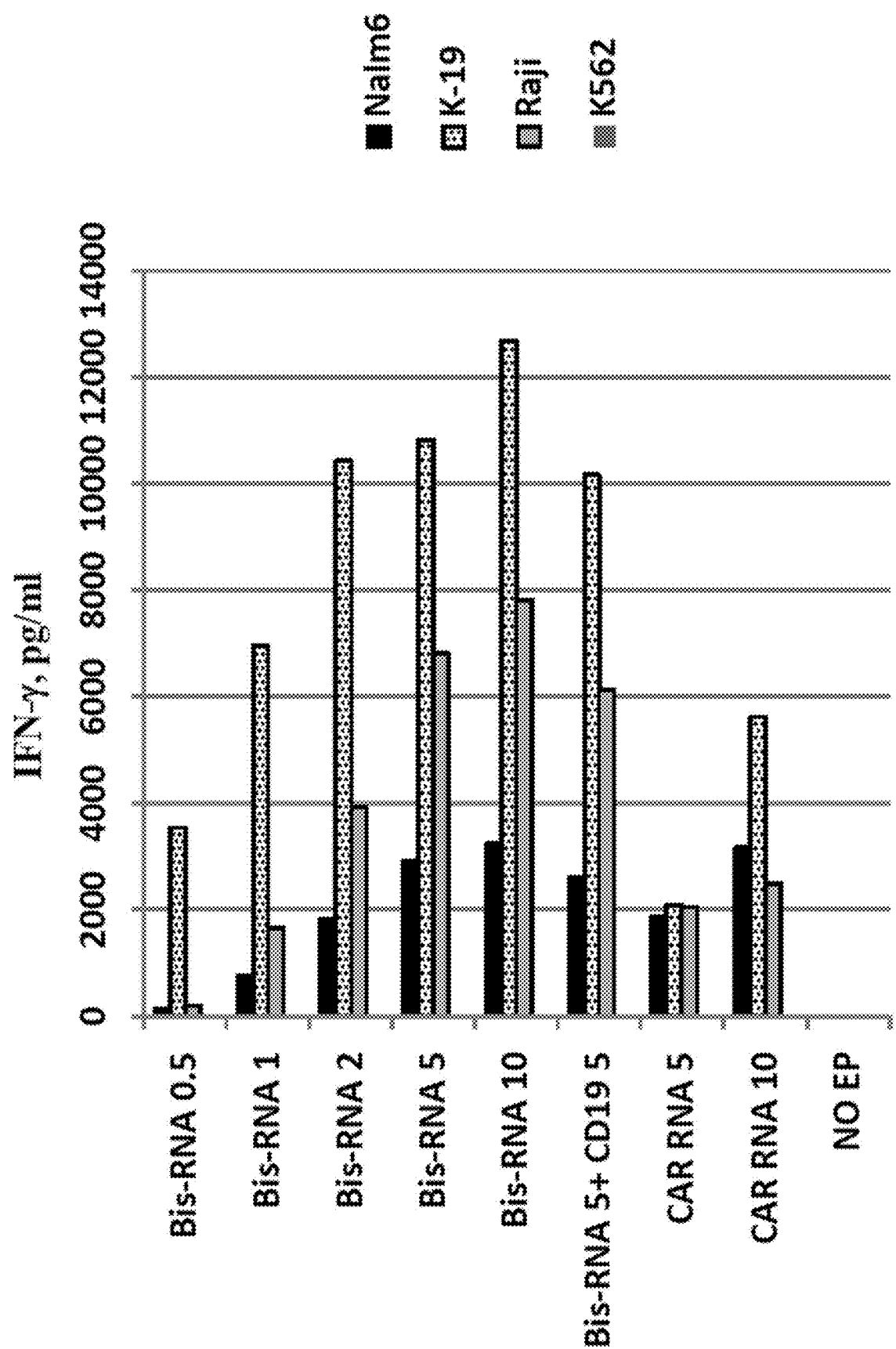
FIG. 16C is a graph showing ELISA detection of IFN-gamma. ELISA for IFN-gamma was performed after an overnight stimulation of the T cells with CD19 positive cells (Nalm6, K562-CD19 and Raji) or CD19 negative (K562) cell lines.

In the experiments of IFN-gamma/Granzyme B intracellular staining (FIG. 16B) and IFN-gamma production assayed by ELISA (FIG. 16C), significant T cell activation was observed when as low as 0.5 μg Bis-RNA was used. Yet, 1-2 μg of Bis-RNA remained comparable to 5-10 μg CD19 CAR RNA. Despite the Bis-RNA being at 0.5 μg in the low dose, Bis-RNA T cells and co-incubated GFP-RNA T cells still showed efficient anti-tumor activities.

Figure 16D:
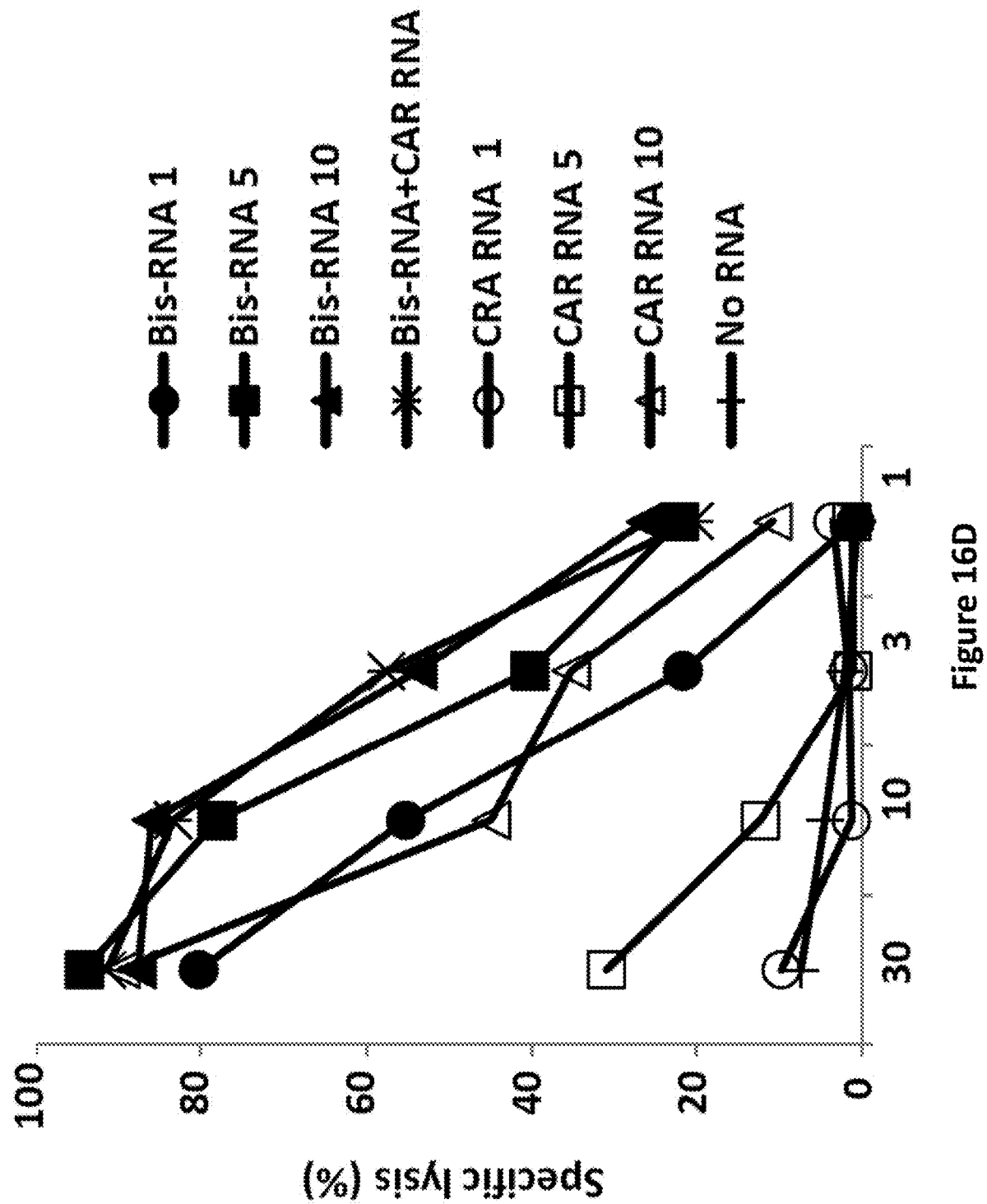
FIG. 16D is a graph showing specificity of T cells after electroporation and expression of Bis-RNA. T cells were electroporated with either Blinatumomab Bis-RNA (Bis-RNA) or CD19bbz CAR RNA (CAR RNA at RNA doses of 1, 5 or 10 µg/0.1 ml of T cells, or co-electroporated with 5 µg of each Bis-RNA and CAR RNA (Bis-RNA+CAR RNA). Eighteen hours after electroporation, lytic activity was assessed with a four hour flow based cytotoxic T lymphocyte assay at the indicated effector:target ratios.

In a four hour cytotoxic T lymphocyte assay, the lytic ability of T cells with different amounts of RNA at the doses of 1, 5 and 10 μg of either Blinatumomab Bis-RNA or CD19BBZ CAR RNA was compared. As shown in FIG. 16D, the killing ability of T cells showed correlation with the RNA doses for both Bis-RNA and CAR RNA.

To test the functional persistence of the T cells electroporated with Blinatumomab RNA, increasing doses of RNA were electroporated into the T cells, in comparison with CD19 CAR RNA. The antigen specific T cell reactivation by stimulating T cells with CD19+ tumor lines at different times after electroporation was followed by looking at CD107a up-regulation levels. As already shown in FIG. 16A for day 1 after electroporation, as long as the RNA dose was over 1 Bis-RNA T cells could be activated as efficient as 5-10 µg CD19-CAR-T cells.

Figure 18:
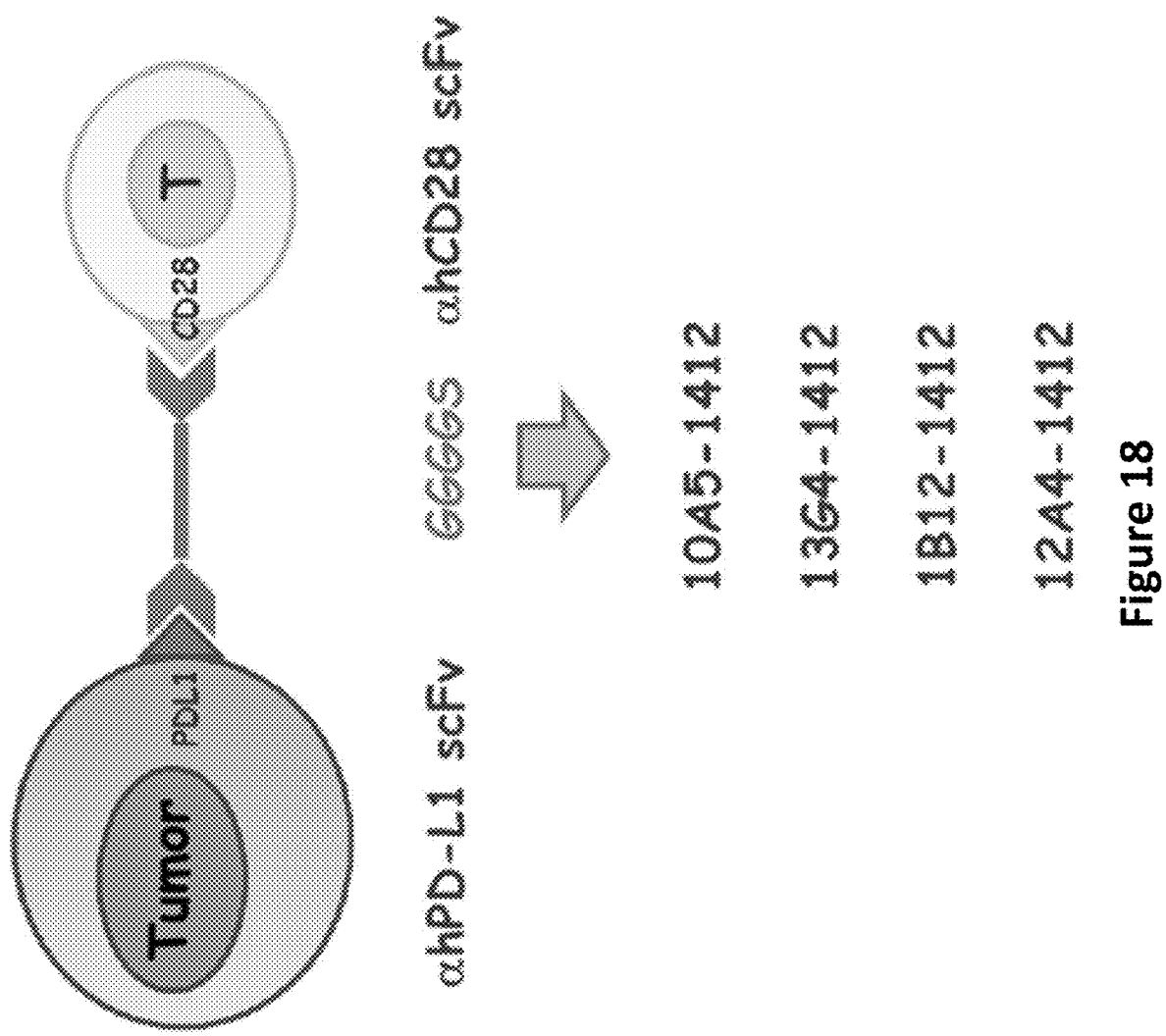
FIG. 18 is an illustration showing construction of bi-specific antibodies using anti-PD-L1 and anti-CD28 scFvs.

Four bis-specific antibodies using scFvs that could block PD-L1 (from patent No. AU2006265108A1) and an anti-CD28 scFv (1412, U.S. Pat. No. 7,585,960 B2) were designed and the genes were synthesized by PCR (FIG. 17). Sequencing verified that the DNA was properly cloned into pGEM.64A based RNA in vitro transcription vectors to generate pGEM.10A5-1-1412, pGEM.13G4-1412, pGEM.1b12-1412 and pGEM.12A4-1412 See FIG. 18.

Figure 19A:
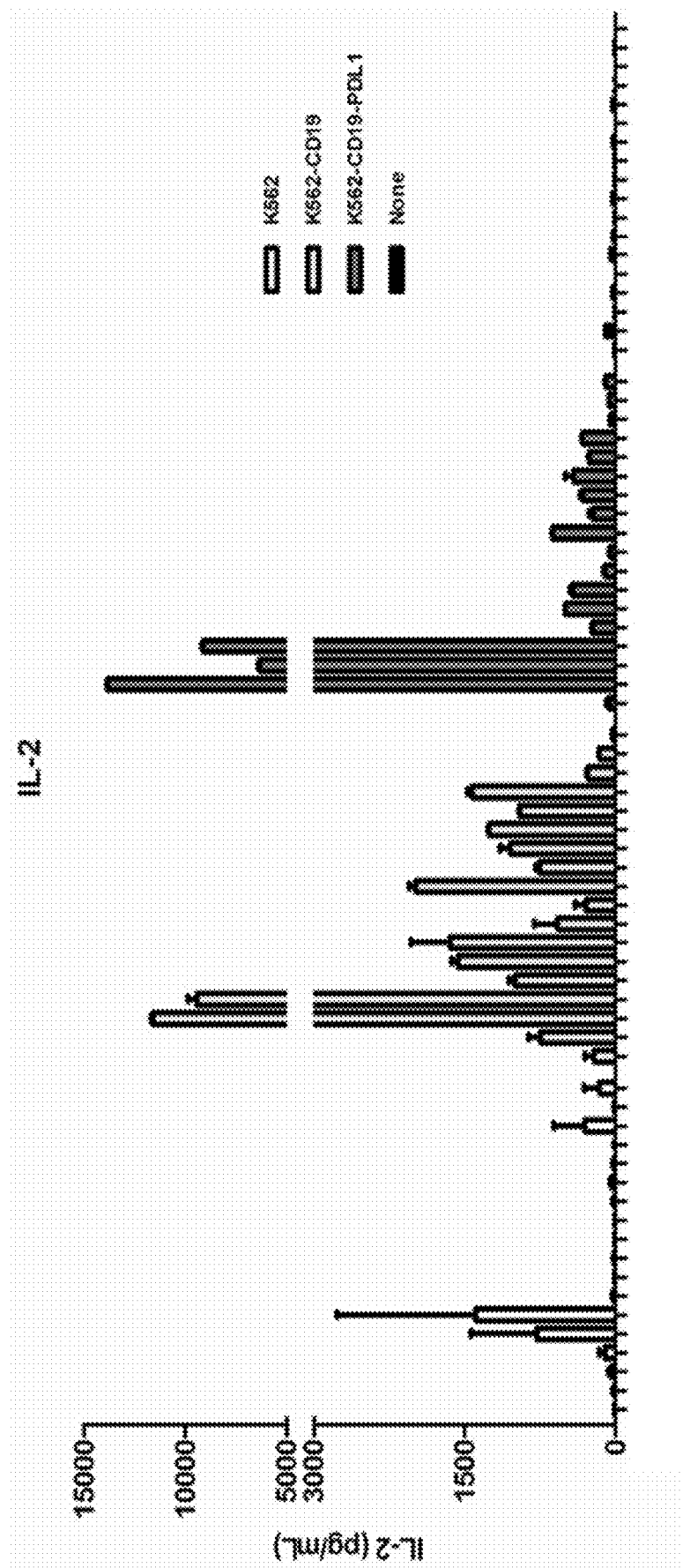
FIG. 19A is a graph showing IL-2 production by T cells electroporated with the different RNAs shown in FIGS. 3 and 5 and activated by incubation with tumor cells.
Figure 19B:
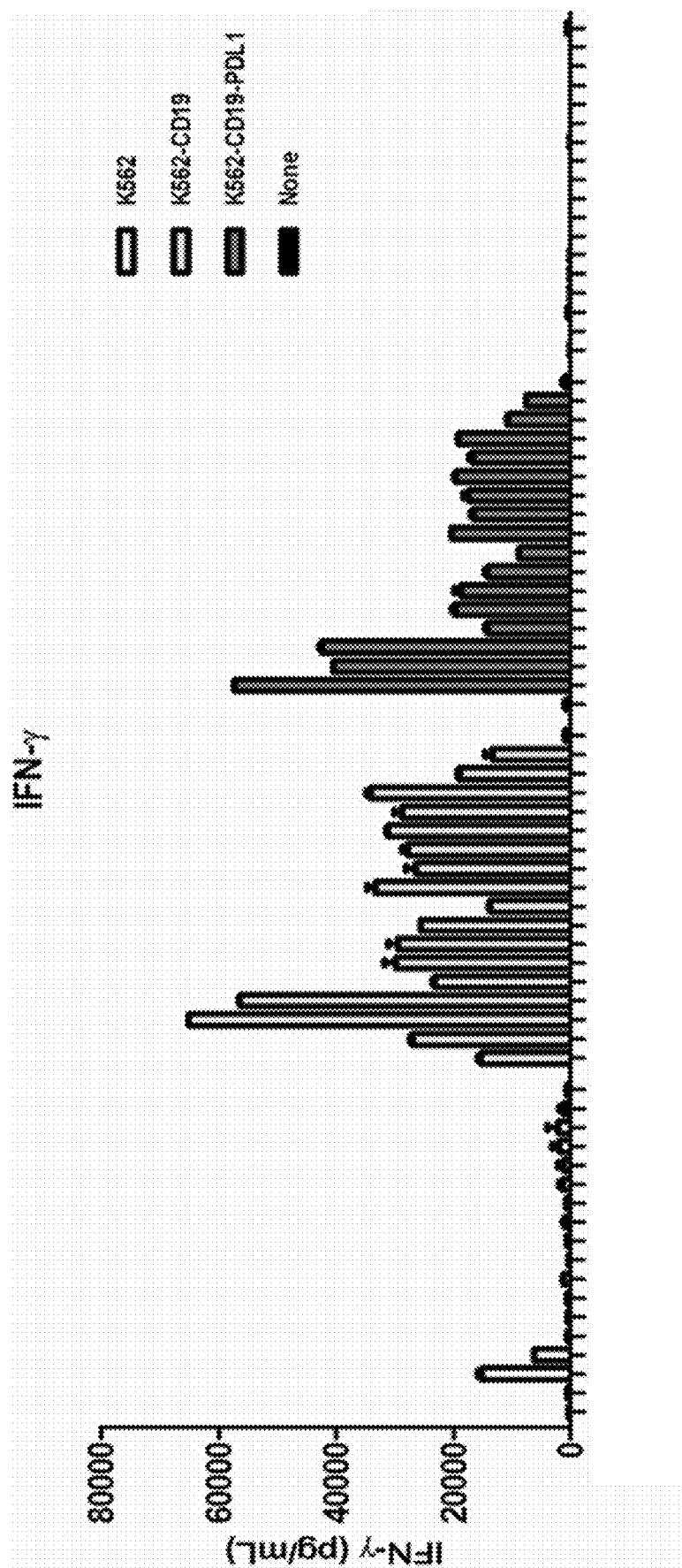
FIG. 19B is a graph showing IFN-gamma production by T cells electroporated with the different RNAs shown in FIGS. 3 and 5 and activated by incubation with tumor cells.
Figure 20:
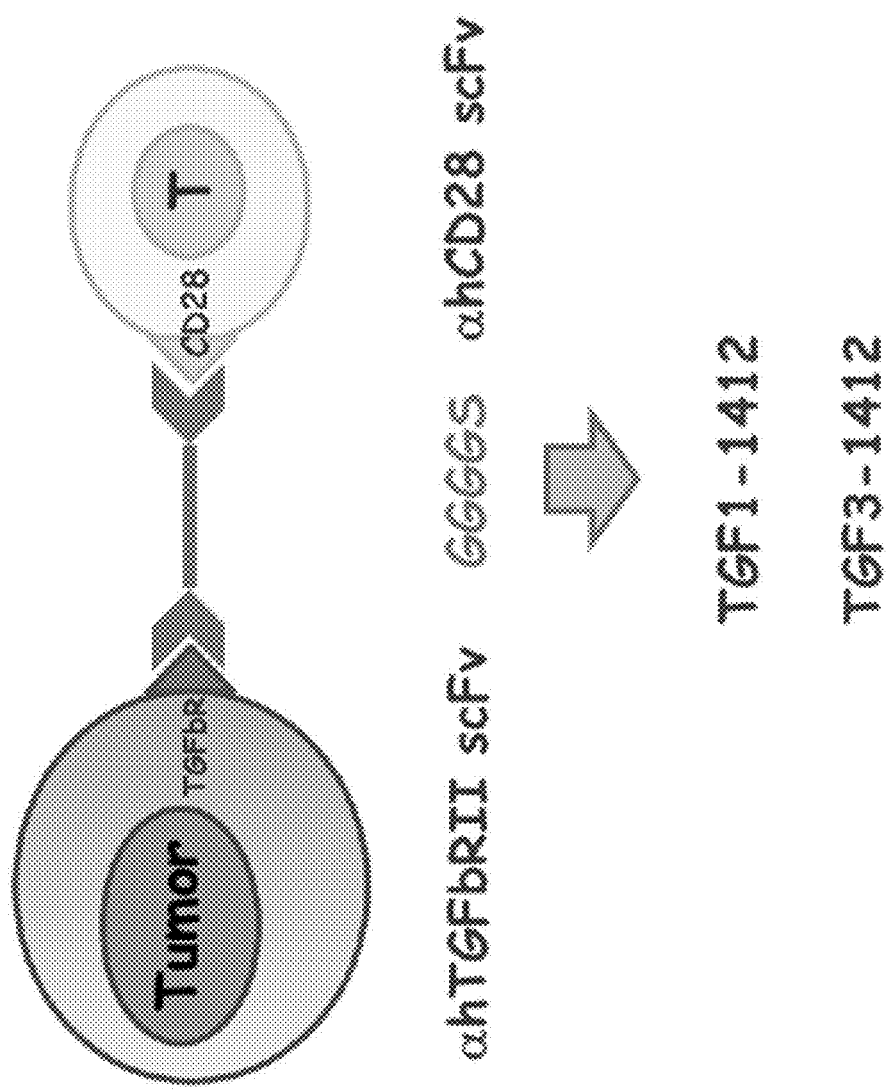
FIG. 20 is an illustration showing construction of bi-specific antibodies using anti-TGFb receptor II and anti-CD28 scFvs

Cytokine (IL2 (FIG. 19A) and IFN-gamma (FIG. 19B) production detected by ELIA showed that PD1-CD28 switch molecule, 10A5-1412 (aPDL1-aCD28 bi-RNA) and 13G4-1412 (aPDL1-aCD28 bi-RNA) could significantly improve T cell function by increasing the secretion of both IL-2 and IFN-gamma. This switch in function suggested a PD1 negative signal was switched to a CD28 positive signal. T cells with Bis-RNA switch 10A5-1412 (aPDL1-aCD28 bi-RNA) and 13G4-1412 (aPDL1-aCD28 bi-RNA) showed increased cytokine production suggesting these engineered T cells could deliver activation molecules that would positively improve T cell function.

aTGFbRII-1 and aTGFbRII-3 (from U.S. Pat. No. 8,147,834,B2) and an anti-CD28 scFv (1412, U.S. Pat. No. 7,585,960 B2) were designed and the genes were synthesized by PCR. Sequencing verified that the DNA was properly cloned into pGEM.64A based RNA in vitro transcription vectors to generate pGEM.aTGFbR-1-1412 and pGEM.aTGFbR-3-1412. See FIG. 20.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

```
Sequence listing:
TGFbR-IL12R1,
                                                     SEQ ID NO: 1
Atggaggcggcggtcgctgctccgcgtccccggctgctcctcctcgtgctggcggcggcg gcggcggcggcggcggcgctgctcccggggggcgacggcgttacagtgtttctgccacctc tgtacaaaagacaattttacttgtgtgacagatgggctctgctttgtctctgtcacagag accacagacaaagttatacacaacagcatgtgtatagctgaaattgacttaattcctcga gataggccgtttgtatgtgcaccctcttcaaaaactgggtctgtgactacaacatattgc tgcaatcaggaccattgcaataaaatagaacttccaactactgtaaagtcatcacctggc cttggtcctgtggaactggcagctgtcattgctggaccagtgtgcttcgtctgcatctca ctcatgttgatggtctatatcagggccgcacggcacctgtgcccgccgctgcccacaccc tgtgccagctccgccattgagttccctggagggaaggagacttggcagtggatcaaccca gtggacttccaggaagaggcatccctgcaggaggccctggtggtagagatgtcctgggac aaaggcgagaggactgagcctctcgagaagacagagctacctgagggtgcccctgagctg gccctggatacagagttgtccttggaggatggagacaggtgcaaggccaagatgtga TGFbR-IL12R2,
                                                     SEQ ID NO: 2
Atgggtcgggggctgctcaggggcctgtggccgctgcacatcgtcctgtggacgcgtatc gccagcacgatcccaccgcacgttcagaagtcggttaataacgacatgatagtcactgac aacaacggtgcagtcaagtttccacaactgtgtaaattttgtgatgtgagattttccacc tgtgacaaccagaaatcctgcatgagcaactgcagcatcacctccatctgtgagaagcca caggaagtctgtgtggctgtatggagaaagaatgacgagaacataacactagagacagtt tgccatgaccccaagctcccctaccatgactttattctggaagatgctgcttctccaaag tgcattatgaaggaaaaaaaaagcctggtgagactttcttcatgtgttcctgtagctct gatgagtgcaatgacaacatcatcttctcagaagaatataacaccagcaatcctgacttg ttgctagtcatatttcaagtgacaggcatcagcctcctgccaccactgggagttgccata tctgtcatcatcatcttctaccagcaaaaggtgtttgttctcctagcagccctcagacct cagtggtgtagcagagaaattccagatccagcaaatagcacttgcgctaagaaatatccc attgcagaggagaagacacagctgcccttggacaggctcctgatagactggcccacgcct gaagatcctgaaccgctggtcatcagtgaagtccttcatcaagtgaccccagttttcaga
```

-continued

```
catcccccctgctccaactggccacaaagggaaaaaggaatccaaggtcatcaggcctct gagaaagacatgatgcacagtgcctcaagcccaccacctccaagagctctccaagctgag agcagacaactggtggatctgtacaaggtgctggagagcaggggctccgacccaaagcca gaaaacccagcctgtccctggacggtgctcccagcaggtgaccttcccacccatgatggc tacttaccctccaacatagatgacctcccctcacatgaggcacctctcgctgactctctg gaagaactggagcctcagcacatctcccttt ctgttttcccctcaagttctcttcaccca ctcaccttctcctgtggtgataagctgactctggatcagttaaagatgaggtgtgactcc ctcatgctctga
``` aTGFbR-1-1412,
SEQ ID NO: 3
```
atgggttggtcctgcatcatcctgtttctcgtggccaccgccaccggcgtgcactccgaa attgtgttgacacagtctccagccaccctgtctttgtctccaggggaaagagccaccctc tcctgcagggccagtcagagtgttcgcagctacttagcctggtaccaacagaaacctggc caggctcccaggctcctcatctatgatgcatccaacagggccactggcatcccagccagg ttcagtggcagtgggtctgggacagacttcactctcaccatcagcagcctagagcctgaa gattttgcagtttattactgtcagcagcgtagcaactggcctccgacgttcggccaaggg accaaggtggaaatcaaaagtggaggggggcggttcacagctgcaggtgcaggagtcgggc ccaggactggtgaagccttcggagaccctgtccctcacctgcactgtctctggtggctcc atcagcaacagttatttctcctggggctggatccgccagccccagggaagggactggag tggattgggagtttctattatggtgaaaaaacctactacaacccgtccctcaagagccga gccaccatatccattgacacgtccaagagccagttctccctgaagctgagctctgtgacc gccgcagacacggctgtgtattactgtccgagagggcctactatgattcggggagttata gactcctggggccagggaaccctggtgACGgtgTCGTCGGGGGGCGGGGGGAGTcagGTG cagCTGgtgcagTCCGGAgccgagGTAaagaagCCAggcGCTTCCGTCAAGgtgTCATGC aagGCCTCAGGCTACACCttcACAAGCtattacatccactgggtgcgccaaGCTCCCGGT cagGGCTTGgagtggatcGGGtgcATTtacCCAGGGaacGTCAACACAaactacaacgag AAGttcaagGATcggGCAacccctgaccGTGgacACATCCatcTCTaccGCCtacatgGAG CTGTCACGCCTGCGCTCTgatGACaccGCAgtgtacttctgtaccAGGAGTcactacGGC CTGgactggAACTTTgatgtctggGGCCAGGGAaccaccgtgACGgtgtccAGTGTGGAG GGCGGTAGTggcggcTCTGGTGGGtccGGAGGCTCAggcGGCgtgatgGATgacATTcag atgacccagAGTCCCTCCtccCTCtccGCTTCCgtcggaGACCGCgtgaccatcACTTGT cacgccTCAcagaatatctacgtgtggCTGAACtggtacCAAcagaagCCCGGCaaggcc cccAAGctgCTTATCTATAAAGCGTCCaacCTCCACACGGGAGTCCCTTCCCGCttcTCC GGATCCGGCAGTGGGACGGACTTCACACTCacaatcTCGtcgCTGcagCCAGAGgacTTT GCGacgTACtactgccagcagGGCCAGacctacccaTATACTttcGGCGGCgggACCaag gtggagATTaagtaa
``` aTGFbR-3-1412,
SEQ ID NO: 4
```
atgggttggtcctgcatcatcctgtttctcgtggccaccgccaccggcgtgcactccgaa attgtgttgacacagtctccagccaccctgtctttgtctccaggggaaagagccaccctc tcctgcagggccagtcagagtgttagaagtttcttagcctggtaccaacagaaacctggc caggctcccaggctcctcatctatgatgcatccaacagggccactggcatcccagccagg
```

-continued ttcagtggcagtggggtctgggacagacttcactctcaccatcagcagcctagagcctga agattttgcagtttattactgtcagcagcgtagcaactggcctccgacgttcggccaagg gaccaaggtggaaatcaaaagtggaggggcggttcacagctacagctgcaggagtcggg cccaggactggtgaagccttcggagaccctatccctcacctgcactgtctctggtggctc catcagcagtagtagttactcctggggctggatccgccagcccccagggaagggcctgga gtggattggagtttctattacagtgggatcacctactacagcccgtccctcaagagtcga attatcatatccgaagacacgtccaagaaccagttctccctgaagctgagttctgtgacc gccgcagacacggctgtgtattactgtgcgagcgggtttactatgattcggggagcccct gactactggggccagggaaccctggtgACGgtgTCGTCGGGGGGCGGGGGAGTcagGTG cagCTGgtgcagTCCGGAgccgagGTAaagaagCCAggcGCTTCCGTCAAGgtgTCATGC aagGCCTCAGGCTACACCttcACAAGCtattacatccactgggtgcgccaaGCTCCCGGT cagGGCTTGgagtggatcGGGtgcATTtacCCAGGGaacGTCAACACAaactacaacgag AAGttcaagGATcggGCAaccctgaccGTGgacACATCCatcTCTaccGCCtacatgGAG CTGTCACGCCTGCGCTCTgatGACaccGCAgtgtacttctgtaccAGGAGTcactacGGC CTGgactggAACTTTgatgtctggGGCCAGGGAaccaccgtgACGgtgtccAGTGTGGAG GGCGGTAGTggcggcTCTGGTGGGtccGGAGGCTCAggcGGCgtgatgGATgacATTcag atgacccagAGTCCCTCCtccCTCtccGCTTCCgtcggaGACCGCgtgaccatcACTTGT cacgccTCAcagaatatctacgtgtggCTGAACtggtacCAAcagaagCCCGGCaaggcc cccAAGctgCTTATCTATAAAGCGTCCaacCTCCACACGGGAGTCCCTTCCCGCttcTCC GGATCCGGCAGTGGGACGGACTTCACACTCacaatcTCGtcgCTGcagCCAGAGgacTTT GCGacgTACtactgccagcagGGCCAGacctacccaTATACTttcGGCGGCgggACCaag gtggagATTaagtaa

CD86-PD-L1,
SEQ ID NO: 5

Atggatccccagtgcactatgggactgagtaacattctctttgtgatggccttcctgctc tctggtgctgctcctctgaagattcaagcttatttcaatgagactgcagacctgccatgc caatttgcaaactctcaaaaccaaagcctgagtgagctagtagtattttggcaggaccag gaaaacttggttctgaatgaggtatacttaggcaaagagaaatttgacagtgttcattcc aagtatatgggccgcacaagttttgattcggacagttggaccctgagacttcacaatctt cagatcaaggacaagggcttgtatcaatgtatcatccatcacaaaaagcccacaggaatg attcgcatccaccagatgaattctgaactgtcagtgcttgctaacttcagtcaacctgaa atagtaccaatttctaatataacagaaaatgtgtacataaatttgacctgctcatctata cacggttacccagaacctaagaagatgagtgttttgctaagaaccaagaattcaactatc gagtatgatggtattatgcagaaatctcaagataatgtcacagaactgtacgacgtttcc atcagcttgtctgtttcattccctgatgttacgagcaatatgaccatatctgtattctgg aaactgacaagacgcggatttatatcacctttactatagagcttgaggaccacagcctcc cccagaccacattcctggcGGAGGGGGAagtggcGGGGGTgggtccGGCggcGGCggcTC Gtttactgtcacggttcccaaggacctatatgtggtagagtatggtagcaatatgacaat tgaatgcaaattcccagtagaaaaacaattagacctggctgcactaattgtctattggga aatggaggataagaacattattcaatttgtgcatggagaggaagacctgaaggttcagca tagtagctacagacagagggcccggctgttgaaggaccagctaccagggaaatgctgcac ttcagatcacagatgtgaaattgcaggatgcaggggtgtaccgctgcatgatcagctatg -continued gtggtgccgactacaagcgaattactgtgaaagtcaatgccccatacaacaaaatcaacc aaagaattttggttgtggatccagtcacctagaacatgaactgacatgtcaggctgaggg ctaccccaaggccgaagtcatctggacaagcagtgaccatcaagtcctgagtggtaagac caccaccaccaattccaagagagaggagaagatttcaatgtgaccagcacactgagaatc aacacaacaactaatgagattttctactgcacttttaggagattagatcctgaggaaaac catacagagaattggtcatcccagaactacctctggcacatcctccaaatgaaaggTAA

CD86-PD-L2,

SEQ ID NO: 6

Atggatccccagtgcactatgggactgagtaacattctctttgtgatggccttcctgctc tctggtgctgctcctctgaagattcaagcttatttcaatgagactgcagacctgccatgc caatttgcaaactctcaaaaccaaagcctgagtgagctagtagtattttggcaggaccag gaaaacttggttctgaatgaggtatacttaggcaaagagaaatttgacagtgttcattcc aagtatatgggccgcacaagttttgattcggacagttggaccctgagacttcacaatctt cagatcaaggacaagggcttgtatcaatgtatcatccatcacaaaaagcccacaggaatg attcgcatccaccagatgaattctgaactgtcagtgcttgctaacttcagtcaacctgaa atagtaccaatttctaatataacagaaaatgtgtacataaatttgacctgctcatctata cacggttacccagaacctaagaagatgagtgtttttgctaagaaccaagaattcaactatc gagtatgatggtattatgcagaaatctcaagataatgtcacagaactgtacgacgtttcc atcagcttgtctgtttcattccctgatgttacgagcaatatgaccatcttctgtattctg gaaactgacaagacgcggcttttatcttcacctttctctatagagcttgaggaccctcag cctcccccagaccacattcctggcGGAGGGGGAagtggcGGGGGTgggtccGGCggcGGC ggcTCGTtattcacagtgacagtccctaaggaactgtacataatagagcatggcagcaat gtgaccctggaatgcaactttgacactggaagtcatgtgaaccttggagcaataacagcc agtttgcaaaaggtggaaaatgatacatccccacaccgtgaaagagccactttgctggag gagcagctgccctagggaaggcctcgttccacatacctcaagtccaagtgagggacgaa ggacagtaccaatgcataatcatctatggggtcgcctgggactacaagtacctgactctg aaagtcaaagcttcctacaggaaaataaacactcacatcctaaaggttccagaaacagat gaggtagagctcacctgccaggctacaggttatcctctggcagaagtatcctggccaaac gtcagcgttcctgccaacaccagccactccaggacccctgaaggcctctaccaggtcacc agtgttctgcgcctaaagccaccccctggcagaaacttcagctgtgtgttctggaatact cacgtgagggaacttactttggccagcattgaccttcaaagtcagatggaacccaggacc catccaactTAA

CD80-PD-L1,

SEQ ID NO: 7 atgggccacacacggaggcagggaacatcaccatccaagtgtccatacctcaatttattc agctatggtgctggctggtattctcacttctgttcaggtgttatccacgtgaccaaggaa gtgaaagaagtggcaacgctgtcctgtggtcacaatgtttctgttgaagagctggcacaa actcgcatctactggcaaaaggagaagaaaatggtgctgactatgatgtctggggacatg aatatatggcccgagtacaagaaccggaccatctttgatatcactaataacctctccatt gtgatcctggctctgcgcccatctgacgagggcacatacgagtgtgttgttctgaagtat gaaaaagacgctttcaagcgggaacacctggctgaagtgacgttatcagtcaaagctgac ttccctacacctagtatatctgactttgaaattccaacttctaatattagaaggataatt -continued tgctcaacctctggaggttttccagagcctcacctctcctggttggaaaatggagaagaa ttaaatgccatcaacacaacagtttcccaagatcctgaaactgagctctatgctgttagc agcaaactggatttcaatatgacaaccaaccacagcttcatgtgtctcatcaagtatgga catttaagagtgaatcagaccttcaactggaatacaaccaagcaagagcattttcctgat aacggcGGAGGGGGAagtggcGGGGGTgggtccGGCggcGGCggcTCGtttactgtcacg gttcccaaggacctatatgtggtagagtatggtagcaatatgacaattgaatgcaaattc ccagtagaaaaacaattagacctggctgcactaattgtctattgggaaatggaggataag aacattattcaatttgtgcatggagaggaagacctgaaggttcagcatagtagctacaga cagagggcccggctgttgaaggaccagctctccctgggaaatgctgcacttcagatcaca gatgtgaaattgcaggatgcaggggtgtaccgctgcatgatcagctatggtggtgccgac tacaagcgaattactgtgaaagtcaatgccccatacaacaaaatcaaccaaagaattttg gttgtggatccagtcacctctgaacatgaactgacatgtcaggctgagggctaccccaag gccgaagtcatctggacaagcagtgaccatcaagtcctgagtggtaagaccaccaccacc aattccaagagagaggagaagcttttcaatgtgaccagcacactgagaatcaacacaaca actaatgagattttctactgcacttttaggagattagatcctgaggaaaaccatacagct gaattggtcatcccagaactacctctggcacatcctccaaatgaaaggTAA

CD80-PD-L2,

SEQ ID NO: 8 atgggccacacacggaggcagggaacatcaccatccaagtgtccatacctcaatttattc agctcttggtgctggctggtattctcacttctgttcaggtgttatccacgtgaccaagga agtgaaagaagtggcaacgctgtcctgtggtcacaatgtttctgttgaagagaggcacaa actcgcatctactggcaaaaggagaagaaaatggtgctgactatgatgtaggggacatga atatatggcccgagtacaagaaccggaccatattgatatcactaataacctaccattgtg atcctggactgcgcccatctgacgagggcacatacgagtgtgttgttctgaagtatgaaa aagacgattcaagcgggaacacctggctgaagtgacgttatcagtcaaagctgacttccc tacacctagtatatctgactttgaaattccaacttctaatattagaaggataatttgctc aacctaggaggttttccagagcctcacctacctggttggaaaatggagaagaattaaatg ccatcaacacaacagtttcccaagatcctgaaactgagactatgctgttagcagcaaact ggatttcaatatgacaaccaaccacagcttcatgtgtctcatcaagtatggacatttaag agtgaatcagaccttcaactggaatacaaccaagcaagagcattttcctgataacggcGG AGGGGGAagtggcGGGGGTgggtccGGCggcGGCggcTCGTtattcacagtgacagtccc taaggaactgtacataatagagcatggcagcaatgtgaccaggaatgcaactttgacact ggaagtcatgtgaaccttggagcaataacagccagtttgcaaaaggtggaaaatgataca tccccacaccgtgaaagagccactttgctggaggagcagagcccctagggaaggcctcgt tccacatacctcaagtccaagtgagggacgaaggacagtaccaatgcataatcatctatg gggtcgcctgggactacaagtacctgactctgaaagtcaaagcttcctacaggaaaataa acactcacatcctaaaggttccagaaacagatgaggtagagctcacctgccaggctacag gttatcctaggcagaagtatcctggccaaacgtcagcgttcctgccaacaccagccactc caggacccagaaggcctctaccaggtcaccagtgttctgcgcctaaagccaccccctggc agaaacttcagagtgtgttctggaatactcacgtgagggaacttaattggccagcattga ccttcaaagtcagatggaacccaggacccatccaactTAA -continued PD-L1-CD86,
SEQ ID NO: 9
atgaggatatttgctgtctttatattcatgacctactggcatttgctgaacgcatttact gtcacggttcccaaggacctatatgtggtagagtatggtagcaatatgacaattgaatgc aaattcccagtagaaaaacaattagacctggctgcactaattgtctattgggaaatggag gataagaacattattcaatttgtgcatggagaggaagacctgaaggttcagcatagtagc tacagacagagggcccggctgttgaaggaccagctctccctgggaaatgctgcacttcag atcacagatgtgaaattgcaggatgcaggggtgtaccgctgcatgatcagctatggtggt gccgactacaagcgaattactgtgaaagtcaatgccccatacaacaaaatcaaccaaga attttggttgtggatccagtcacctctgaacatgaactgacatgtcaggctgagggctac cccaaggccgaagtcatctggacaagcagtgaccatcaagtcctgagtggtaagaccacc accaccaattccaagagagaggagaagcttttcaatgtgaccagcacactgagaatcaac acaacaactaatgagattttctactgcacttttaggagattagatcctgaggaaaaccat acagctgaattggtcatcccagaactacctctggcacatcctccaaatgaaaggggcGGA GGGGGAagtggcGGGGGTgggtccGGCggcGGCggcTCGggtgctgctcctctgaagatt caagcttatttcaatgagactgcagacctgccatgccaatttgcaaactctcaaaaccaa agcctgagtgagctagtagtattttggcaggaccaggaaaacttggttctgaatgaggta tacttaggcaaagagaaatttgacagtgttcattccaagtatatgggccgcacaagtttt gattcggacagttggaccctgagacttcacaatcttcagatcaaggacaagggcttgtat caatgtatcatccatcacaaaaagcccacaggaatgattcgcatccaccagatgaattct gaactgtcagtgcttgctaacttcagtcaacctgaaatagtaccaatttctaatataaca gaaaatgtgtacataaatttgacctgctcatctatacacggttacccagaacctaagaag atgagtgttttgctaagaaccaagaattcaactatcgagtatgatggtattatgcagaaa tctcaagataatgtcacagaactgtacgacgtttccatcagcttgtctgtttcattccct gatgttacgagcaatatgaccatcttctgtattctggaaactgacaagacgcggctttta tcttcacctttctctatagagcttgaggaccctcagcctcccccagaccacattcctTAA PD-L1-CD80,
SEQ ID NO: 10
atgaggatatttgctgtattatattcatgacctactggcatttgctgaacgcatttactg tcacggttcccaaggacctatatgtggtagagtatggtagcaatatgacaattgaatgca aattcccagtagaaaaacaattagacctggctgcactaattgtctattgggaaatggagg ataagaacattattcaatttgtgcatggagaggaagacctgaaggttcagcatagtagct acagacagagggcccggctgttgaaggaccagctctccctgggaaatgctgcacttcaga tcacagatgtgaaattgcaggatgcaggggtgtaccgctgcatgatcagctatggtggtg ccgactacaagcgaattactgtgaaagtcaatgccccatacaacaaaatcaaccaaagaa ttttggttgtggatccagtcacctctgaacatgaactgacatgtcaggctgagggctacc ccaaggccgaagtcatctggacaagcagtgaccatcaagtcctgagtggtaagaccacca ccaccaattccaagagagaggagaagcttttcaatgtgaccagcacactgagaatcaaca caacaactaatgagattttctactgcacttttaggagattagatcctgaggaaaaccata cagctgaattggtcatcccagaactacctctggcacatcctccaaatgaaaggggcGGAG GGGGAagtggcGGGGGTgggtccGGCggcGGCggcTCGtcttttctcacttctgttcaggt gttatccacgtgaccaaggaagtgaaagaagtggcaacgctgtcctgtggtcacaatgtt -continued

```
tctgttgaagagctggcacaaactcgcatctactggcaaaaggagaagaaaatggtgctg actatgatgtctggggacatgaatatatggcccgagtacaagaaccggaccatctttgat atcactaataacctctccattgtgatcctggctctgcgcccatctgacgagggcacatac gagtgtgttgttctgaagtatgaaaaagacgctttcaagcgggaacacctggctgaagtg acgttatcagtcaaagctgacttccctacacctagtatatctgactttgaaattccaact tctaatattagaaggataatttgctcaacctctggaggttttccagagcctcacctctcc tggttggaaaatggagaagaattaaatgccatcaacacaacagtttcccaagatcctgaa actgagctctatgctgttagcagcaaactggatttcaatatgacaaccaaccacagcttc atgtgtctcatcaagtatggacatttaagagtgaatcagaccttcaactggaatacaacc aagcaagagcatttcctgataacTAA
```

PD-L2-CD86,
SEQ ID NO: 11

```
atgatcttcctcctgctaatgttgagcctggaattgcagcttcaccagatagcagcttta ttcacagtgacagtccctaaggaactgtacataatagagcatggcagcaatgtgaccctg gaatgcaactttgacactggaagtcatgtgaaccttggagcaataacagccagtttgcaa aaggtggaaaatgatacatccccacaccgtgaaagagccactttgctggaggagcagctg cccctagggaaggcctcgttccacatacctcaagtccaagtgagggacgaaggacagtac caatgcataatcatctatgggtcgcctgggactacaagtacctgactctgaaagtcaaa gcttcctacaggaaaataaacactcacatcctaaaggttccagaaacagatgaggtagag ctcacctgccaggctacaggttatcctctggcagaagtatcctggccaaacgtcagcgtt cctgccaacaccagccactccaggaccccctgaaggcctctaccaggtcaccagtgttctg cgcctaaagccaccccctggcagaaacttcagctgtgtgttctggaatactcacgtgagg gaacttactttggccagcattgaccttcaaagtcagatggaacccaggacccatccaact ggcGGAGGGGGAagtggcGGGGGTgggtccGGCggcGGCggcTCGggtgctgctcctctg aagattcaagcttatttcaatgagactgcagacctgccatgccaatttgcaaactctcaa aaccaaagcctgagtgagctagtagtattttggcaggaccaggaaaacttggttctgaat gaggtatacttaggcaaagagaaatttgacagtgttcattccaagtatatgggccgcaca agttttgattcggacagttggaccctgagacttcacaatcttcagatcaaggacaagggc ttgtatcaatgtatcatccatcacaaaaagcccacaggaatgattcgcatccaccagatg aattctgaactgtcagtgcttgctaacttcagtcaacctgaaatagtaccaatttctaat ataacagaaaatgtgtacataaatttgacctgctcatctatacacggttacccagaacct aagaagatgagtgttttgctaagaaccaagaattcaactatcgagtatgatggtattatg cagaaatctcaagataatgtcacagaactgtacgacgtttccatcagcttgtctgtttca ttccctgatgttacgagcaatatgaccatcttctgtattctggaaactgacaagacgcgg ctttttatcttcacctttctctatagagcttgaggaccctcagcctcccccagaccacatt cct
```

Anti-hPD-L1 scFv(VK-VH) 12A4,
SEQ ID NO: 12

MGWSCIILFLVATATGVHSEIVLTQSPATLSLSPGERATLSCRASQSVSSYLAWYQ

QKPGQAPRLLIYDASNRATGIPARFSGSGSGTDFTLTISSLEPEDFAVYYCQQRSN

WPTFGQGTKVEIKSGGGGSQVQLVQSGAEVKKPGSSVKVSCKTSGDTFSTYAISWV

RQAPGQGLEWMGGIIPIFGKAHYAQKFQGRVTITADESTSTAYMELSSLRSEDTAV

YFCARKFHFVSGSPFGMDVWGQGTTVTVSS

13G4,
SEQ ID NO: 13
MGWSCIILFLVATATGVHSAIQLTQSPSSLSASVGDRVTITCRASQGISSALAWYQ

QKPGKAPKLLIYDASSLESGVPSRFSGSGSGTDFTLTISSLQPEDFATYYCQQFNS

YPFTFGPGTKVDIKSGGGGSEVQLVESGGGLVQPGRSLRLSCAASGITFDDYGMHW

VRQAPGKGLEWVSGISWNRGRIEYADSVKGRFTISRDNAKNSLYLQMNSLRAEDTA

LYYCAKGRFRYFDWFLDYWGQGTLVTVSS

1B12,
SEQ ID NO: 14
MGWSCIILFLVATATGVHSEIVLTQSPATLSLSPGERATLSCRASQSVSSYLAWYQ

QKPGQAPRLLIYDASNRATGIPARFSGSGSGTDFTLTISSLEPEDFAVYYCQQRSN

WPTFGQGTKVEIKSGGGGSQVQLVQSGAEVKKPGSSVKVSCKTSGDTFSSYAISWV

RQAPGQGLEWMGGIIPIFGRAHYAQKFQGRVTITADESTSTAYMELSSLRSEDTAV

YFCARKFHFVSGSPFGMDVWGQGTTVTVSS

10A5,
SEQ ID NO: 15
MGWSCIILFLVATATGVHSDIQMTQSPSSLSASVGDRVTITCRASQGISSWLAWYQQ

KPEKAPKSLIYAASSLQSGVPSRFSGSGSGTDFTLTISSLQPEDFATYYCQQYNSYP

YTFGQGTKLEIKSGGGGSQVQLVQSGAEVKKPGASVKVSCKASGYTFTSYDVHWVRQ

APGQRLEWMGWLHADTGITKFSQKFQGRVTITRDTSASTAYMELSSLRSEDTAVYY

CARERIQLWFDYWGQGTLVTVSS

3G10,
SEQ ID NO: 16
MGWSCIILFLVATATGVHSEIVLTQSPATLSLSPGERATLSCRASQSVSSYLVWY

QQKPGQAPRLLIYDASNRATGIPARFSGSGSGTDFTLTISSLEPEDFAVYYCQQR

SNWPRTFGQGTKVEIKSGGGGSQVQLVQSGAEVKKPGASVKVSCKASGYTFTDYG

FSWVRQAPGQGLEWMGWITAYNGNTNYAQKLQGRVTMTTDTSTSTVYMELRSLRS

DDTAVYYCARDYFYGMDVWGQGTTVTVSS

Anti-hCD28 scFv (VH-VL),
SEQ ID NO: 17
GGGGSQVQLVQSGAEVKKPGASVKVSCKASGYTFTSYYIHWVRQAPGQGLEWIGCI

YPGNVNTNYNEKFKDRATLTVDTSISTAYMELSRLRSDDTAVYFCTRSHYGLDWNF

DVWGQGTTVTVSSVEGGSGGSGGSGGSGGVDDIQMTQSPSSLSASVGDRVTITCHA

SQNIYVWLNWYQQKPGKAPKLLIYKASNLHTGVPSRFSGSGSGTDFTLTISSLQPE

DFATYYCQQGQTYPYTFGGGTKVEIK

---

What is claimed is:

1. A method for enhancing T cell antitumor activity in a subject in need thereof, the method comprising parenterally administering to the subject a composition comprising modified CAR T cells comprising a nucleic acid sequence encoding a switch molecule and a nucleic acid sequence encoding a CAR comprising an antigen binding domain that targets a tumor antigen, a transmembrane domain, a costimulatory domain, and an intracellular signaling domain;

wherein the switch molecule comprises:
(a) an extracellular domain of a transforming growth factor-beta receptor (TGF-beta-R), an intracellular domain of a signaling receptor selected from the group consisting of interleukin-12 receptor (IL-12R), CD3, CD28, CD137, CD27, ICOS, and OX40, and a transmembrane domain derived from the same molecule as the extracellular domain or the same molecule as the intracellular domain;

(b) an extracellular domain of a programmed cell death 1 (PD1) receptor, an intracellular domain of a signaling receptor selected from the group consisting of interleukin-12 receptor (IL-12R), CD3, CD28, CD137, CD27, ICOS, and OX40, and a transmembrane domain derived from the same molecule as the extracellular domain or the same molecule as the intracellular domain;

(c) an extracellular domain of a programmed cell death ligand 1 (PDL1) receptor, an intracellular domain of a signaling receptor selected from the group consisting of interleukin-12 receptor (IL-12R), CD3, CD28, CD137, CD27, ICOS, and OX40, and a transmembrane domain derived from the same molecule as the extracellular domain or the same molecule as the intracellular domain; or (d) an extracellular domain of an interferon-gamma receptor (IFN-gamma) receptor, an intracellular domain of a signaling receptor selected from the group consisting of interleukin-12 receptor (IL-12R), CD3, CD28, CD137, CD27, ICOS, and OX40, and a transmembrane domain derived from the same molecule as the extracellular domain or the same molecule as the intracellular domain;

wherein the modified CAR T cells home to a target tumor site; and wherein when the modified CAR T cells express the switch molecule, interaction of the extracellular domain of the switch molecule with TGFβ, PD1, PDL1, or IFN-γ in the tumor microenvironment converts an inhibitory signal of the TGFβ receptor, the PD1 receptor, the PDL1 receptor, or the IFN-γ receptor into an IL-12R, CD3, CD28, CD137, CD27, ICOS, or OX40 stimulatory signal thereby enhancing the antitumor activities of the modified CAR T cells.

2. The method according to claim 1, wherein the switch molecule comprises the extracellular domain of TGF-beta-R.

3. The method according to claim 2, wherein the signaling receptor is IL-12R.

4. The method according to claim 1, wherein the nucleic acid comprises in vitro transcribed RNA or synthetic RNA.

5. The method according to claim 1, wherein enhancing the antitumor activities of the modified CAR T cells comprises inducing a secretion of an activation factor at the target tumor site, and wherein the activation factor is a soluble cytokine selected from the group consisting of IL-1, IL-2, IL-6, IL-7, IL-8, IL-10, IL-12, IL-15, IL-21, TNF, TGF, IFN, and functional fragments and variants thereof.

6. The method according to claim 1, wherein the tumor target site is selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

7. The method according to claim 1, wherein the modified CAR T cells home to a solid tumor site.

8. The method according to claim 1, wherein the modified CAR T cells home to a cancer expressing a tumor antigen selected from the group consisting of p53, Ras, beta-Catenin, CDK4, alpha-Actinin-4, Tyrosinase, TRP1/gp75, TRP2, gp100, Melan-A/MART1, Gangliosides, PSMA, HER2, WT1, EphA3, EGFR, CD19, CD20, MAGE, BAGE, GAGE, NY-ESO-1, Telomerase, Survivin, and any combination thereof.

9. The method according to claim 8, wherein the modified CAR T cells express a nucleic acid encoding TGF-beta-IL-12 switch molecule and a nucleic acid encoding a CD19 CAR or a HER2 CAR.

10. The method according to claim 1, wherein the modified CAR T cells are activated.

11. The method according to claim 1, wherein the modified CAR T cells induce lysis of cells and/or tissues at the tumor target site.

12. The method according to claim 1, wherein the modified CAR T cells are cryopreserved.

13. The method according to claim 1, wherein the subject is a human.

14. The method according to claim 1, wherein the composition further comprises a pharmaceutically acceptable carrier.

15. The method according to claim 1, wherein the CAR targets a tumor antigen selected from the group consisting of TRP1/gp75, TRP2, gp100, Melan-A/MART1, Gangliosides, PSMA, HER2, WT1, EphA3, EGFR, CD19, CD20, MAGE, and NY-ESO-1.

16. The method according to claim 1, wherein the switch molecule is expressed transiently.

17. The method according to claim 1, wherein the composition is administered to the subject more than once.

18. The method according to claim 1, wherein the modified CART cells are autologous or allogeneic to the subject.

19. The method according to claim 1, wherein the antitumor activity is for a cancer selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and combinations thereof.

20. The method according to claim 1, wherein the transmembrane domain is a CD28 transmembrane domain.

21. A method for enhancing T cell antitumor activity in a subject in need thereof, the method comprising parenterally administering to the subject a composition comprising modified T cells comprising a nucleic acid sequence encoding a switch molecule and a nucleic acid sequence encoding a chimeric antigen receptor (CAR) that targets a tumor antigen, wherein the tumor antigen is selected from the group consisting of p53, Ras, beta-Catenin, CDK4, alpha-Actinin-4, Tyrosinase, TRP1/gp75, TRP2, gp100, Melan-A/MART1, Gangliosides, PSMA, HER2, WT1, EphA3, EGFR, CD19, CD20, MAGE, BAGE, GAGE, NY-ESO-1, telomerase, and survivin;

wherein the switch molecule comprises:

(a) an extracellular domain of a transforming growth factor-beta receptor (TGF-beta-R), an intracellular domain of a signaling receptor selected from the group consisting of interleukin-12 receptor (IL-12R), CD3, CD28, CD137, CD27, ICOS, and OX40, and a transmembrane domain derived from the same molecule as the extracellular domain; or the same molecule as the intracellular domain;

(b) an extracellular domain of a programmed cell death 1 (PD1) receptor, an intracellular domain of a signaling receptor selected from the group consisting of interleukin-12 receptor (IL-12R), CD3, CD28, CD137, CD27, ICOS, and OX40, and a transmembrane domain derived from the same molecule as the extracellular domain, or the same molecule as the intracellular domain;
- (c) an extracellular domain of a programmed cell death ligand 1 (PDL1) receptor, an intracellular domain of a signaling receptor selected from the group consisting of interleukin-12 receptor (IL-12R), CD3, CD28, CD137, CD27, ICOS, and OX40, and a transmembrane domain derived from the same molecule as the extracellular domain, or the same molecule as the intracellular domain; or
- (d) an extracellular domain of an interferon-gamma receptor (IFN-gamma) receptor, an intracellular domain of a signaling receptor selected from the group consisting of interleukin-12 receptor (IL-12R), CD3, CD28, CD137, CD27, ICOS, and OX40, and a transmembrane domain derived from the same molecule as the extracellular domain, or the same molecule as the intracellular domain;

wherein the modified T cells home to a target tumor site; and wherein when the modified T cells express the switch molecule, interaction of the extracellular domain of the switch molecule with TGFβ, PD1, PDL1, or IFN-γ in the tumor site converts the inhibitory signal of the TGFβ receptor, the PD1 receptor, the PDL1 receptor, or the IFN-γ receptor into the IL-12R, the CD3, the CD28, the CD137, the CD27, the ICOS, or the OX40 stimulatory signal, thereby enhancing antitumor activities of the modified T cells.

* * * * *